US008299040B2

(12) United States Patent
Mehta et al.

(10) Patent No.: US 8,299,040 B2
(45) Date of Patent: Oct. 30, 2012

(54) METHODS FOR TREATING CANCER TARGETING TRANSGLUTAMINASE

(75) Inventors: Kapil Mehta, Bellaire, TX (US); Amit Verma, Haryana (IN); Sushovan Guha, Missouri City, TX (US); Jansina Fok, Houston, TX (US); Gabriel Lopez-Berestein, Bellaire, TX (US); Anil Sood, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 56 days.

(21) Appl. No.: 11/867,717

(22) Filed: Oct. 5, 2007

(65) Prior Publication Data

US 2008/0279844 A1 Nov. 13, 2008

Related U.S. Application Data

(60) Provisional application No. 60/852,800, filed on Oct. 18, 2006.

(51) Int. Cl.

| | |
|---|---|
| ***C07H 21/02*** | (2006.01) |
| ***C07H 21/04*** | (2006.01) |
| ***A61K 31/70*** | (2006.01) |
| *C12Q 1/68* | (2006.01) |

(52) U.S. Cl. .................... 514/44 A; 536/23.1; 536/24.1; 536/24.5; 435/375; 435/377

(58) Field of Classification Search ........................ None
See application file for complete search history.

(56) References Cited

U.S. PATENT DOCUMENTS

| | | | | |
|---|---|---|---|---|
| 2004/0259247 | A1* | 12/2004 | Tuschl et al. | 435/375 |
| 2005/0197310 | A1* | 9/2005 | Mor et al. | 514/44 |
| 2005/0245473 | A1 | 11/2005 | Saunders et al. | |
| 2007/0031844 | A1* | 2/2007 | Khvorova et al. | 435/6 |

OTHER PUBLICATIONS

Han et al., J. Cancer Res. Clin. Oncol. vol. 125:89-95, 1999.*
Mann et al., TG2 inhibition and correlation of TG2 expression with pancreatic ductile carcinoma. Cancer Res. Sep. 1, 2006, vol. 66, pp. 8788-8795.
Bae et al. Down-Regulation of Transglutaminase II leads to Impaired Motility of Cancer Cells by Inactivation of the Protein Kinase Akt, and Decrease of Reactive Oxygen Species. Biotechnol. Letters, Jun. 29, 2006, vol. 28, pp. 1151-1158.
Herman et al. Implications of Increased Tissue Transglutaminase (TG2) Expression in Drug-Resistant Breast Cancer Cell. Oncogene, Jan. 30, 2006, vol. 25, pp. 3049-3058.
Fok et al. Implications of Tissue Transglutaminase Expression in Malignant Melanoma. Mol. Cancer Ther. Jun. 2006, vol. 5, No. 6, pp. 1493-1503.
Notification of Transmittal of the International Search Report and the Written Opinion of the International Searching Authority, or the Declaration , PCT/US07/80521, May 10, 2007.

* cited by examiner

*Primary Examiner* — Sean McGarry
(74) *Attorney, Agent, or Firm* — Nielsen IP Law LLC

(57) ABSTRACT

A method for treating cancer comprising inhibiting transglutaminase activity is provided. Suitable cancer types for which the methods of the present disclosure can be used to treat include, but are not limited to, pancreatic, breast, and ovarian cancers and melanoma. The inhibition of transglutaminase activity may be performed by one or more techniques, including, but not limited to, downregulating transglutaminase expression, inhibiting TG2 translation, or blocking TG2 enzymatic activity, such as with a small molecule inhibitor or intracellular antibody (intrabody).

6 Claims, 34 Drawing Sheets

A

B

A

B

A

TG2 expression

Figure 1:
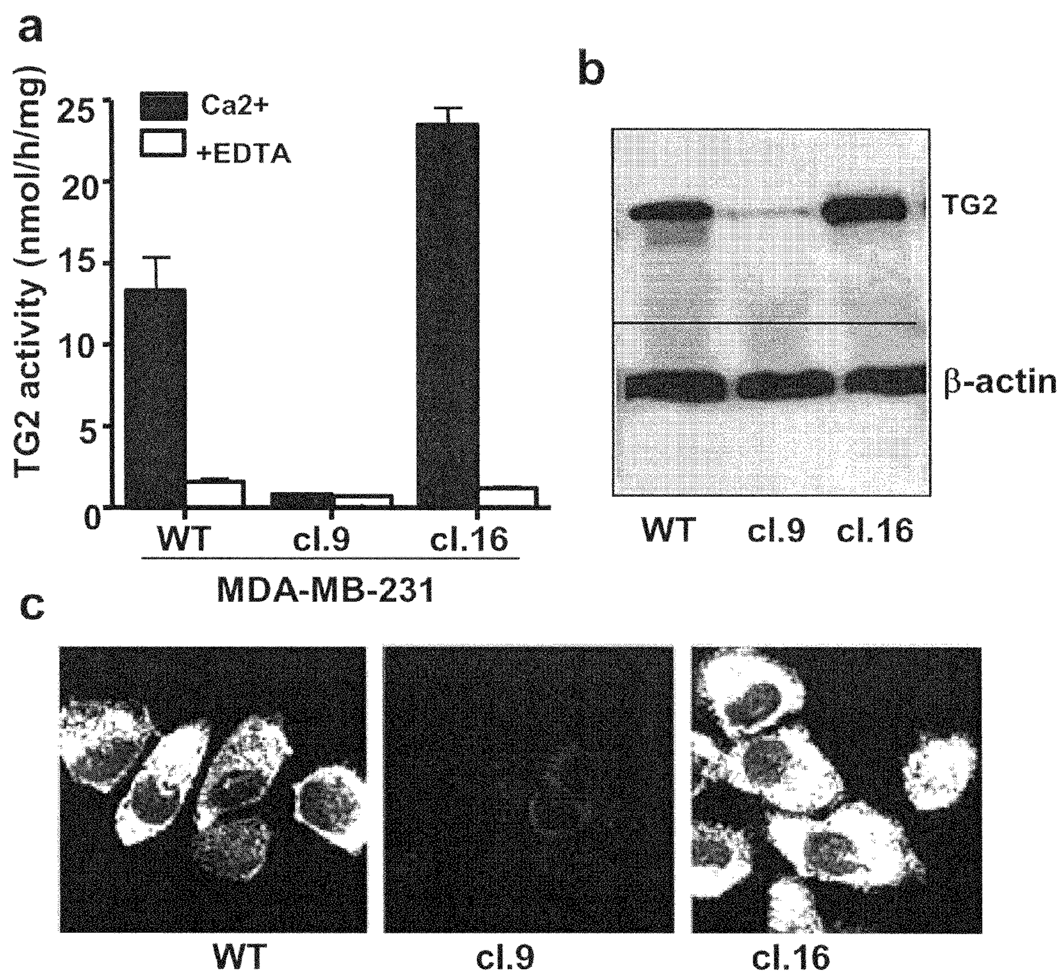

| | Positive | Negative | Total |
|---|---|---|---|
| Normal Ducts | 1 (11%) | 8 (89%) | 9 |
| PDAC | 51 (78%) | 14 (22%) | 65 |

A

B

| Gp | Mice no. | Spleen | Mensentry/ Omentum | Liver | Total | Metastasis Score |
|---|---|---|---|---|---|---|
| I | M1 | 3+ | 3+ | 1+ | 7 | 4.4 |
| | M2 | 2+ | 1+ | 0 | 3 | |
| | M3 | 2+ | 2+ | 0 | 4 | |
| | M4 | 1+ | 3+ | 0 | 4 | |
| | M5 | 2+ | 3+ | 0 | 5 | |
| II | M1 | 2+ | 3+ | 1+ | 6 | 4.6 |
| | M2 | 2+ | 3+ | 1+ | 6 | |
| | M3 | 2+ | 3+ | 1+ | 6 | |
| | M4 | 1+ | 3+ | 0 | 4 | |
| | M5 | 1+ | 0 | 0 | 1 | |
| III | M1 | 0 | 0 | 0 | 0 | 0.4 |
| | M2 | 1+ | 0 | 0 | 1 | |
| | M3 | 0 | 0 | 0 | 0 | |
| | M4 | 1+ | 0 | 0 | 1 | |
| | M5 | 0 | 0 | 0 | 0 | |
| IV | M1 | 1+ | 0 | 0 | 1 | 0.6 |
| | M2 | 0 | 0 | 0 | 0 | |
| | M3 | 1+ | 0 | 0 | 1 | |
| | M4 | 0 | 0 | 0 | 0 | |
| | M5 | 1+ | 0 | 0 | 1 | |

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 1
tatggccagt gctgggtctt cgcc 24

<210> SEQ ID NO 2
<211> LENGTH: 24

-continued

<212> TYPE: DNA
<213> ORGANISM: Artificial Sequence
<220> FEATURE:
<223> OTHER INFORMATION: Chemically synthesized primer

<400> SEQUENCE: 2
ggctccaggg ttaggttgag cagg 24

<210> SEQ ID NO 3
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 3
cgactctaga aacacaagag caaga 25

<210> SEQ ID NO 4
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 4
aaggttagct tactgtcaca cgctt 25

<210> SEQ ID NO 5
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 5
tgagagcaat gagcattcgg atg 23

<210> SEQ ID NO 6
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 6
cagggagttt ccatgaagcc ac 22

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 7
tcccatcagc tgcccagaaa 20

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 8
tgactcctgt gttcctgtta 20

<210> SEQ ID NO 9
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 9
agtatataca cttcagataa c 21

<210> SEQ ID NO 10
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 10 ccacctttc agccaacag 19

<210> SEQ ID NO 11
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 11
caactgcctg gtccagacc 19

<210> SEQ ID NO 12
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 12
cactctctgg cttcatgcc 19

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 13
agccaccacc gtccttccaa a 21

<210> SEQ ID NO 14
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 14
cctccgtccc caccccaaca t 21

<210> SEQ ID NO 15
<211> LENGTH: 22
<212> TYPE: DNA
<213> ORGANISM: Artificial Sequence
<220> FEATURE:
<223> OTHER INFORMATION: Chemically synthesized primer -continued

```
<400> SEQUENCE: 15

gaactgtgtt tgccgcctgg tc                                         22


<210> SEQ ID NO 16
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 16

gtcagctggg aatttgtccc tc                                         22


<210> SEQ ID NO 17
<211> LENGTH: 45
<212> TYPE: DNA
<213> ORGANISM: Artificial Sequence
<220> FEATURE:
<223> OTHER INFORMATION: Chemically synthesized sequence

<400> SEQUENCE: 17

ttgttacaag ggactttccg ctggggactt tccagggagg cgtgg                45


<210> SEQ ID NO 18
<211> LENGTH: 45
<212> TYPE: DNA
<213> ORGANISM: Artificial Sequence
<220> FEATURE:
<223> OTHER INFORMATION: Chemically synthesized sequence


<400> SEQUENCE: 18

ttgttacaac tcactttccg ctgctcactt tccagggagg cgtgg                45


<210> SEQ ID NO 19
<211> LENGTH: 21
<212> TYPE: DNA
<213> ORGANISM: Artificial Sequence
<220> FEATURE:
<223> OTHER INFORMATION: Chemically synthesized sequence


<400> SEQUENCE: 19

aaggcccgtt ttccactaag a                                          21


<210> SEQ ID NO 20
<211> LENGTH: 21
<212> TYPE: DNA
<213> ORGANISM: Artificial Sequence
<220> FEATURE:
<223> OTHER INFORMATION: Chemically synthesized sequence

<400> SEQUENCE: 20

aagggcgaac cacctgaaca a                                          21
```

METHODS FOR TREATING CANCER TARGETING TRANSGLUTAMINASE

CROSS REFERENCE TO RELATED APPLICATIONS

This application claims the benefit of U.S. Provisional Application Ser. No. 60/852,800 filed Oct. 18, 2006, which is incorporated by reference herein.

STATEMENT OF GOVERNMENT INTEREST

This disclosure was made with support under grant numbers U54 RFA CA096300 and CA92115 awarded by the National Cancer Institute, and grant numbers CA092115, CA98823, and CA098823 awarded by the National Institute of Health. The government has certain rights in the invention.

SEQUENCE LISTING

This disclosure includes a sequence listing submitted as a text file pursuant to 37 C.F.R. §1.52(e)(v) named replacementsequencelisting.txt, created on Jun. 18, 2008, with a size of 4,110 bytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

BACKGROUND

Tissue transglutaminase (TG2, EC 2.3.2.13) is a unique member of the transglutaminase family of enzymes. In addition to catalyzing $Ca^{2+}$-dependent posttranslational modification of proteins by inserting irreversible ϵ(γ-glutamyl) lysine crosslinks between substrate proteins, it can catalyze calcium-independent hydrolysis of guanosine 5'-triphosphate (GTP), the protein disulfide isomerase reaction, and serine/threonine kinase activity. TG2's ability to hydrolyze GTP enables it to serve as a signaling molecule and activates a downstream target, phospholipase C. Although, predominantly a cytosolic protein, TG2 can also be secreted outside the cell where it regulates cell-matrix interactions; can translocate to the nucleus where it associates with pRb, p53, and histones to regulate certain cellular functions; and can be expressed on the cell membrane in association with β-integrins where it serves as a coreceptor for integrin-mediated binding to fibronectin (Fn). Cell surface TG2 can affect important cell functions such as attachment, spreading, motility, and survival.

Involvement of TG2 in apoptosis has been well established; overexpression of TG2 results in either spontaneous apoptosis of cells or rendering cells highly sensitive to apoptosis-inducing agents. In contrast with this, recent evidence indicates that increased expression of TG2 may prolong cell survival by preventing apoptosis. Several reports have documented elevated expression of TG2 in various cancer types. We and others have reported that the basal expression of TG2 in several tumor cells and tumor cell lines is elevated when they become resistant to chemotherapeutic drugs. Importantly, the increased TG2 expression was associated with an increased resistance to chemotherapeutic drugs and other apoptosis-inducing stimuli. Inhibition of TG2 by small interfering RNA (siRNA) reversed the sensitivity of drug-resistant MCF-7 breast cancer cells to doxorubicin and rendered them sensitive to serum-withdrawal-induced apoptosis. Tumor cells from metastatic sites and cell lines with metastatic potential also have been found to express high basal levels of TG2. Elevated expression of TG2 in pancreatic cancer cells has been detected by conventional methods and cDNA microarrays. These findings suggest that TG2 expression plays a role in the development of drug resistance and metastatic phenotypes in cancer cells. However, no direct link between TG2, drug resistance, and metastasis has been established, and the molecular pathways that result in constitutive expression of TG2 in cancer cells remain elusive.

Like the expression of TG2, expression of the PKCδ isoform is associated with the metastatic phenotype in some cancers. Protein kinase C (PKC) plays a central role in signal transduction pathways that mediate the action of growth factors, tumor promoters and cellular oncogenes. The tumor promoter phorbol ester results in the activation of PKC and can either promote or inhibit the growth of human pancreatic cancer cells. Similarly, phorbol ester can induce TG2 expression in various cell types. Depending on the cell type, PKCδ can function as a tumor suppressor, proapoptotic factor, or anti-apoptotic factor and can regulate cell proliferation and cell survival functions.

SUMMARY

This present disclosure concerns TG2 whose expression is aberrantly upregulated in drug-resistant and metastatic tumors. The expression of TG2 in cancer cells is associated with increased resistance to anticancer drugs and gain of invasive functions. Conversely, downregulation of endogenous TG2 is associated with reversal of the drug resistance and metastatic phenotypes. PDAC cells and lines that exhibit profound intrinsic resistance to anticancer therapies contained high basal levels of TG2 protein. Similarly, several other cancer types (e.g., breast, melanoma, and ovarian) selected for resistance or isolated from metastatic sites contained elevated levels of TG2 expression. Accordingly, the present invention provides methods for treating cancer comprising downregulating TG2 expression.

We have tested several cancer cell types (breast, melanoma, pancreatic, ovarian) and linked TG2 expression with drug resistance and metastatic phenotypes. We have shown that ectopic expression of TG2 results in increased invasion of cancer cells through the Matrigel, strong attachment to ECM-coated surfaces, increased resistance to apoptosis, and activation of cell survival signaling pathways. Conversely, downregulation of TG2 by siRNA or its inhibition by pharmacologic agents inhibited the invasion of cancer cells though the matrigel, reversal of drug resistance, increased sensitivity to stressors and spontaneous death of cells via autophagy. We have confirmed these observations in patients' tumor samples as well. For example, Kaplan-Meier curve showed a strong correlation between patient survival and TG2/PTEN expression. Similarly, knock down of TG2 in a PDAC cells caused strong retardation in xenograft growth in nude mouse model.

Our results revealed that TG2 expression promotes cell survival and invasive functions in cancer cells by associating and constitutively activating several key regulatory proteins. For example, TG2 by associating with beta-1, -3, -4, and -5 members of the integrin family of proteins could promote stable interaction of cells with the extracellular matrix ligands resulting in activation of cell survival pathways. Similarly, TG2 expression led to constitutive activation of the nuclear transcription factor, NF-κB as a result of its binding to the p65 subunit of NF-κB. Thirdly, TG2 expression resulted in constitutive activation of the focal adhesion kinase (FAK) and its downstream PI3K/Akt cell survival signaling pathways by associating with FAK protein. Importantly, TG2 expression in cancer cells effectively downregulated the expression and function of the tumor suppressor PTEN protein. The drugs currently used for treating cancer cells generally inhibit or target single protein or pathways. Inhibition of TG2 expression, therefore, is likely to inhibit/block simultaneously various pathways (integrin-mediated, FAK, NF-κB, and PTEN-dependent) that are critical for the successful survival of cancer cells.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

The patent or application file contains at least one drawing executed in color. Copies of this patent or patent application publication with color drawings) will be provided by the Office upon request and payment of the necessary fee.

FIG. 1 shows TG2 expression in the parental and two subclones of MDA-MB231 cells. (a) Enzymatic activity of TG2 was determined in the cell extract by studying $Ca^{2+}$-dependent incorporation of $[^3H]$putrescine into dimethylcasein, as described in Materials and Methods. Results shown are means±s.d. of six values from two independent experiments. (b) TG2 expression was also determined by Western blotting using the anti-TG2 monoclonal antibody CUB74 as a probe. The nitrocellulose membrane was stripped and reprobed with an anti-b-actin antibody to ensure even loading of lanes. (c) Immunofluorescence microscopy images of the parental (WT), cl. 9 and cl. 16 MDA-MB231 cells immunostained with TG2-specific anti-IgG1.

Figure 2:
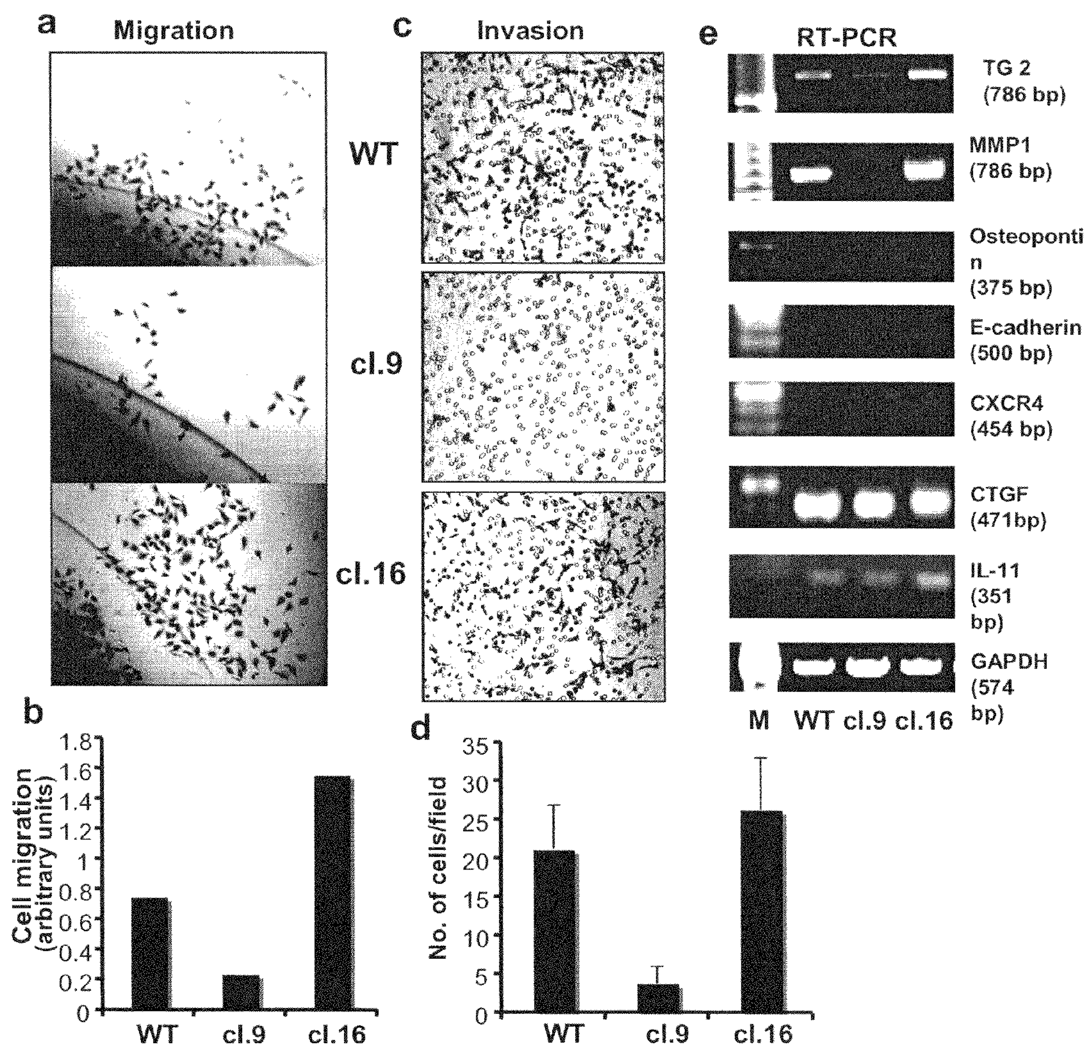

FIG. 2 shows TG2 expression is associated with increased migration and invasion. (a) A small droplet of agarose containing 103 WT, cl. 9 or cl. 16 MDA-MB231 cells was seeded onto the Fn-coated Petri dish, after which cells were allowed to migrate out from the droplet for 48 h at 37° C. Migrated cells were fixed, stained, and photographed as described in Materials and Methods. (b) Parental (WT) and two subclones (cl. 9 and cl. 16) of MDA-MB23 1 cells were compared for their invasive functions in a Matrigel-transwell assay system. Representative fields of cells that migrated under the membrane through the Matrigel were photographed. (c) Expression of TG2 and various metastasis-related gene transcripts was studied by RT-PCR in parental (WT) and two subclones (cl. 9 and cl. 16) of MDAMB23 1 cells. An amplification product of the glyceraldehyde-3-phosphate dehydrogenase housekeeping gene was used as a loading control. M, molecular weight markers.

Figure 3:
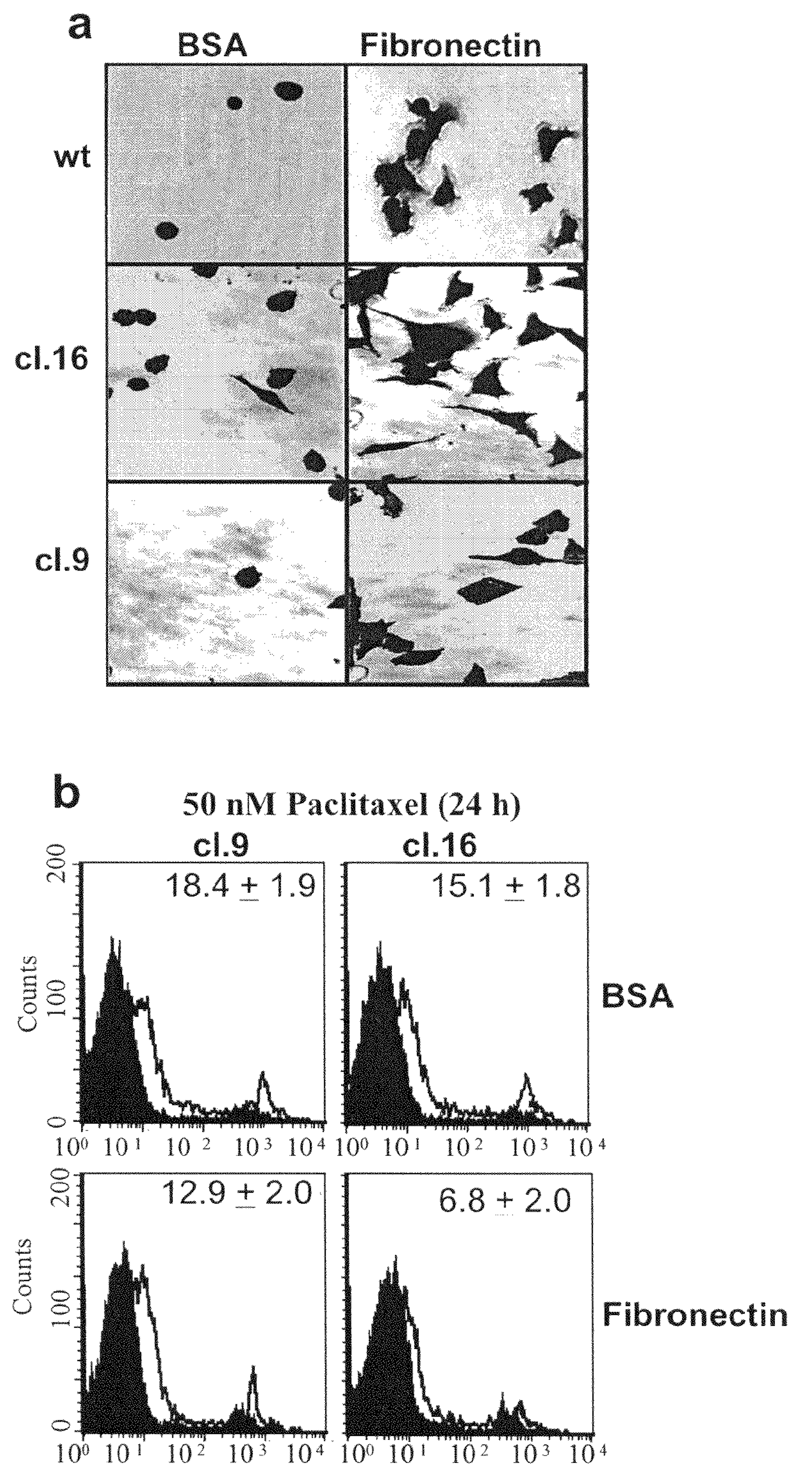

FIG. 3 shows TG2 expression promotes cell attachment and cell survival functions in MDA-MB23 1 cells. (a) Low TG2-expressing (cl. 9) and high TG2-expressing (cl. 16) cells were seeded in BSA- or Fn-coated 96-well plates (2~104 cells/well/0.2 ml of serum-free medium). After a 1-h incubation, cells were analysed for attachment after washing and staining with crystal violet, as described in Materials and Methods. Results shown are from a representative experiment repeated four times with similar results. (b) Low TG2-expressing (cl. 9) and high TG2-expressing (cl. 16) MDA-MB231 cells were cultured on BSA- or Fn-coated plates in the presence or absence of 50 nM paclitaxel. After a 24-h treatment, cells were harvested and analysed for apoptosis using the ApoAlert Annexin kit, as described in Materials and Methods. Results shown are from a representative experiment repeated at least two times with less than 15% s.d.

Figure 4:
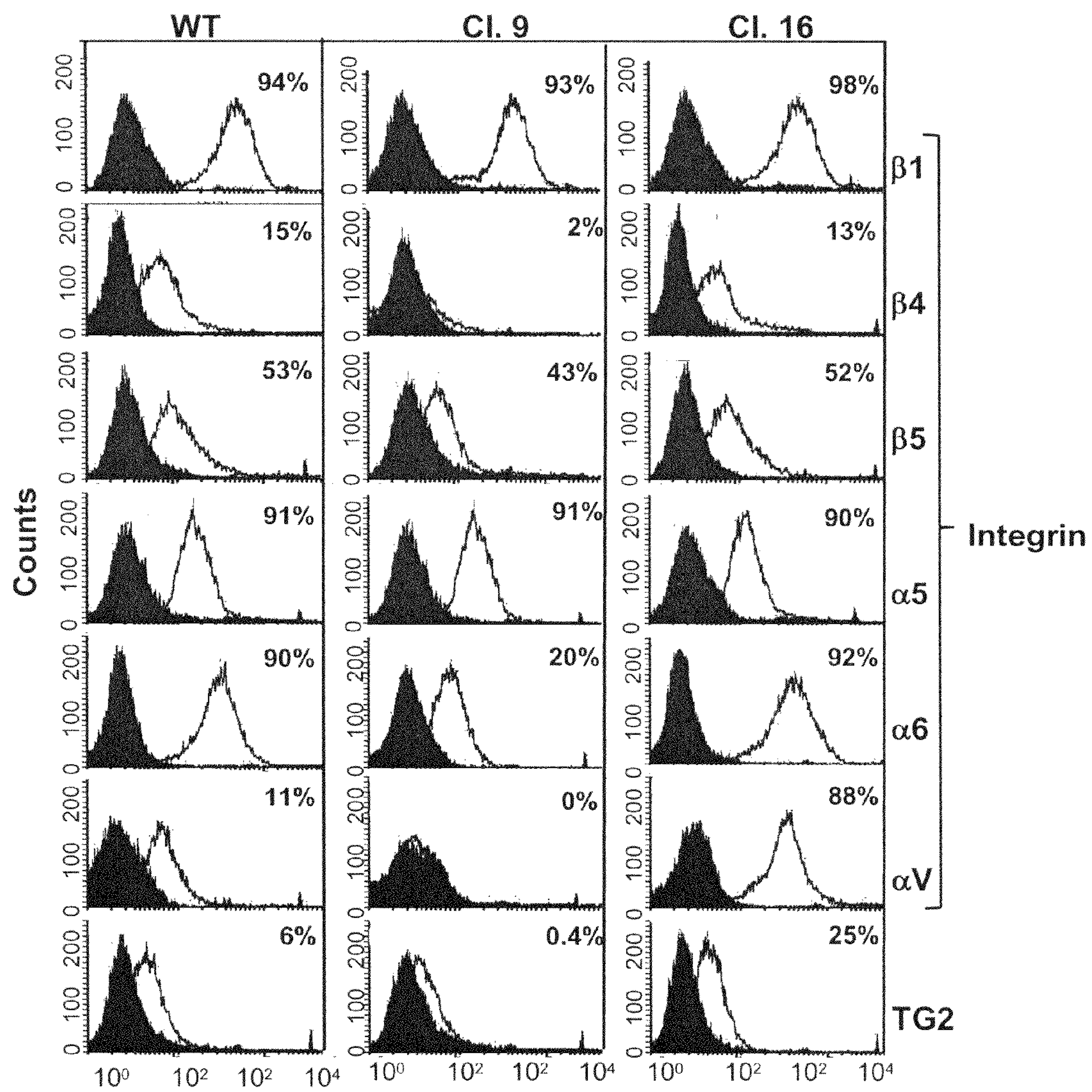

FIG. 4 shows expression of TG2 and integrins on the surface of MDA-MB23 1 cells. Flow cytometric analysis was used to determine the cell-surface expression of integrins β1, β4, β5, α5, α6, and αv and of the TG2 protein. The filled curves show the fluorescence intensity of cells incubated with isotypic control IgG. The open curves show the fluorescence intensity of the indicated integrin or TG2, as revealed by the immunostaining of cells with a specific antibody, followed by the fluorochrome Alexa 488-conjugated secondary antibody.

Figure 5:
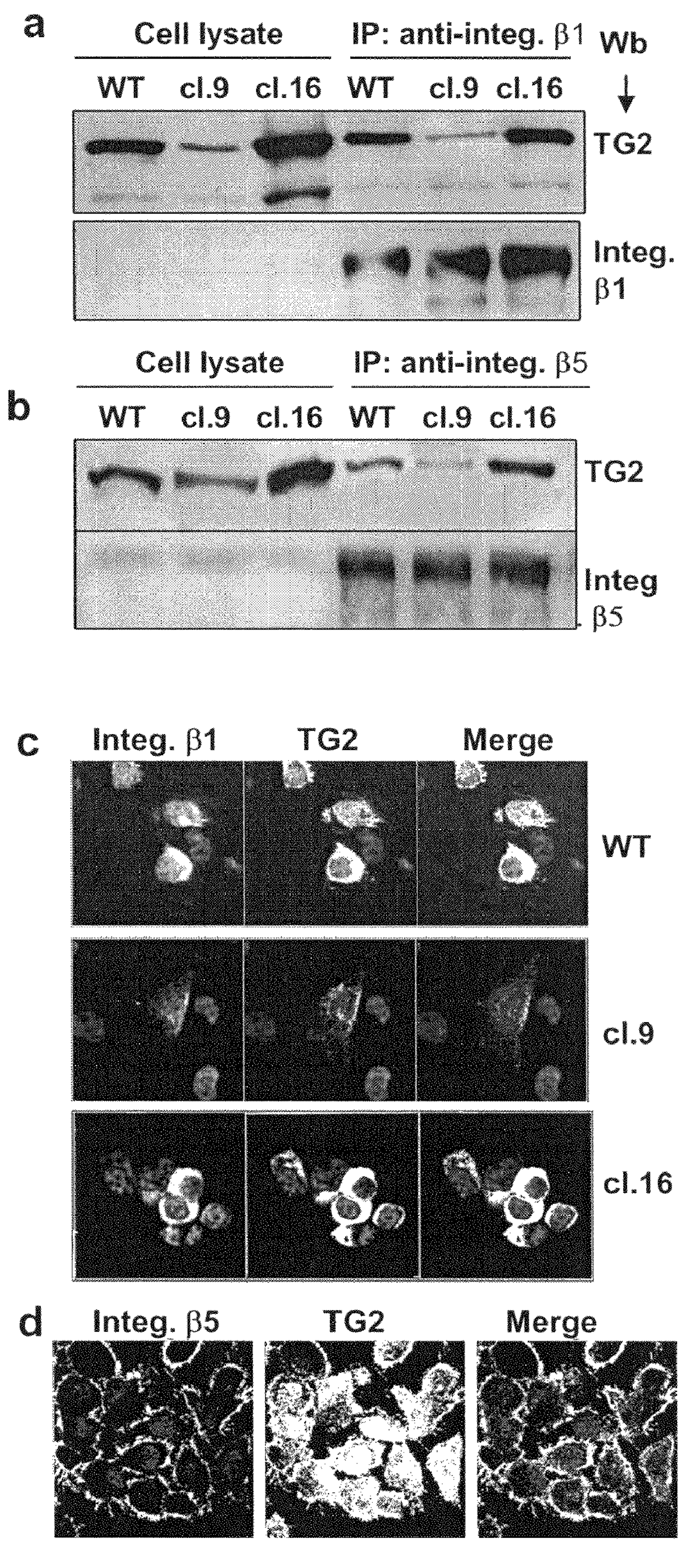

FIG. 5 shows TG2 closely associates with integrins β1 and β5 in MDA-MB23 1 cells. Cell extracts (each with 400 mg of protein) from the parental (WT) and two subclones (cl. 9 and cl. 16) of MDA-MB231 cells were immunoprecipitated with anti-β1-(a) or anti-β5-(b) integrin antibodies. IP and total cell lysate (30 mg of protein) from the WT, cl. 9 and cl. 16 MDA-MB231 cells were subjected to immunoblotting and probed with an anti-TG2 antibody. The membranes were then stripped and reprobed with either anti-β1 (right side of panel a) or anti-β5 (right side of panel b) antibodies. (c) WT, cl. 9 and cl. 16 MDA-MB231 cells were incubated with anti-TG2- and anti-β1-integrin antibodies, followed by Alexa 546-tagged anti-rabbit IgG (red) and Alexa 488-tagged anti-mouse IgG (green) antibodies. The stained cells were mounted on glass slides and viewed under a Zeiss laser-scanning microscope for imaging.

Figure 6:
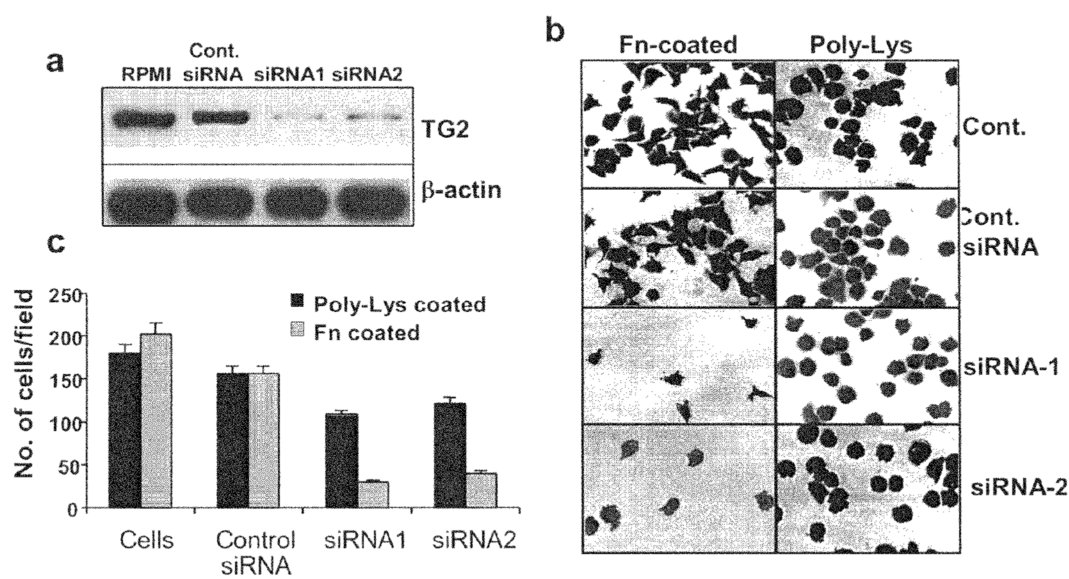

FIG. 6 shows attachment of MDA-MB231 cells to Fn is mediated by TG2. (a) High TG2-expressing MDA231/cl. 16 cells were transfected with TG2-specific siRNAs (siRNA1 and siRNA2) or control (cont.) siRNA (scrambled). After 48 h, cells were harvested and analysed for TG2 expression. (b) Control and siRNA-transfected MDA231/cl. 16 cells were seeded in Fn-coated or polylysine (Poly-Lys)-coated 96-well plates in serum-free medium. After a 1-h incubation, non-adherent cells were removed by washing. Adherent cells were fixed, stained and examined under a light microscope. (c) The number of adherent cells was then counted in five random fields, and the average numbers of cells per field was plotted.

Figure 7:
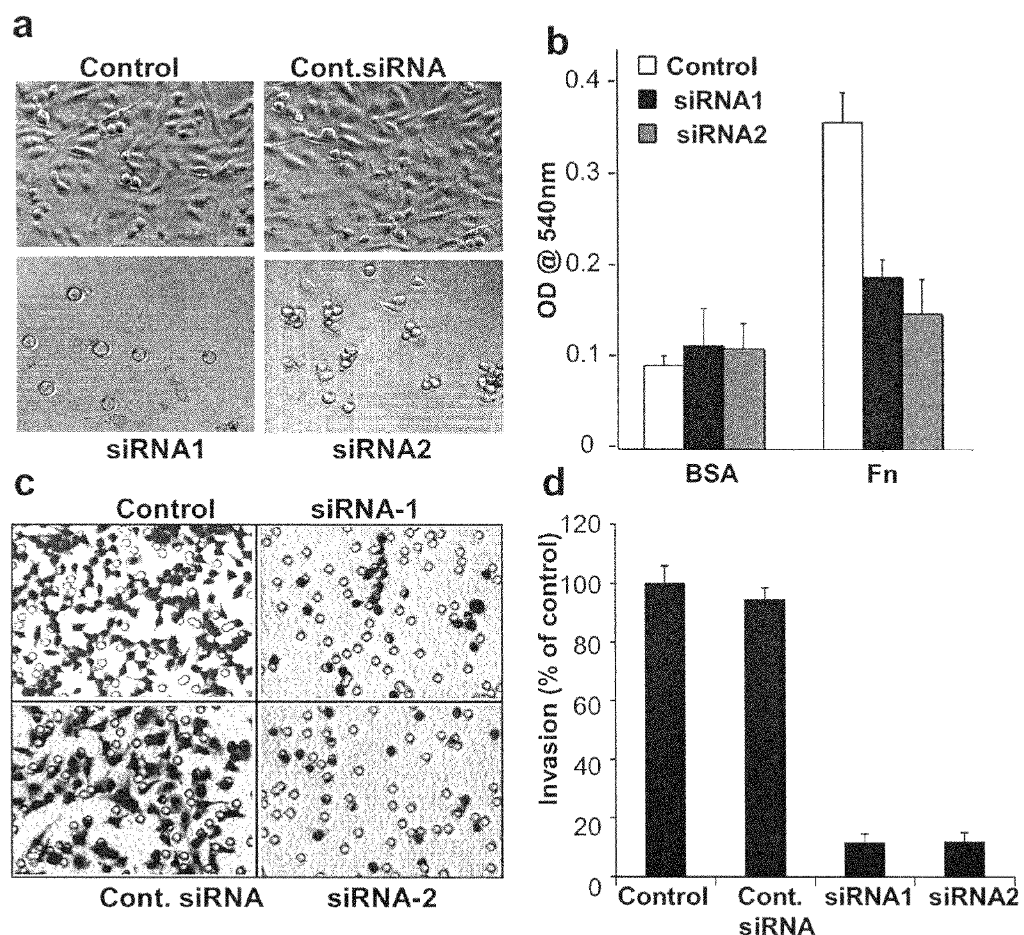

FIG. 7 shows cell survival and invasion of MDA-MB 231 cells is mediated by TG2. Control and siRNA-transfected MDA231/cl. 16 cells were incubated in serum-free medium in Fn- or BSA-coated plates. After a 48-h culture, cells were examined under the light microscope (a) or analysed for cell viability by MTS assay (b). (c) Control and siRNA-transfected MDA231/cl. 16 cells were compared for invasion through Matrigel-transwell membranes. Representative fields with cells that migrated were photographed. (d) Ten fields were counted randomly under the microscope, and the number of cells that had invaded through the Matrigel-transwell membranes were plotted as percentages of untreated control cells that had migrated under similar conditions.

Figure 8:
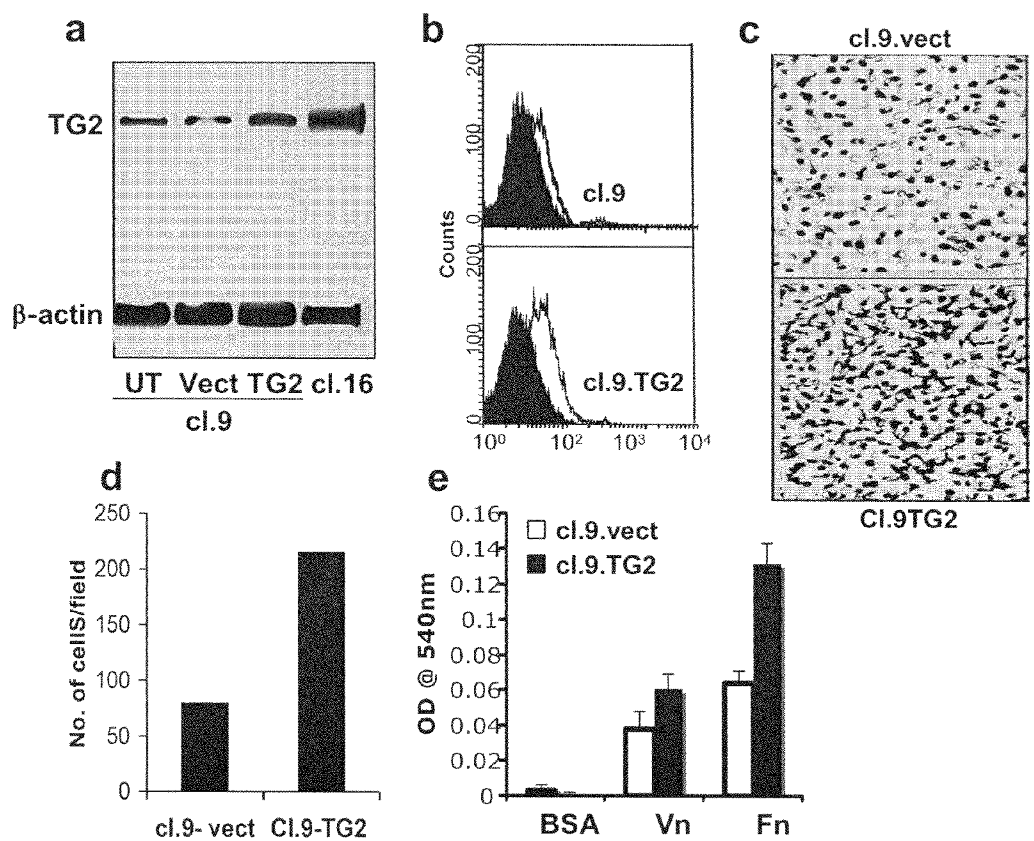

FIG. 8 shows TG2 expression results in increased invasion and cell attachment. (a) Western blot analysis showing basal expression of TG2 in MDA-231/cl. 9 cells (UT) and after their infection with adenovirus containing full-length TG2 construct (TG2). Cells infected with adenovirus alone (vect) and MDA231/cl. 16 cells served as control. The membranes were stripped and resorbed with anti-β-actin antibody to determine even loading of proteins in each lane. (b) Cell surface expression of TG2 in untreated (cl. 9) and TG2-infected (cl. 9-TG2)

MDA-231/cl. 9 cells as determined by flow cytometry. (c) Number of MDA-231/cl. 9 cells that invaded through the Matrigel-transwell transmembrane after their infection with adenovirus alone (vect) or adenovirus containing TG2 cDNA construct (TG2) was determined and mean of number of cells counted from 10 random microscopic fields were plotted (d). (e) MDA-231/cl. 9 cells infected with adenovirus alone (vect) to adenovirus-containing TG2 (TG2) cDNA were compared for their ability to attach to the BSA-, vitronectin (Vn)-, or Fn-coated plates. The results shown are the mean of four values±s.d.

Figure 9:
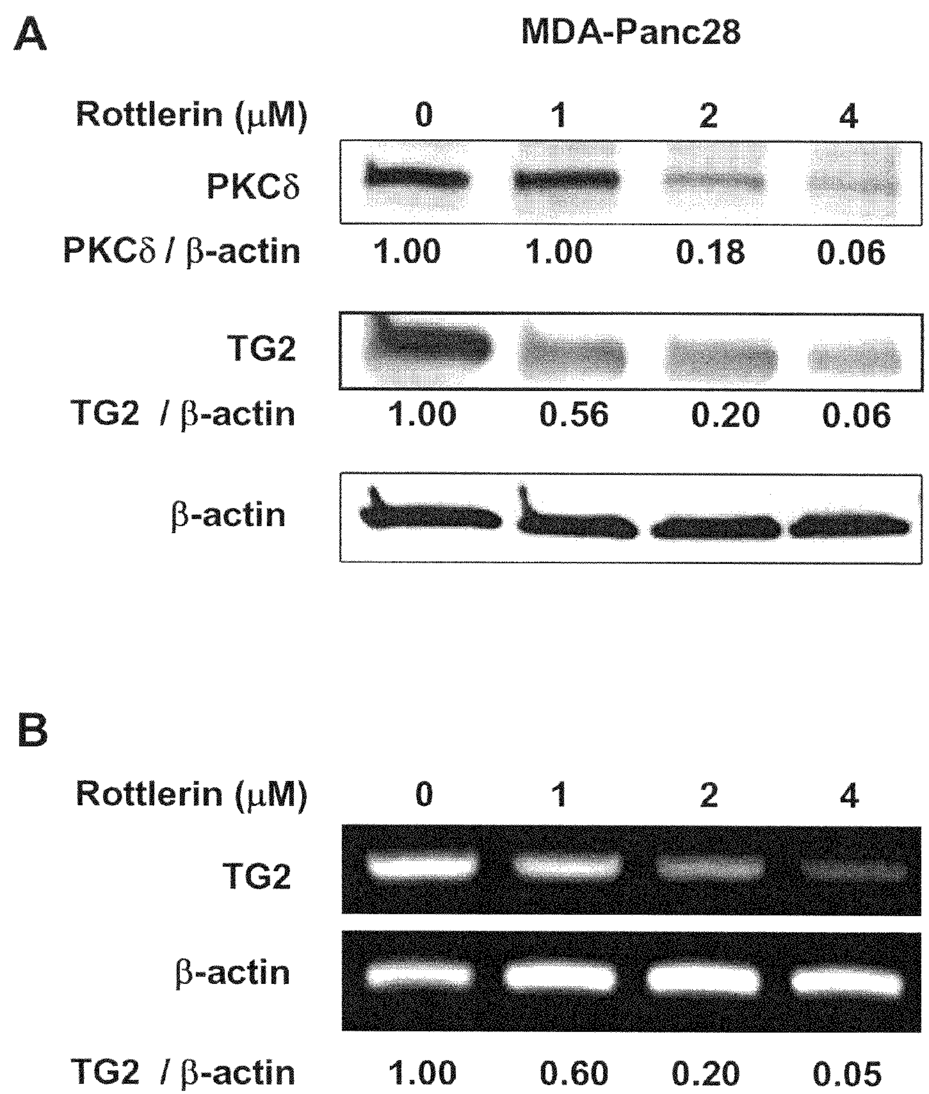

FIG. 9 shows Rottlerin inhibits both PKCδ and TG2 in MDA-Panc28 cells. (A) Cells at 80% confluence were treated with 1 μM, 2 μM or 4 μM rottlerin. After 48 h of treatment, the cells were lysed and cell lysates were fractionated by sodium dodecyl sulfate polyacrylamide gel electrophoresis (SDS-PAGE) and transferred onto nitrocellulose membrane to determine PKCδ and TG2 protein expression by western blot analysis. The membrane was stripped and reprobed with an anti-β-actin antibody to confirm equal loading of protein in each lane. (B) Total RNA was extracted, and transcript levels of TG2 and β-actin were determined by RT-PCR analysis as described in Materials and Methods. Relative expression levels were determined by densitometry as compared with β-actin. Experiments were repeated at least three times.

Figure 10:
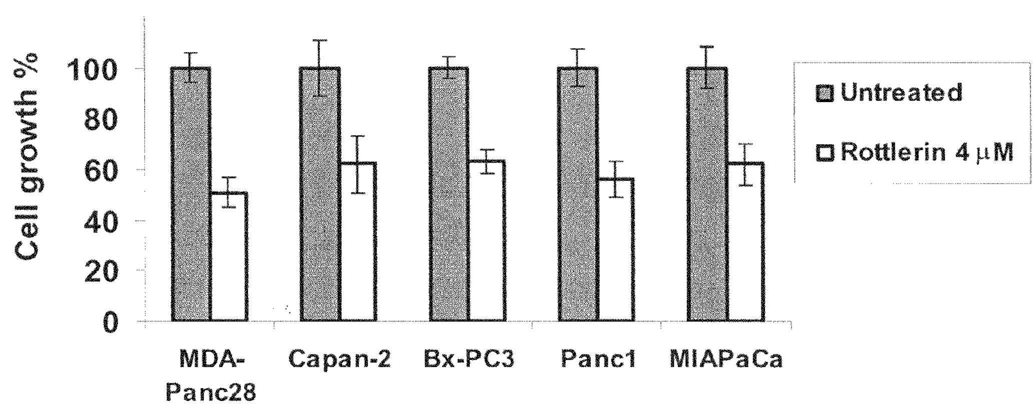
Figure 10:
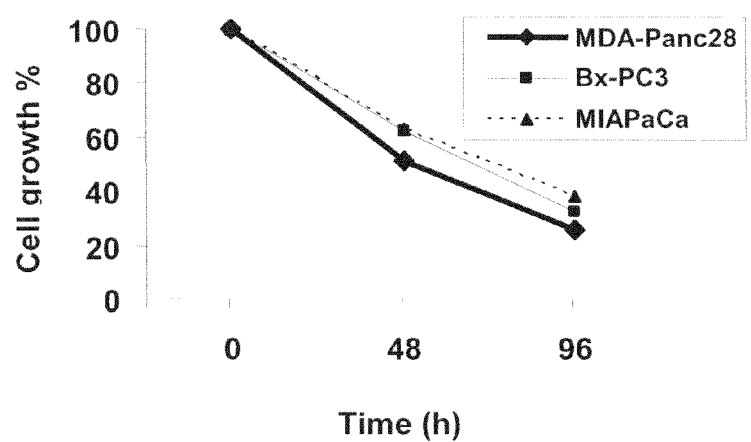

FIG. 10 shows Growth inhibition by rottlerin in pancreatic cancer cells. (A) Different pancreatic cancer cell lines were treated with rottlerin (4 μM) for 48 h, and viable cells were detected by proliferation assay using Alamar Blue staining. Bars represent growth inhibition after normalizing untreated cells to 100%. (B) Growth of the indicated cell lines after treatment with rottlerin (4 μM) for 48 and 96 h.

Figure 11:
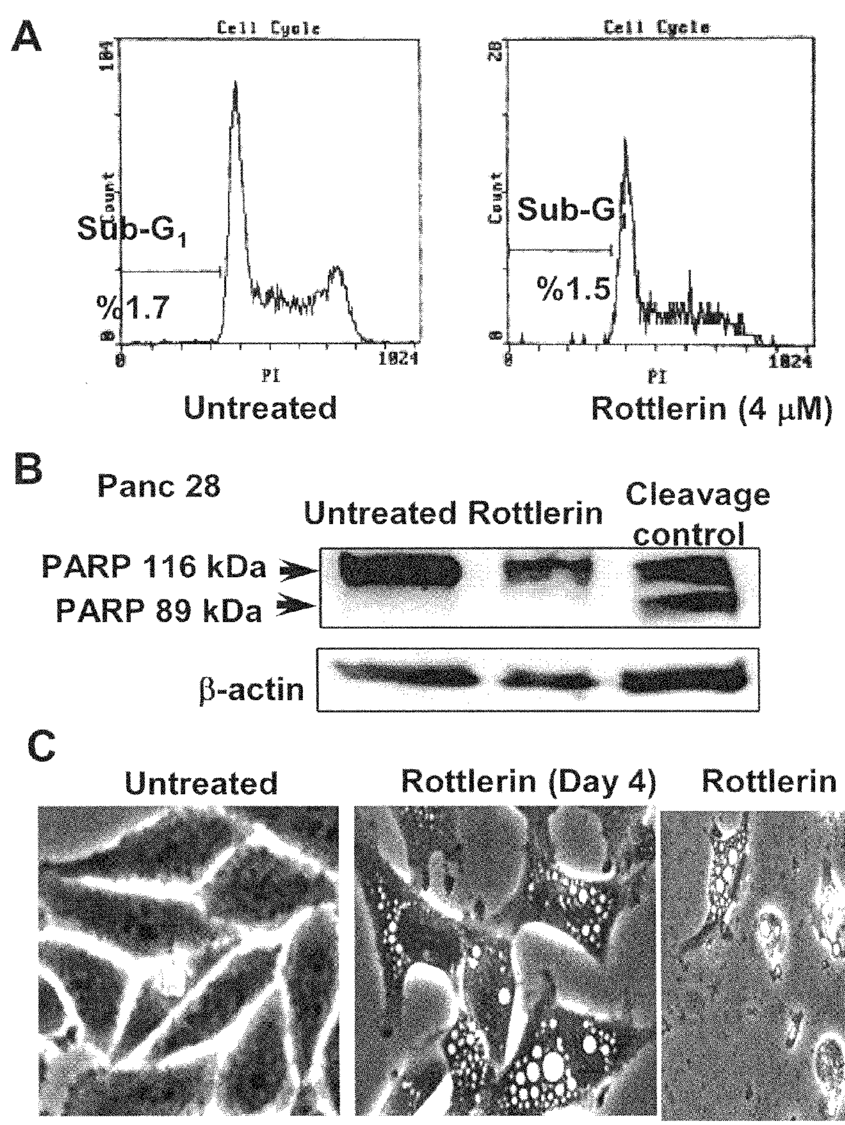

FIG. 11 shows Rottlerin did not induce apoptosis. (A) FACS analysis of the sub-G1 population in MDA-Panc28 cells showed that treatment with 4 μM rottlerin for 48 h did not cause cells to accumulate in this phase, indicating a lack of apoptosis. (B) Rottlerin did not induce PARP cleavage by Western blot analysis. PARP cleavage positive cell lysate was used as a positive control. (C) Morphological changes after treatment with rottlerin. Microphotographs were taken using a phase-contrast microscope (300× magnification). Left panel, untreated cells at 48 h of treatment; center panel, cells treated for 48 h, and right panel, cells treated for 96 h.

Figure 12:
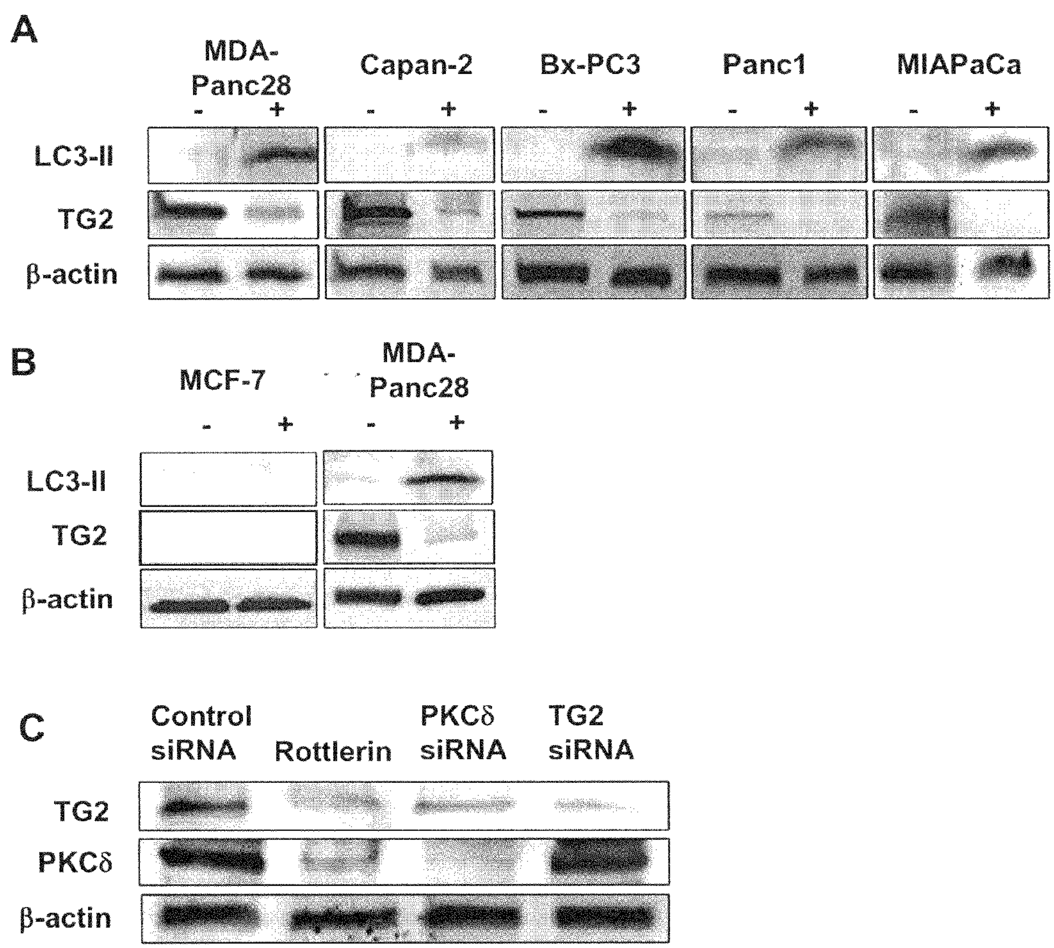
Figure 12:
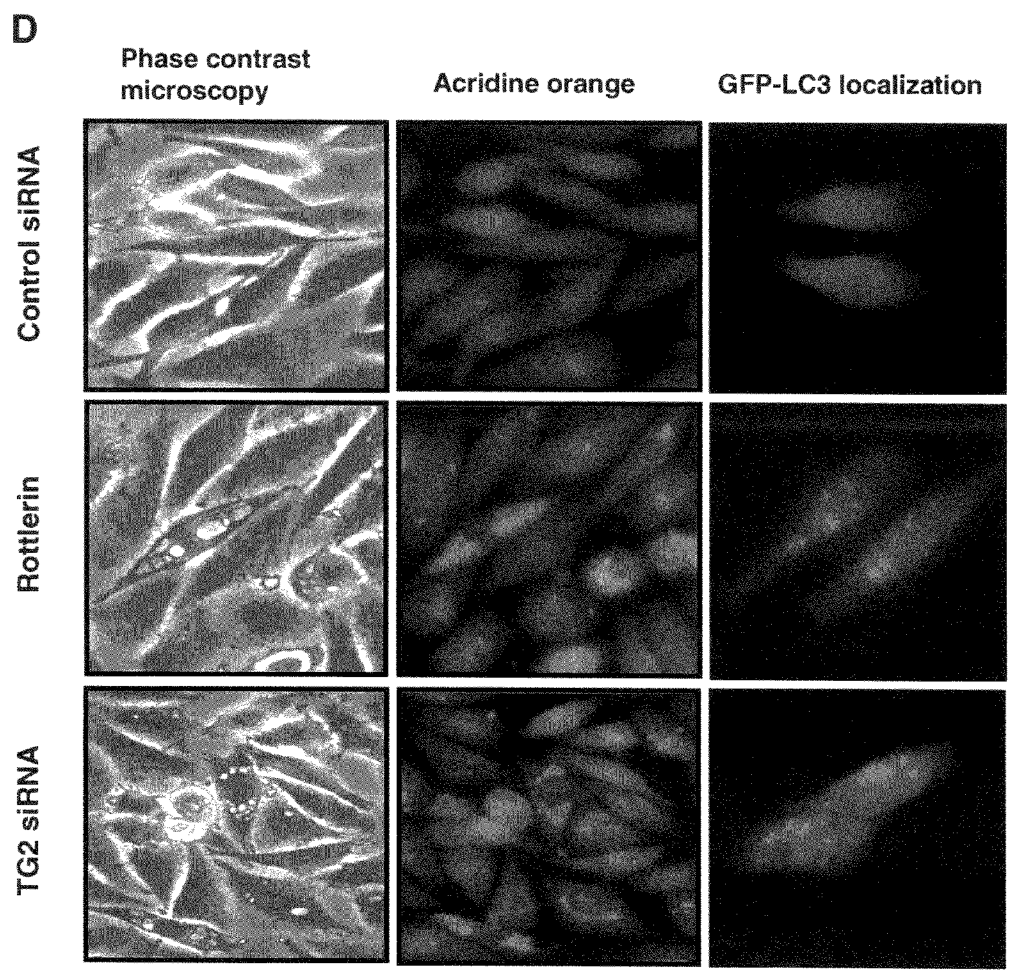
Figure 12:
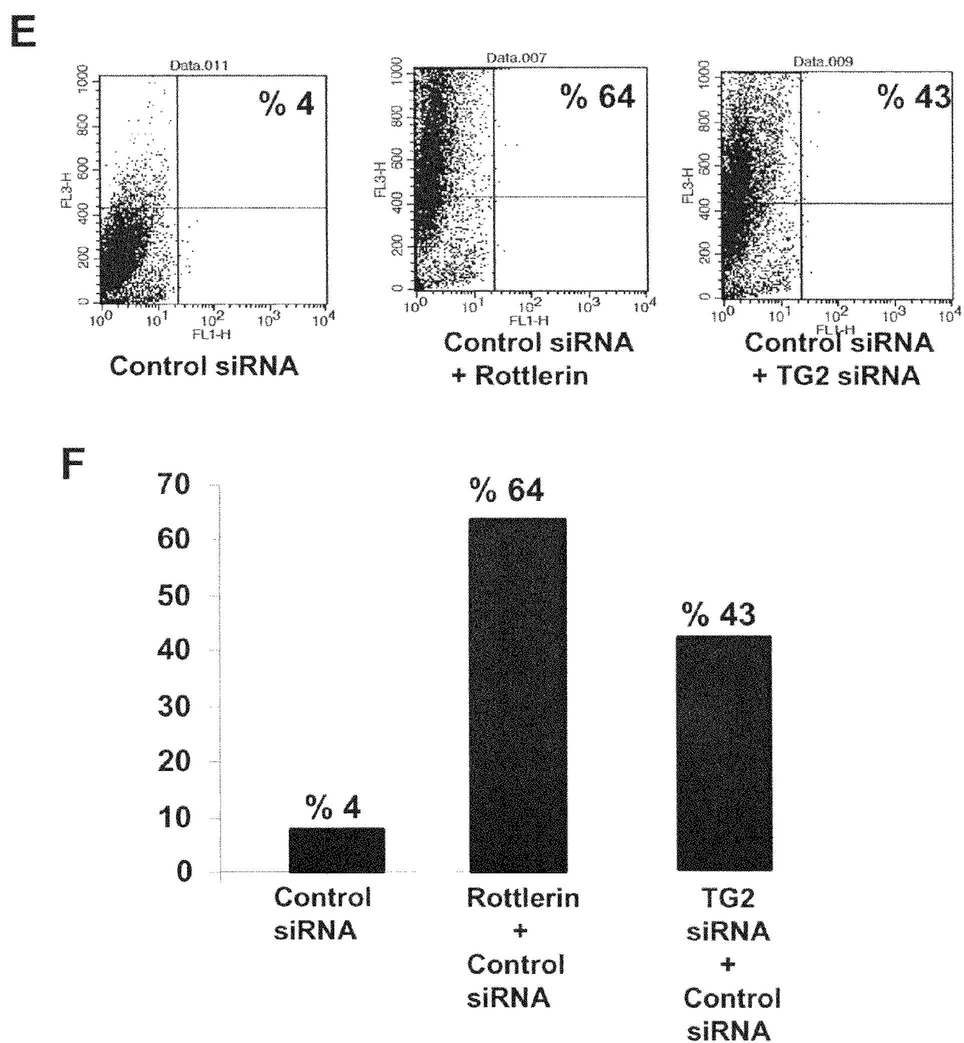

FIG. 12 shows Induction of autophagy in pancreatic cancer cells. (A) A panel of pancreatic cancer cell lines including MDA-Panc28, Capan-2, Bx-PC3, Panc1 and MIAPaCa cells were treated with Rottlerin (4 μM) for 48 h for the detection of LC3-II and TG2 expression by western blot. (B) MCF-7 cell line was also tested for LC3-II and TG2 expression by western blot. (C) Expression of TG2 in MDA-Panc28 cells was determined upon exposure to different treatments (D) Detection of autophagolysosomes; MDA-Panc28 cells were treated with either control siRNA, Rottlerin or TG2 siRNA for 48 h. Photomicrographs show morphological changes of the cells by phase contrast microscopy (left panels); acridine orange staining of the acidic vesicular organelles by fluorescent microscopy (center panels) and the localization LC3-II at autophagosomes in cells after transfection with GFP-LC3 plasmid (right panels). (E, F) Detection of acidic vesicular organelles by acridine orange staining in cells using FACS analysis. Green fluorescence intensity indicates cytoplasm and nucleus, while red color intensity shows acidic vesicular organelles.

Figure 13:
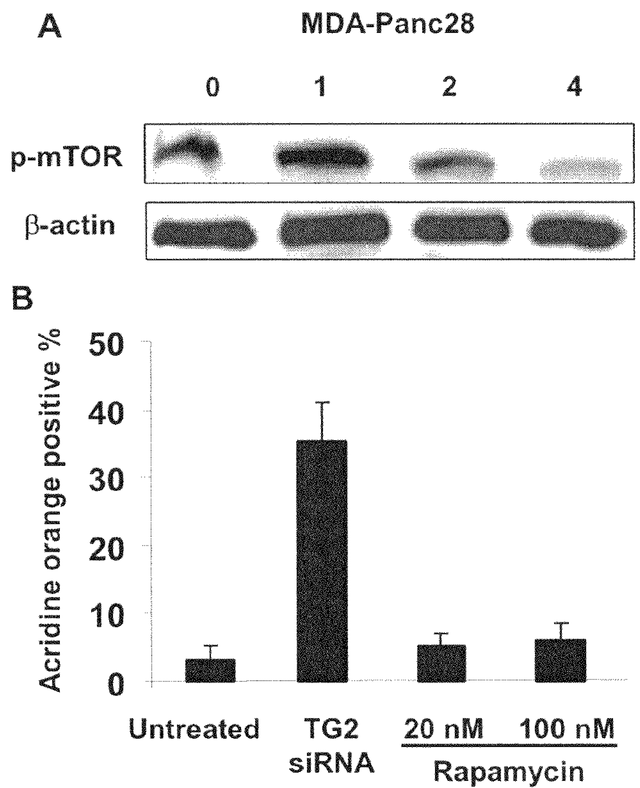

FIG. 13 shows Rottlerin inhibits mTOR activity in the MDA-Panc28 cancer cell line but does not induce autophagy via the mTOR pathway. (A) Phosphorylated mTOR was detected after 48 h of treatment with various doses of rottlerin, cells were subjected to western blot analysis. Phosphorylation of mTOR was inhibited in a dose-dependent manner. (B) MDA-Panc28 cells were treated with a specific mTOR inhibitor, rapamycin (at either 20 nM or 100 nM), TG2 siRNA or left untreated. FACS analysis of cells stained with acridine orange to detect acidic vesicular organelles demonstrated that rapamycin had no effect on autophagy, indicating that cell death was not induced via the mTOR pathway.

Figure 14:
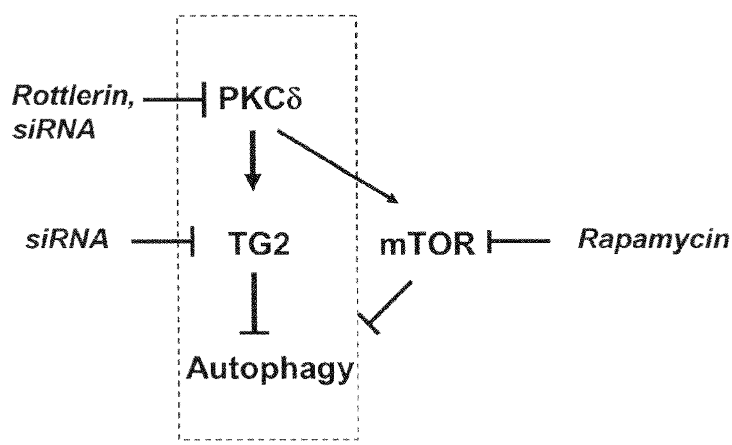

FIG. 14 shows Model for the role and regulation of TG2 by PKC in pancreatic cancer cells. PKCδ plays a role in the constitutive expression of TG2. Expression of TG2 plays an important role in preventing pancreatic cancer cells from undergoing autophagy Activation of mTOR pathway inhibits autophagy in some tumor cell lines but not in pancreatic cancer cells. Dashed line suggests the events taking place in pancreatic cancer cells.

Figure 15:
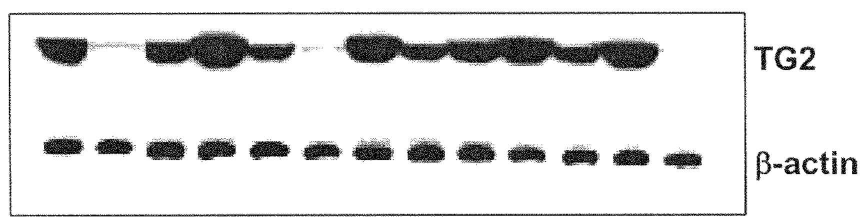
Figure 15:
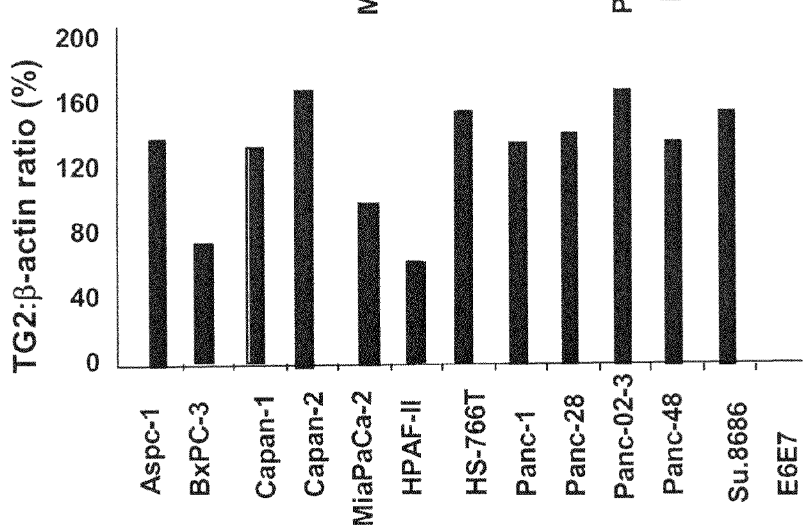

FIG. 15 shows TG2 expression in PDAC cell lines. Western blot (A) and its densitometry analysis (B) showing basal expression of TG2 protein in 12 PDAC cell lines and one immortalized normal pancreatic epithelial cell line (E6E7). Cell lines with TG2:β-actin ratio of >100% and <100% were considered high- and low-TG2 expressing cell lines, respectively.

Figure 16:
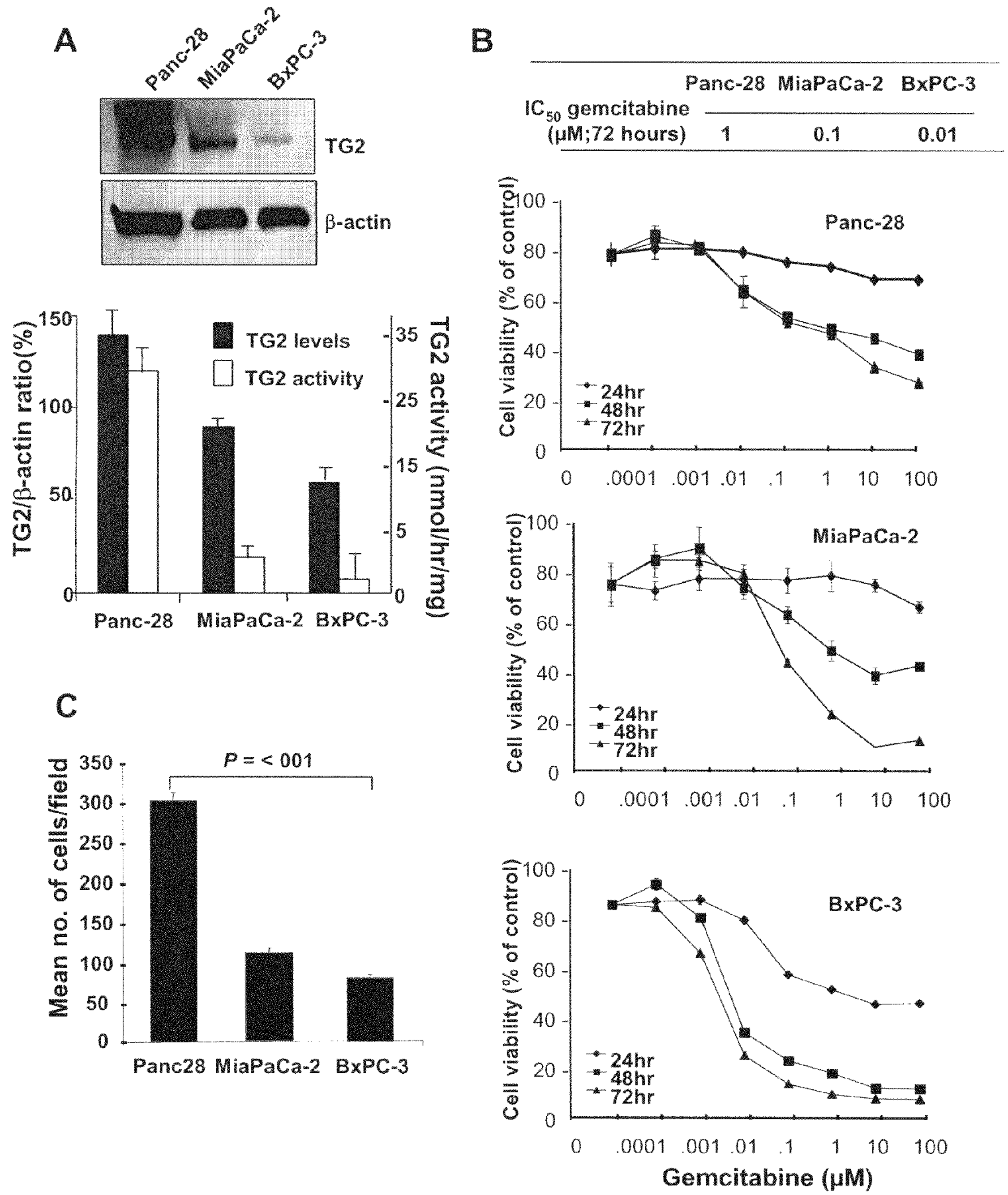

FIG. 16 shows TG2 expression is associated with gemcitabine resistance and invasive potential in PDAC cell lines. A, Western blot analysis comparing the basal expression of TG2 in three PDAC cell lines. The enzymatic activity (histograms) in three cell lines correlated with TG2 protein levels. (B) The cell viability, as determined by an MTS assay, of Panc-28, MiaPaCa-2, and BxPC-3 cells after their treatment with increasing doses of gemcitabine for 24, 48, or 72 hours. The $IC_{50}$ of gemcitabine for the cell lines after 72 hours is shown. (C) The invasive functions of the three cell lines, as determined by their ability to invade through Matrigel-Transwell membranes, was compared as described in Materials and Methods. Representative experiments done at least two times with similar results. Columns and line graphs, mean of quadruplicate values; bars, SD.

Figure 17:
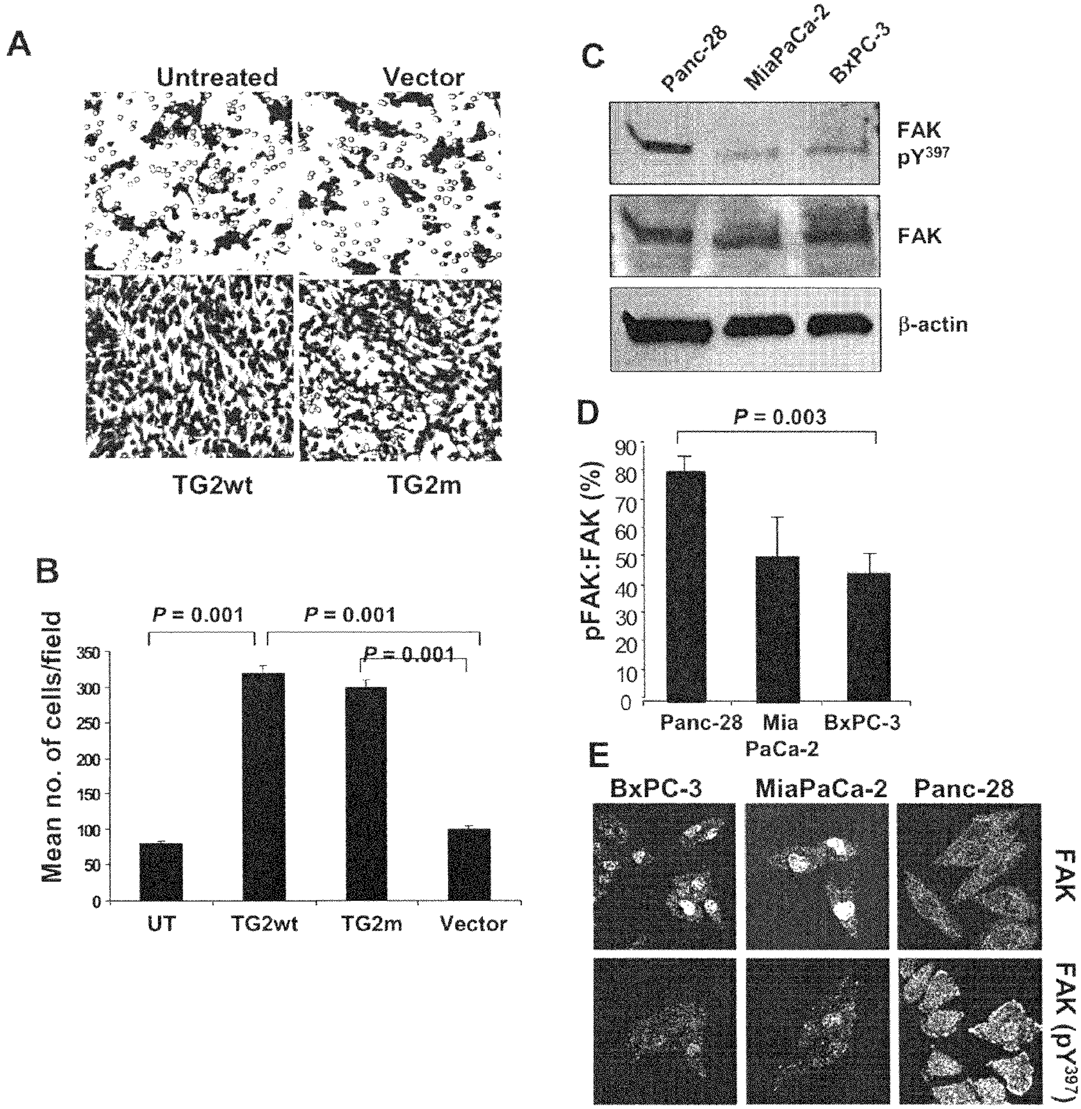

FIG. 17 shows TG2 expression is associated with invasion and constitutive activation of FAK. (A) Invasive ability of untreated BXPc-3 cells or cells infected with either wild-type (TG2wt) or active-site ($C_{277}S$) mutant (TG2m) of TG2 through the Matrigel-Transwell membranes after 48 hours of incubation, is shown. Cells infected with the vector alone (vector) served as control. (B) Mean number of TG2-infected or control BxPC-3 cells in 10 random microscopic fields was calculated and plotted. Representative of two to three independent experiments with similar results. (C) Western blot analysis was performed to determine constitutively active FAK (pY397) in the three PDAC cell lines that expressed variable TG2 levels. The membrane was stripped and reprobed with an anti-FAK antibody to determine total FAK or with anti-β-actin antibody to assure even loading of total proteins in each lane. (D) The intensities of pFAK ($pY^{397}$) and total FAK bands for each cell line were calculated using a densitometer and plotted as a percent ratio between pFAK and total FAK. (E) Confocal microscopy images of the three PDAC cell lines showing total FAK and pFAK (pY397) expression. Representative experiments done at least twice to thrice with similar results. Bars, SD.

Figure 18:
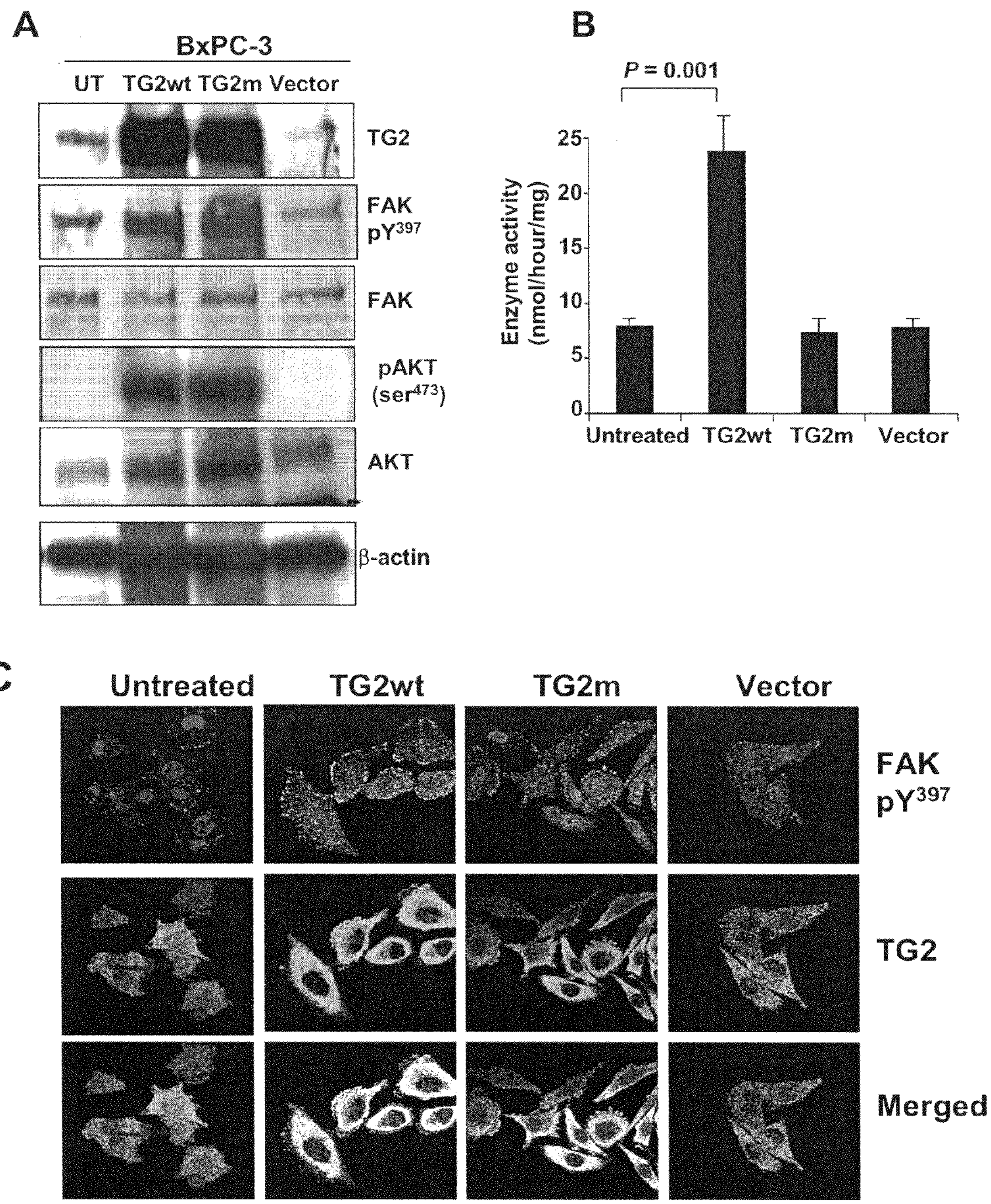

FIG. 18 shows TG2 expression results in activation of FAK and PI3K/AKT pathway. (A) Western blot analysis showing basal expression of TG2 in BxPC-3 cells after they had been infected with an adenovirus containing wild-type (TG2wt) or C277S mutant (TG2m) construct. Untreated (UT) BxPC-3 cells and cells infected with adenovirus alone (vector) served as the control. The membranes were stripped and reprobed with anti-pFAK ($pY^{397}$), total FAK, pAKT ($ser^{473}$), or total AKT antibody. Finally, the membranes were probed with β-actin antibody to assure even loading of proteins in each lane. (B) The enzymatic activity in untreated (UT) and wild-type (TG2wt) or mutant (TG2m) TG2 or empty adenovirus (vector)-infected BxPC-3 cells was also determined and plotted as the specific activity (nmol/h/mg protein). (C) Confocal microscopy images of BxPC-3 cells showing constitutive (untreated) expression of pFAK ($pY^{397}$; red fluorescence) and TG2 (green fluorescence) before and after infection with the wild-type (TG2wt) or C277S mutant (TG2m) TG2 adenoviral construct. Yellow fluorescence in the merged images indicates co-localization of TG2 and pFAK. Representative experiments repeated at least two times with similar results. Columns, mean of quadruplicate values; Bars, SD.

Figure 19:
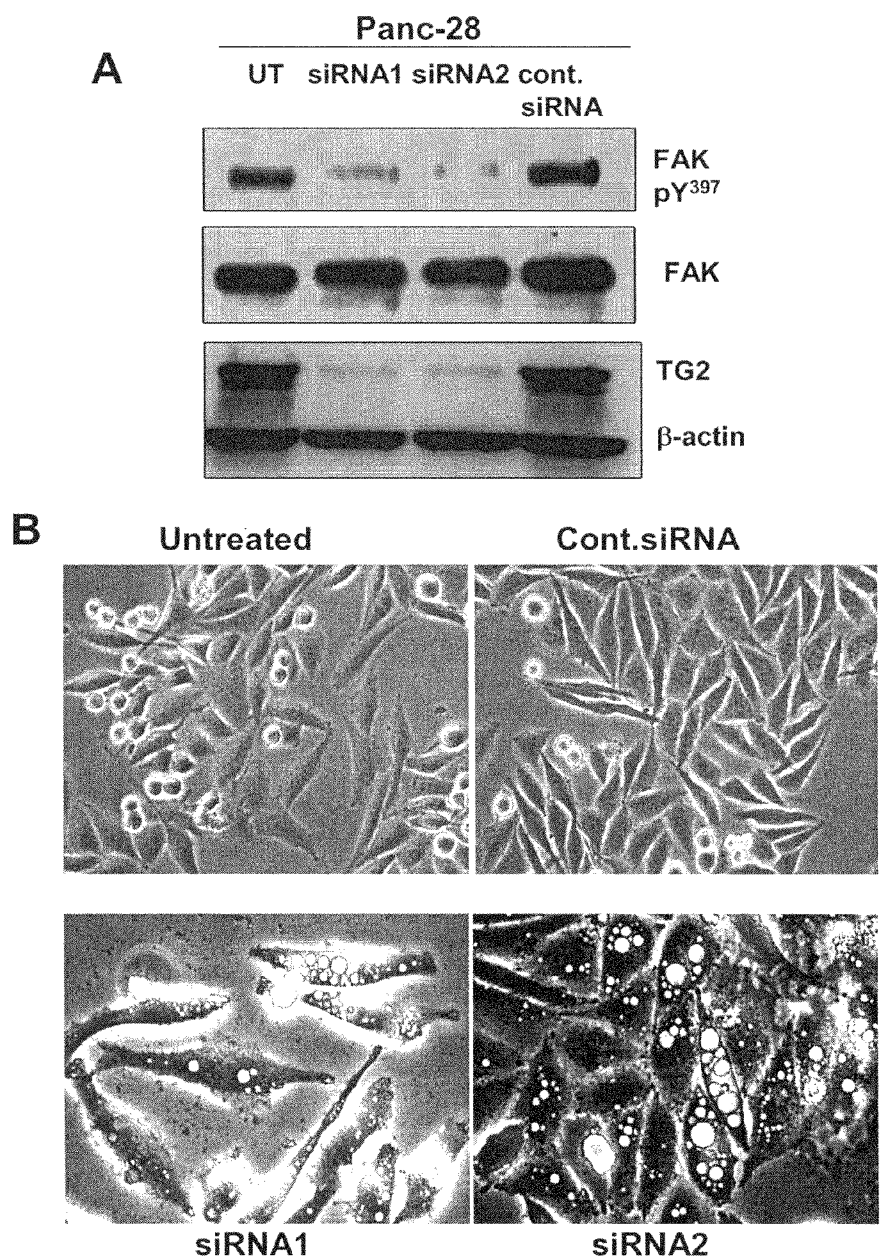

FIG. 19 shows Downregulation of TG2 results in decreased pFAK. A, Endogenous expression of TG2 in Panc-28 cells was inhibited by siRNA1 and siRNA2 transfection, as described in Materials and Methods. After 48 hours of transfection, cells were harvested, and cell lysates were subjected to Western blotting to determine TG2 expression. Untreated (UT) cells and cells transfected with scrambled siRNA (cont. siRNA) were used as controls. Membranes were stripped and reprobed with anti-pFAK (pY397) and anti-FAK antibody. β-actin was also determined to ensure even loading of proteins in each lane. B, Morphologic changes induced in Panc-28 cells in response to downregulation of endogenous TG2 by siRNA1 and siRNA2 or scrambled siRNA (cont. siRNA). Cells were treated with siRNA for 48 hours and viewed under the phase-contrast microscope. Magnification, 400×. Representative results of three independent experiments.

Figure 20:
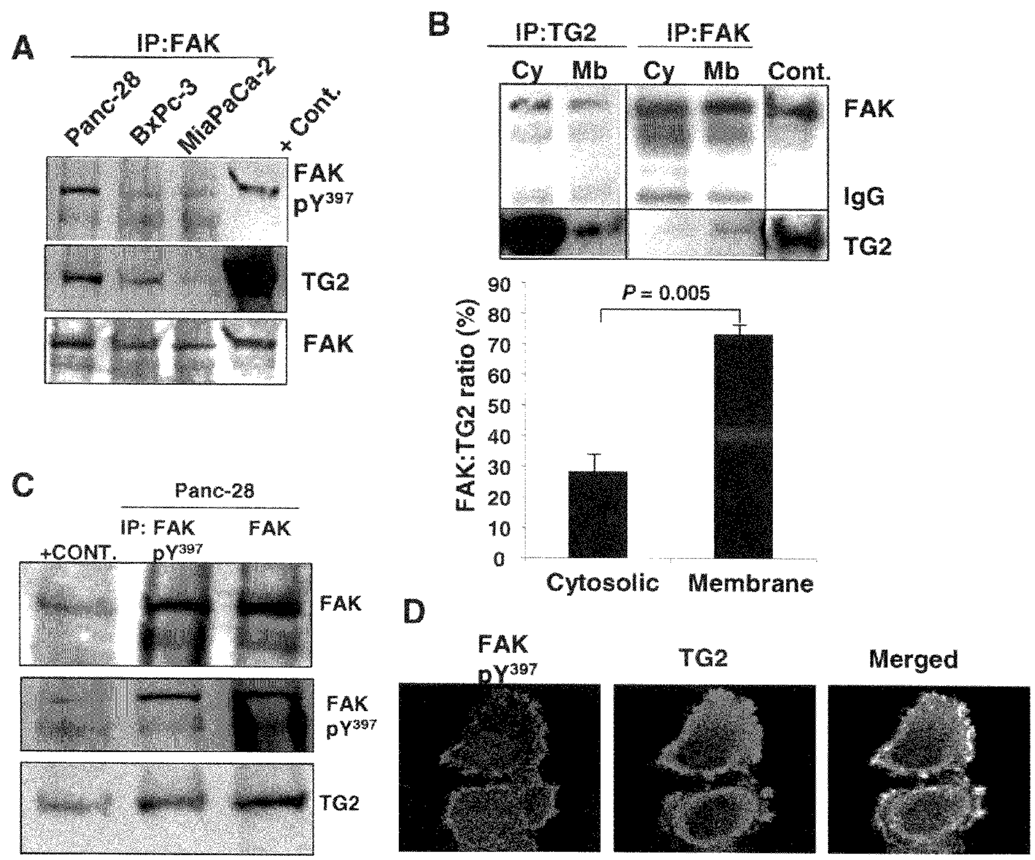

FIG. 20 shows TG2 associates with pFAK in the cell membrane. A, Total cell lysates prepared from Panc-28, BxPC-3, and MiaPaCa-2 cells were immunoprecipitated using an anti-FAK antibody. The immunoprecipitates were subjected to SDS-PAGE and Western blotting using either anti-pFAK ($pY^{397}$), anti-TG2, or anti-FAK antibody. The whole-cell extract from Panc-28 cells (+cont.) was used as a positive control. B, The membrane (Mb) and cytosolic (Cy) fractions were prepared from Panc-28 cells, as described in Materials and Methods, and immunoprecipitated using an anti-human FAK and anti-TG2 monoclonal antibody. The immunoprecipitates were subjected to SDS-PAGE and Western blotting, and the membranes were probed with anti-FAK or anti-TG2 antibody. The FAK and TG2 bands were scanned by a densitometer, and ratios were plotted as a percentage of total FAK. C, Total cell lysates from Panc-28 cells were immunoprecipitated using anti-FAK ($pY^{397}$) antibody. The immunoprecipitates were subjected to SDS-PAGE and Western blotting using anti-FAK, anti-pFAK ($pY^{397}$) or anti-TG2 antibody. The whole-cell extracts from Panc-28 cells (cont.) and immunoprecipitates using anti-FAK antibody was used as a positive control. D, Confocal microscopy images of Panc-28 cells showing co-localization of pFAK (red fluorescence; $pY^{397}$) and TG2 (green fluorescence), as evidenced by the yellow fluorescence in the merged image. Representative results from two to three experiments.

Figure 21:
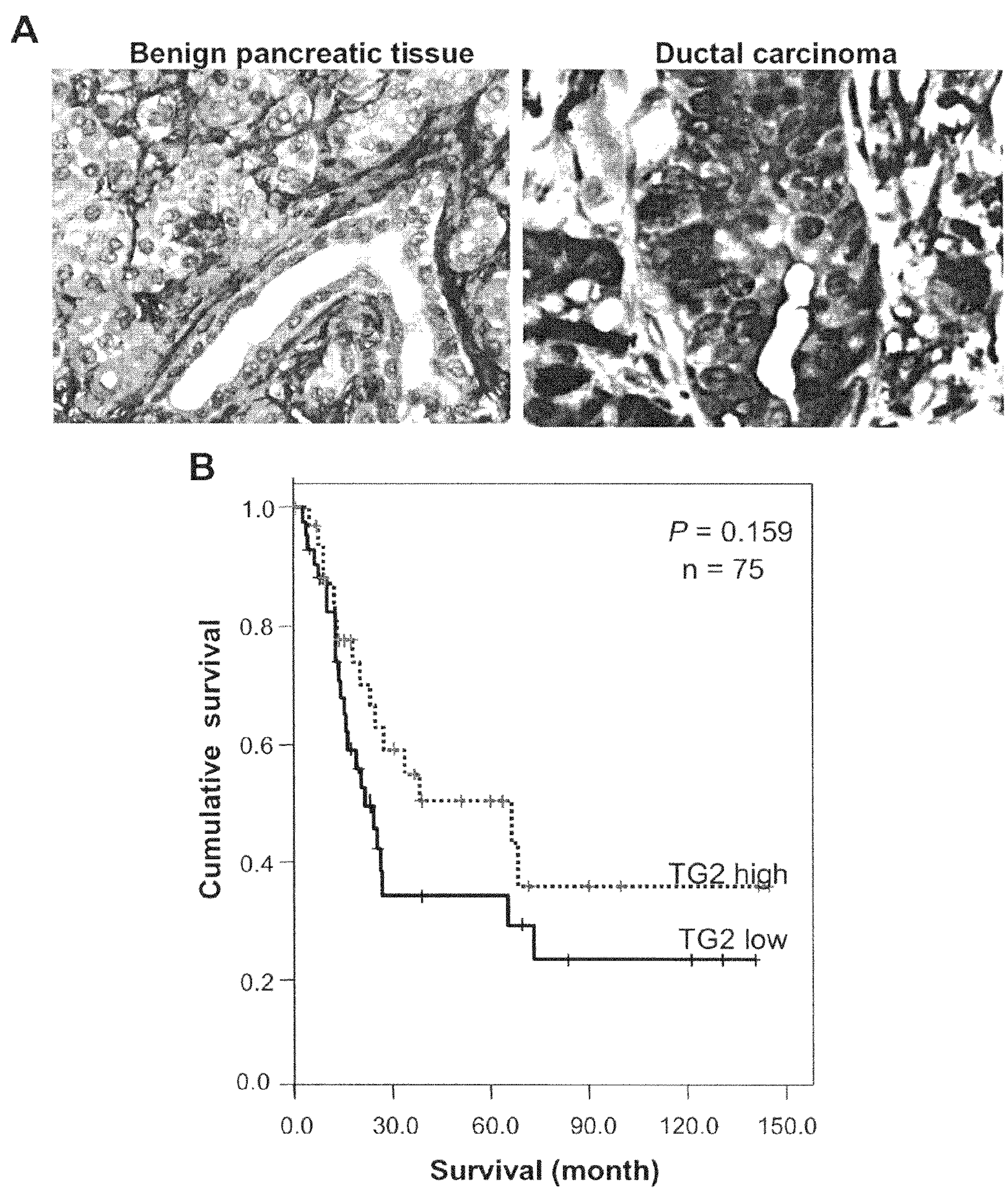

FIG. 21 shows TG2 expression in PDAC samples. A, Representative micrographs showing no TG2 expression in benign pancreatic ductal epithelium and acinar cells. Strong positive staining for TG2 is present in normal stromal cells (left side panel). Pancreatic ductal adenocarcinoma are strongly positive for TG2 staining (right side panel) (original magnification 400×). B, Kaplan-Meier curve showing the relationship between cumulative proportion of survival to TG2 expression in 75 PDAC patients.

Figure 22:
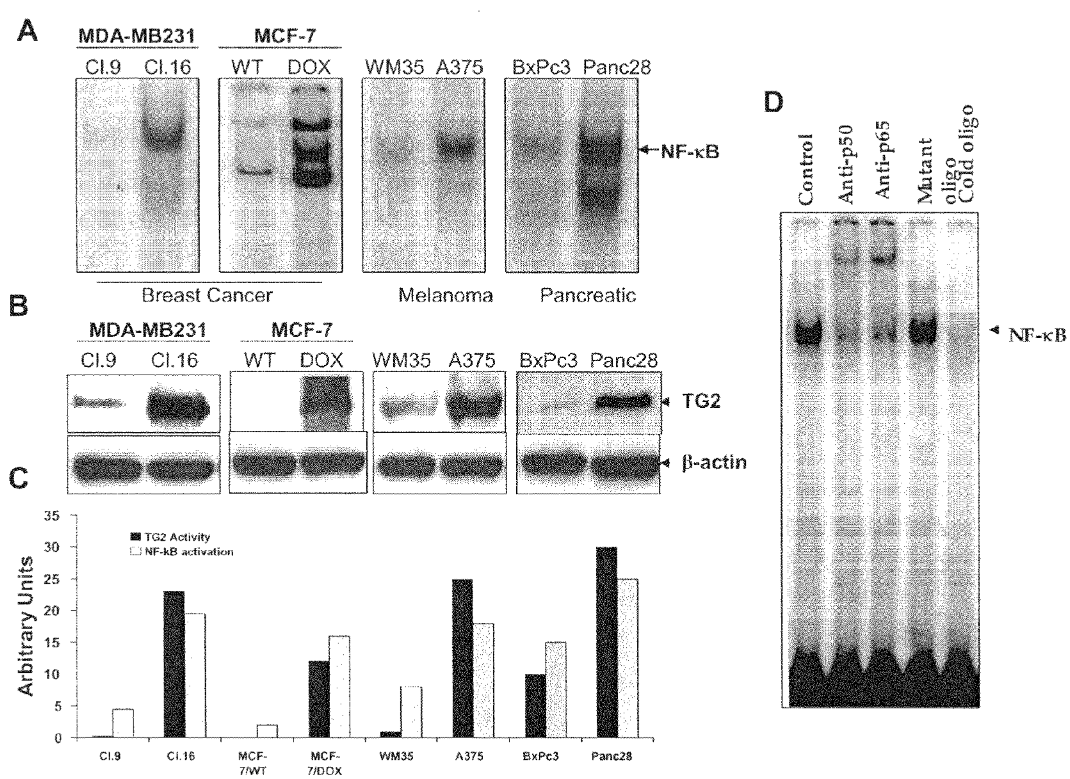

FIG. 22 shows expression of TG2 correlates with constitutive activation of NF-κB in tumor cells. (A) EMSA was performed with the nuclear extracts prepared from noninvasive (MDA-MB231/cl. 9) and invasive (MDA-MB231/cl. 16) breast cancer cell lines, drug-sensitive (MCF-7/WT) and drug-resistant (MCF-7/DOX) breast cancer cell lines; early-stage (WM35) and late-stage (A375) malignant melanoma cell lines, and well-differentiated (BxPC3) and highly aggressive (Panc28) pancreatic cancer cell lines. (B) Western blot analysis of the TG2 expression in the eight cancer cell lines. (C) Comparison of TG2 activity and constitutive NF-κB activation in the eight cancer cell lines. (D) Supershift analysis of NF-κB using EMSA with the nuclear extracts prepared from Panc28 cells. Nuclear extracts were incubated with an anti-p65 antibody, an anti-p50 antibody or with nonradioactive (cold) or mutant NF-κB oligonucleotides and then examined for DNA binding. The results shown are from representative experiments repeated at least three with similar results.

Figure 23:
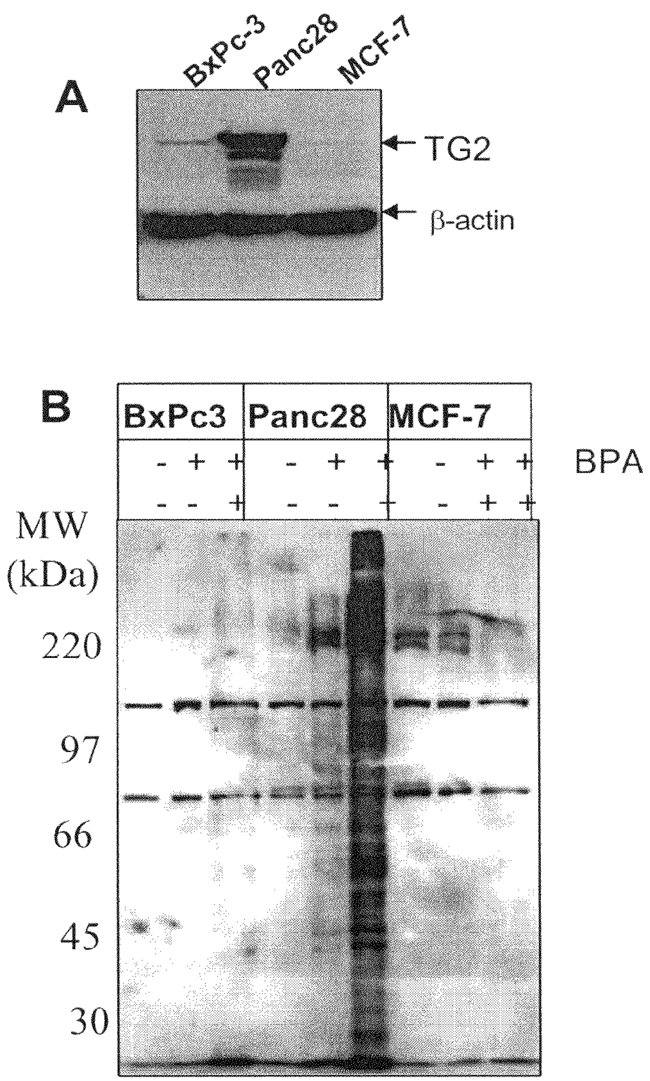
Figure 23:
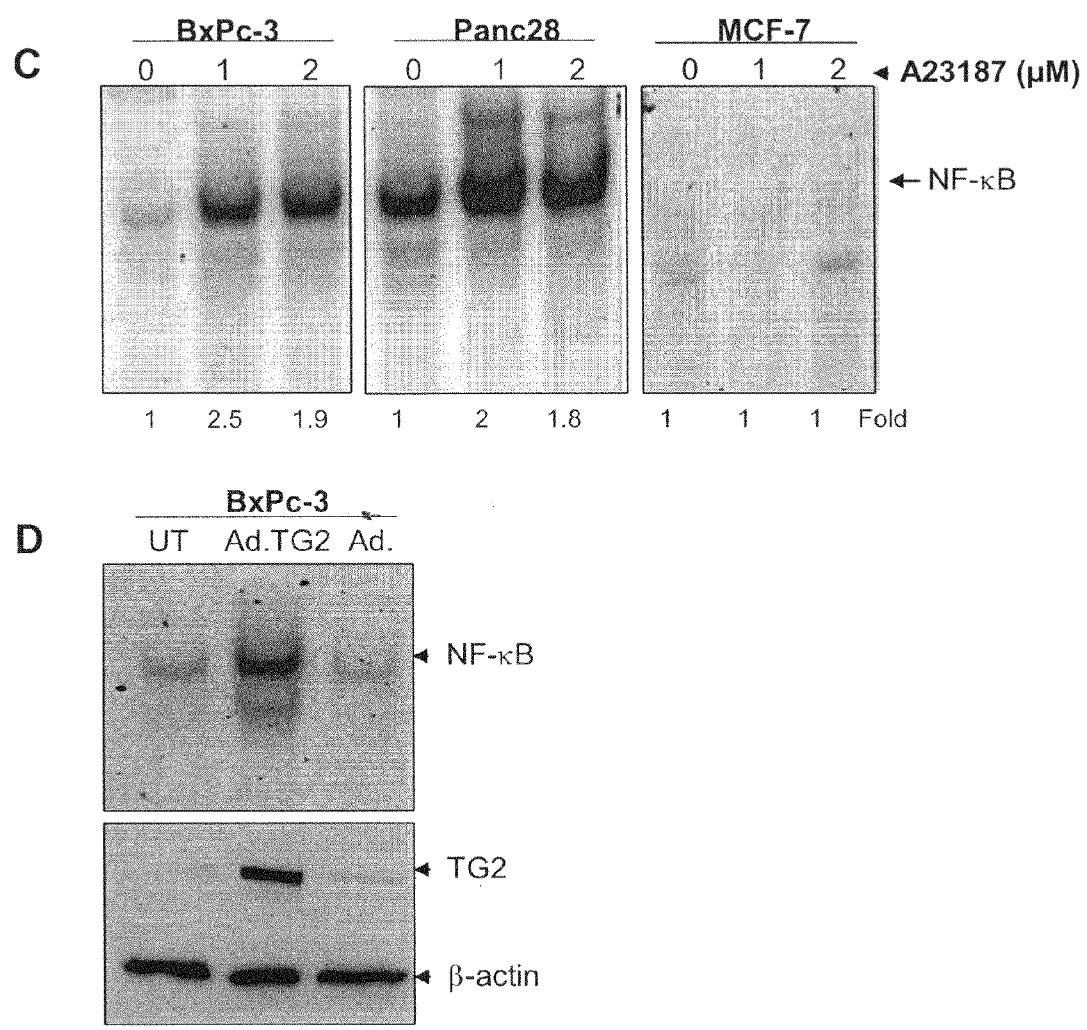

FIG. 23 shows citation and overexpression of TG2 lead to activation of NF-κB in tumor cells. (A) Western blot showing basal expression of TG2 protein in BxPc3, Panc28, and MCF-7/WT cells. (B) The level of constitutive and inducible (calcium ionophore A23187-mediated) activation of endogenous TG2 was determined according to BPA conjugation with cellular proteins as described in Materials and Methods. (C) EMSA showing NF-κB activation in BxPc3 and Panc28 cells in response to treatment with A23187 (24 hours at a concentration of 1 μM or 2 μM). MCF-7/WT cells that lacked TG2 expression failed to show any constitutive or A23187-induced NF-κB activation. (D) TG2 overexpression causes NF-κB activation. EMSA (top panel) and Western blot (bottom panel) showing constitutively activated NF-κB and TG2 levels in untreated (UT), TG2-infected (Ad.TG2), and vector-alone-infected (Ad) BxPC3 cells. The results shown are from representative experiments repeated at least two to three times with similar results.

Figure 24:
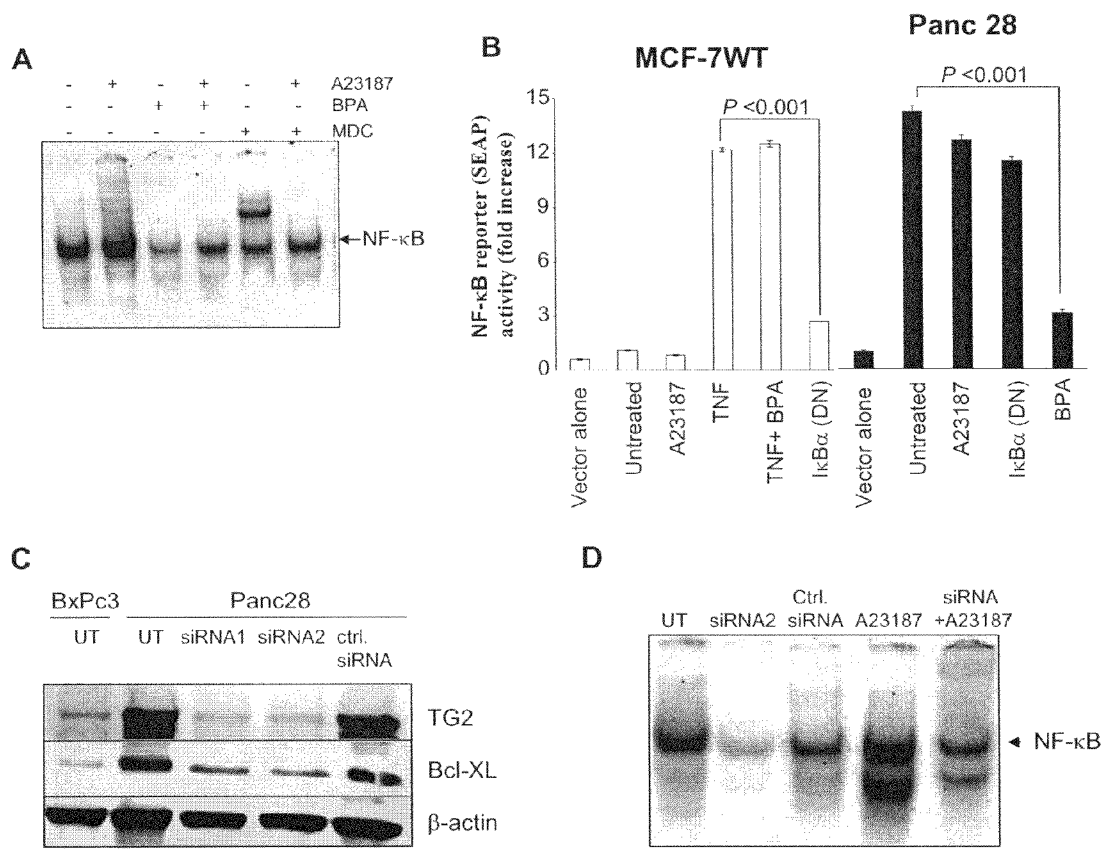

FIG. 24 shows inhibition of TG2 activity inhibits activation of NF-κB. (A) EMSA showing inhibition of constitutive and A23187-induced NF-κB activation in Panc28 cells in response to treatment with two TG2-specific competitive inhibitors: MDC (50 μM for 24 hours) and BPA (1 mM for 24 hours). (B) expression of an NF-κB-induced reporter gene (SEAP) in response to various treatments in TG2-negative MCF-7/WT and high-TG2-expressing Panc28 cells. Cells were transiently transfected with NF-κB promoter containing plasmid linked to the SEAP gene. Where indicated cells were co-transfected with IκBα-dominant negative (IκBα-DN) mutant plasmid and/or exposed to TNF (1 nM), BPA (1 mM), or A23187 (1 μM). Results are expressed as fold activity over the non-transfected control. (C) TG2 protein expression in untreated control (UT), scrambled siRNA (Ctrl. siRNA), and TG2-specific siRNA (siRNA1 and siRNA2)-transfected cells is shown. The membranes were stripped and reprobed with anti-Bcl-XL and β-actin antibodies. (D) EMSA showing the effect of downregulation of endogenous TG2 by siRNA2 on constitutive and A23187-induced NF-κB activation in Panc28 cells. The results are from representative experiments performed at least two to three times with similar results.

Figure 25:
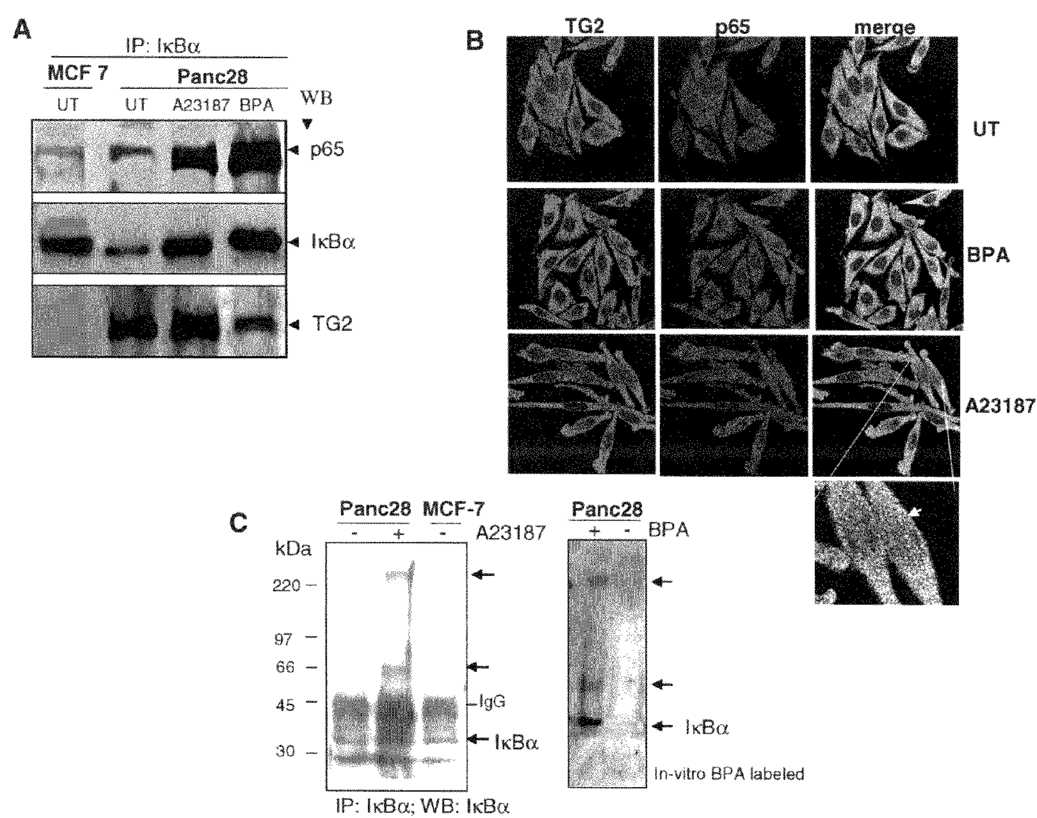

FIG. 25 shows TG2 is associated with NF-κB in Panc28 cells. (A) immunoprecipitation of cytosolic extracts prepared from untreated (UT), A23187-induced (2 μM for 24 hours), and BPA-treated (1 mM for 24 hours) Panc28 cells with a rabbit anti-IκBα antibody effectively pulled down the p65 and TG2 proteins in addition to the IκBα protein. TG2-negative MCF-7/WT cells served as controls. WB, Western blot. (B) confocal microscopic images showing co-localization of TG2 and p65 in the cytoplasm in Panc28 cells. A further increase in the association of TG2 with p65 and the translocation of the complex to the nucleus was observed in response to treatment with A23187 (2 μM for 24 hours). Inset: the white spots indicate the association and co-localization of p65 with TG2 in the nucleus. UT, untreated. (C) Cell extracts from BXPC-3 or Panc28 cells were immunoprecipitated (IP) using anti-TG2 antibody and probed with anti-p65 and anti-TG2 antibody. (D) Immunoprecipitation (IP) and Western blotting (WB) (left panel) of cytoplasmic extracts from Panc28 cells indicating the presence of a dimeric form of IκBα (66 kDa) in addition to the 33-kDa monomeric band. Analysis of TG2-negative MCF-7/WT cells did not indicate the presence of an IκBα dimer. A further increase in the intensity of the dimeric band and the appearance of a new polymeric IκBα band approximately 220 kDa in size was evident in response to treatment with A23187 (2 μM for 24 hours). The right panel shows the monomeric, dimeric, and polymeric forms of the IκBα protein in a rabbit anti-IκKα antibody immunoprecipitate from a Panc28 cytosolic extract following their in vitro labeling with BPA. IκBα-conjugated BPA bands were detected using streptavidin-conjugated peroxidase as a probe.

Figure 26:
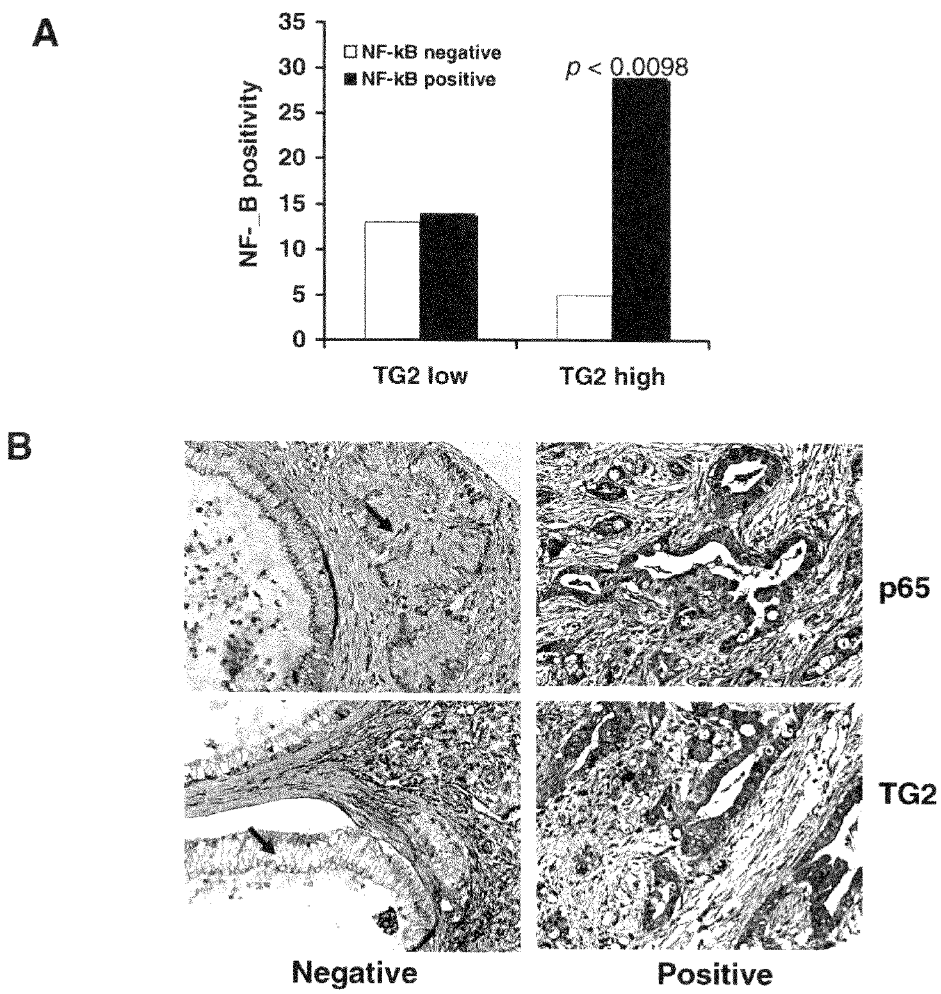

FIG. 26 shows TG2 expression correlates with NF-κB activation in pancreatic tumors. (A) Sections from pancreatic cancer samples immunostained for the p65 subunit of NF-κB and TG2 protein expression. The images show the representative sections with positive and negative immunostaining for TG2 and p65. The arrows in the left panels indicate the locations of tumor cells. The TG2 staining in the negative sample (left bottom panel) shows endothelial and other stromal components that constitutively express TG2. Original magnification 200×. (B) NF-κB activation/overexpression was observed in 29 (85%) of the 34 pancreatic carcinoma samples with high levels of TG2 expression. In comparison, 13 (48%) of the 27 pancreatic carcinoma samples with low levels of TG2 expression showed a lack of NF-κB activation/overexpression, revealing a significant correlation between TG2 expression and NF-κB activation in these samples (P<0.0098).

Figure 27:
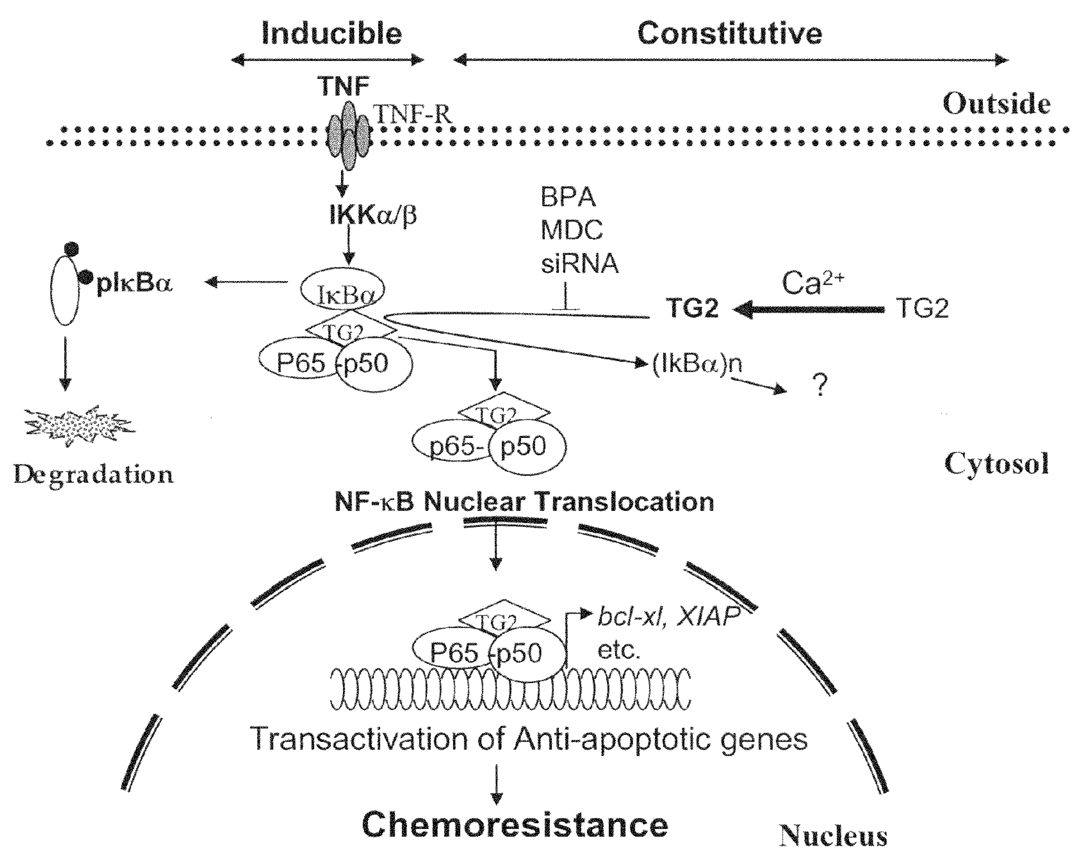

FIG. 27 shows a schematic representation of TG2-independent (IKK-dependent) and TG2-dependent (IKK-independent) NF-κB activation pathways. By catalyzing cross-linking of IκBα, TG2 can destabilize its association with p65:p50 complex resulting in constitutive activation of NF-κB and its translocation to the nucleus. The fate of TG2-catalyzed polymeric IκBα forms is not yet known. Alternatively, association of TG2 with p65:p50 complex could mitigate the binding of IκBα to NF-κB complex, resulting in its constitutive activation. TG2-mediated activation of NF-κB can result in constitutive expression of various antiapoptotic target genes, such as Bcl-xl and X-linked inhibitor of apoptosis protein (XIAP), resulting in a chemoresistance phenotype.

Figure 28:
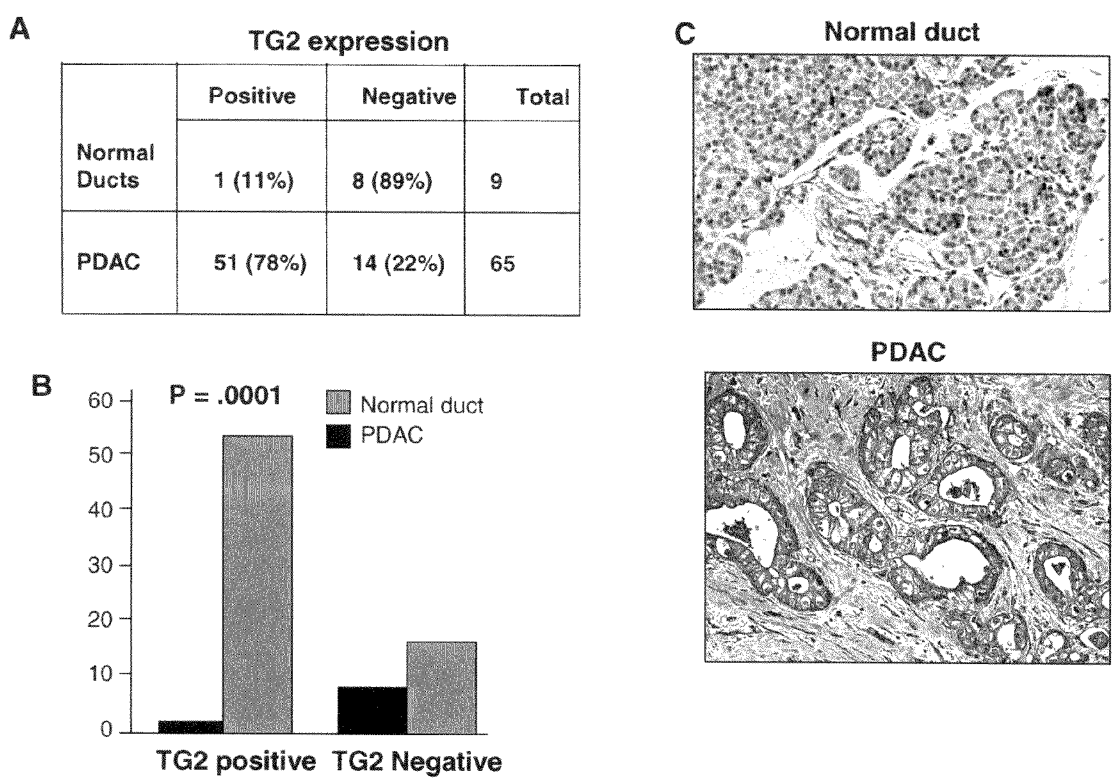

FIG. 28 is a cross-tabulation and histogram showing overexpression of TG2 in PDAC tumor samples. TG2 expression was observed in 51 of 65 (78%) PDAC tumor samples and 1 of 9 (11%) normal pancreatic ductal epithelium samples (p<0.00001). C, Representative tissue samples showing no TG2 staining and faint TG2 staining of endothelial cells in a normal pancreatic ductal epithelium sample (upper panel) and strong TG2 staining in a PDAC tumor sample (lower panel). Original magnification ×200.

Figure 29:
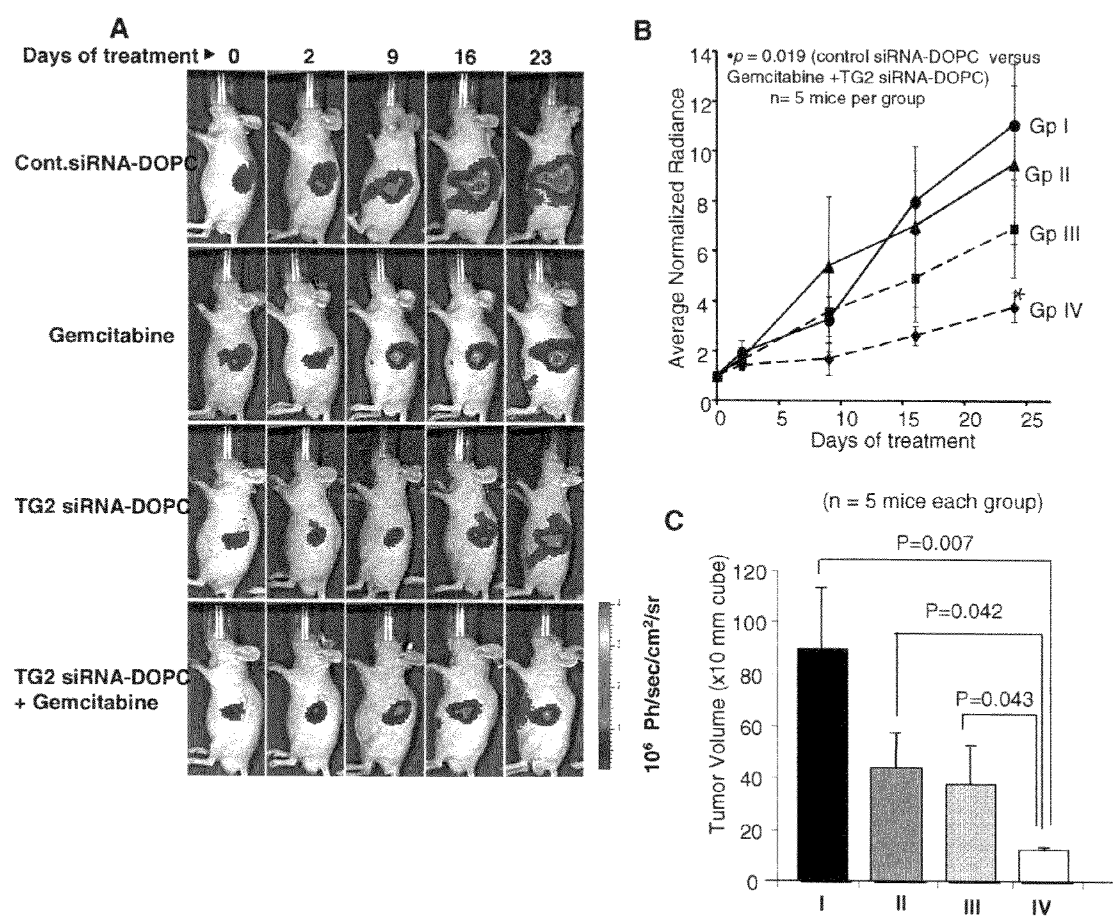

FIG. 29 shows IVIS images of representative mice in each treatment group taken at the indicated days of treatment. Mice were imaged in the ventral view using the LivingImage Software program. B, Analysis of the IVIS images revealing that tumor growth in mice given TG2 siRNA-DOPC in combination with gemcitabine (group IV) was significantly inhibited (p=0.019) as compared with that in mice given control siRNA-DOPC (group I). C, Final tumor volumes in mice at the end of treatment. Histogram, Mean tumor volumes in mice in different treatment groups; bars, standard deviations. Treatment with TG2 siRNA-DOPC alone (group III) or gemcitabine alone (group II) resulted in 50-60% reduction in tumor growth when compared with treatment with control siRNA-DOPC (group I). Treatment with the combination of TG2 siRNA-DOPC and gemcitabine (group IV) resulted in a much superior response when compared with treatment with TG2 siRNA-DOPC or gemcitabine alone (P<0.05).

Figure 30:
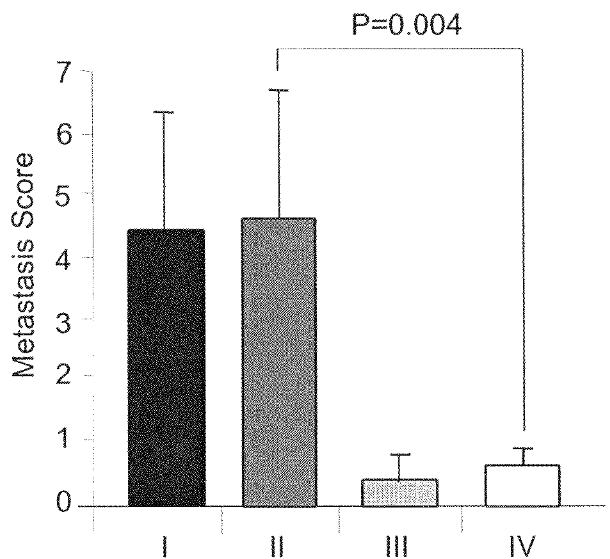

FIG. 30 is a histogram showing the mean metastasis scores in mice in different treatment groups. Mice given TG2 siRNA-DOPC either alone (group III) or in combination with gemcitabine (group IV) had dramatic decreases in the average metastasis score (p=0.004) when compared with mice given control siRNA (group I). Mice given gemcitabine alone (group II) had no decreases in the metastasis score when compared with mice in the control group (Group I). B, Cross-tabulation of the metastasis scores in individual mice observed at the end of the treatment period.

Figure 31:
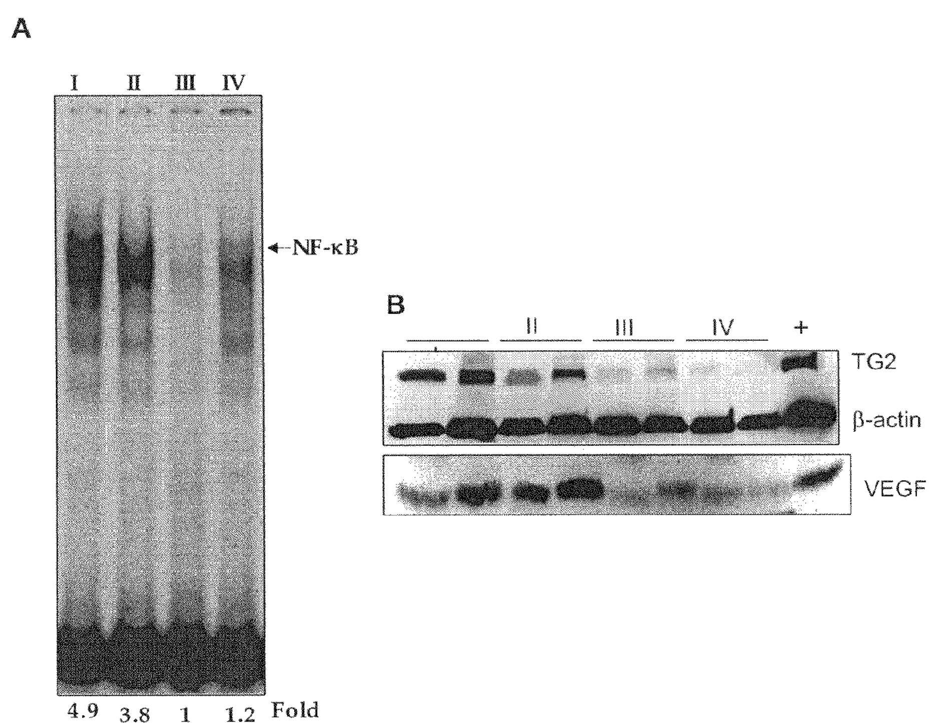

FIG. 31 shows an electrophoretic mobility shift assay of representative tumors showing more than fourfold inhibition of constitutive NF-κB activation in Panc-28 tumors in response to treatment with TG2 siRNA-DOPC either alone (group III) or in combination with gemcitabine (group IV) compared with a onefold inhibition in gemcitabine treated group (II). B, Western blot analysis showing TG2 expression in representative Panc-28 tumors resected from mice in each treatment group. More than 80% downregulation of TG2 expression is evident in tumors obtained from mice given TG2 siRNA-DOPC either alone (group III) or in combination with gemcitabine (group IV). The membranes were stripped and reprobed with an anti-VEGF antibody. Downregulation of TG2 expression in tumors obtained from mice in groups III and IV was associated with a parallel decrease in VEGF expression when compared with mice in the control siRNA (group I) and gemcitabine alone (group II) groups. The membranes were probed with an anti-β-actin antibody to ensure even loading of proteins in each lane. +, positive control.

Figure 32:
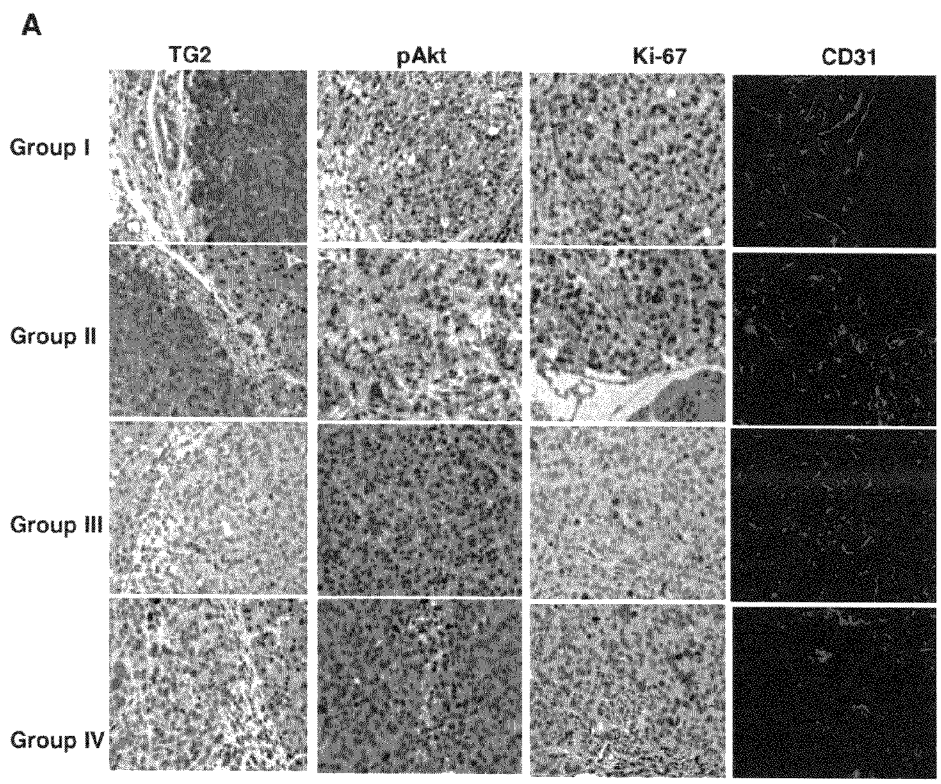
Figure 32:
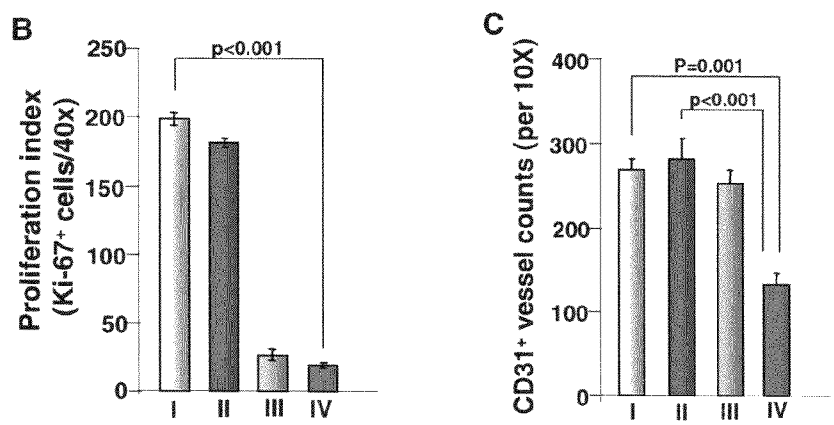

FIG. 32 contains the representative micrographs showing immunohistochemical staining for TG2 expression (TG2), pAkt expression and cell proliferation (Ki-67) in Panc-28 tumors obtained from mice. Also shown is staining for CD31 to indicate neovascularization in representative tumors growing in mice in the various treatment groups (CD31). A significant decrease in TG2 expression, Ki-67 staining, and pAkt (ser473) expression was evident in tumor tissue samples obtained from mice given TG2 siRNA-DOPC alone (group III) or in combination with gemcitabine (group IV) when compared with mice given control siRNA (group I) or gemcitabine alone (group II). Similarly, a significant reduction in CD31 expression, representing neovascularization, was evident in tumors obtained from mice given TG2 siRNA-DOPC in combination with gemcitabine (group IV). B, Number of Ki-67 positive cells (mean±SE) determined by counting 10 random microscopic fields, each in three tumor samples from different treatment groups. C, Number of microvessels (mean±SE) counted in 20 random fields each, from 4 tumor samples in each treatment group.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

Description

The present disclosure provides, in certain embodiments, a method for treating cancer comprising inhibiting transglutaminase activity. Suitable cancer types for which the methods of the present disclosure can be used to treat include, but are not limited to, pancreatic, breast, and ovarian cancers and melanoma. The inhibition of transglutaminase activity may be performed by one or more techniques, including, but not limited to, down-regulating transglutaminase expression, inhibiting TG2 translation, or blocking TG2 enzymatic activity, such as with a small molecule inhibitor or intracellular antibody (intrabody).

As used herein, the term "inhibiting transglutaminase activity" refers to a substantial reduction in one or more activities of the transglutaminease protein, in any of its isoforms or as part of a complex with one or more other molecules, such activities including, but not limited to, associating with one or more of the β1, β3, β4, and β5 members of the integrin family of proteins, activation of a nuclear transcription factor, and activation of a focal adhesion kinase.

As used herein, the term "downregulating transglutaminse expression" refers to a substantial reduction in the expression of the transglutamine protein in the target cell through any of the methods disclosed herein or those known to one of ordinary skill in the art, with the benefit of the present disclosure.

As used herein, the term "inhibiting TG2 translation" refers to a substantial reduction in the translation of the TG2 protein in the target cell from RNA encoding the TG2 protein, including RNA natively transcribed by the target cell and RNA artificially introduced into the target cell.

As used herein, the term "blocking TG2 enzymatic activity" refers to a substantial reduction in the ability of TG2 to act as an enzyme (i.e. have a designated effect on one or more substrate molecules) through any of the methods disclosed herein or those known to one of ordinary skill in the art, with the benefit of the present disclosure.

In some embodiments, the present disclosure provides a method for treating cancer comprising inhibiting transglutaminase activity. In some embodiments, the inhibition of transglutaminase activity may comprise downregulating transglutaminase expression. Suitable methods for downregulating transglutaminase expression may include: inhibiting transcription of TG2 mRNA; degrading TG2 mRNA by methods including, but not limited to, the use of interfering RNA (RNAi); blocking translation of TG2 mRNA by methods including, but not limited to, the use of antisense nucleic acids or ribozymes, or the like. In some embodiments, a suitable method for downregulating transglutaminase expression may include providing to the cancer a small interfering RNA (siRNA) targeted to TG2. In some embodiments, suitable methods for downregulating transglutaminase activity may include inhibiting protein kinase C delta (PKCdelta). Suitable methods for inhibiting PKCdelta include, but are not limited to, targeting PKCdelta with an siRNA or a small molecule. In some embodiments, such a small molecule may comprise rottlerin. In some embodiments, suitable methods for down-regulating transglutaminase activity may include administering a small molecule inhibitor of TG2. In some embodiments, such a small molecule may comprise rottlerin. In some embodiments, suitable methods for downregulating transglutaminase activity may include downregulating protein kinase C delta expression; or providing to the cancer an siRNA or pharmacologic agent capable of inhibiting transglutaminase expression or protein kinase C expression. In some embodiments, it may be advantageous to use two or more of these methods simultaneously or in series. One or ordinary skill in the art, with the benefit of the present disclosure, may recognize suitable methods for downregulating transglutaminase expression that are still considered within the scope of the present disclosure.

To facilitate a better understanding of the present invention, the following examples of specific embodiments are given. In no way should the following examples be read to limit or define the entire scope of the invention.

EXAMPLES

Example 1

Tissue Transglutaminase Expression Promotes Cell Attachment, Invasion and Survival in Breast Cancer Cells Materials and Methods Chemicals and Reagents Unless stated otherwise, all chemicals and reagents were of analytic grade and were purchased from Sigma-Aldrich (St Louis, Mo., USA). Primary antibodies against TG2 and β-actin were from Neomarkers (Fremont, Calif., USA), whereas antibodies against αv-integrin (clone 1953Z), α5-integrin (clone 1956Z), α6-integrin (clone 4F10), β1-integrin (clone 1965Z), β3-integrin (clone 1957Z), β4-integrin (clone ASC-3) and β5-integrin (RB1926) were from Chemicon (Temecula, Calif., USA). The secondary antibody, horseradish peroxidase-conjugated anti-mouse immunoglobulin G (IgG) was from Amersham-Pharmacia (San Francisco, Calif., USA).

Cell Culture

The parental human breast cancer cell line, MDA-MB231, was purchased from American Type Culture Collection (Manassas, Va., USA). MDA-MB231 subclones (MDA231cl. 9 and MDA231cl. 16) were isolated by the limiting dilution technique as described earlier (Mehta et al., 2004). All cells were maintained in a log phase of cell growth by culturing in Roswell Park Memorial Institute (RPMI)-1640 medium supplemented with heat-inactivated fetal calf serum (10%, v/v), 0.2% Normocin (InvivoGen, San Diego, Calif., USA), 20 mM L-glutamine and 25 mM N-2-hydroxyethylpiperazin-N'-2-ethanesulfonic acid (Life Technologies, Rockville, Md., USA) in a humidified incubator at $37^1$C in the presence of 5% $CO_2$ and 95% air.

Enzyme Activity

Cells at 80% confluence were washed in phosphate-buffered saline (PBS), lysed and resuspended in lysis buffer (20 mM TriHCl, pH 7.4, containing 1 mM ethylenediaminetetraacetic acid (EDTA), 150 mM NaCl, 0.1% 2-mercaptoethanol and 1 mM L-phenylmethylsulfonyl fluoride). Cells were lysed in the same buffer by probe sonication, followed by the determination of protein content by using a protein-dye reagent (Bio-Rad, Hercules, Calif., USA). Cell lysates were then assayed for TG2 activity by determining the $Ca^{2+}$-dependent incorporation of [$^3$H]putrescine (specific activity, 14.3 Ci/mmol; Amersham Pharmacia) into N,N-dimethylcasein as described previously (Chen et al., 2002).

Western Blotting

Thirty micrograms of cell lysate protein was separated by sodium dodecyl sulfate-polyacrylamide gel electrophoresis on a 7.5% gel and electrophoretically transferred onto a nitrocellulose membrane. The membrane was probed with an anti-TG2 monoclonal antibody (CUB7401; Neomarkers). The antigen-antibody reaction was detected by using an electrochemiluminescence system. All membranes were stripped and reprobed with an anti-b-actin antibody (Sigma-Aldrich) at a dilution of 1:2000 to ensure even loading of proteins in the different lanes.

Confocal Microscopy

Cells ($2\times10^5$) were cultured on glass coverslips in six-well plates, rinsed three times with PBS, fixed with 3.7% paraformaldehyde for 15 min and blocked with 5% normal-goat serum for 1 h. The cells were immunostained by using primary antibodies specific to integrins and TG2. Either goat anti-mouse IgG Alexa 488 (or 546) or goat anti-rabbit IgG Alexa 488 (or 546) (Molecular Probes, Eugene, Oreg., USA) was used as the secondary antibody. The stained coverslips were mounted on glass microscope slides in mounting medium (80% glycerol plus 20% PBS). Slides were visualized under a Zeiss laser scanning microscope 510 (Carl Zeiss Microimaging Inc., Thornwood, N.Y., USA) and images were obtained.

Cell Viability, Growth and Attachment

Ninety-six-well plates (Corning/Costar, Rochester, N.Y., USA) were coated with 20 mg/ml Fn (Sigma-Aldrich) or 0.1% BSA in PBS. The nonspecific binding sites were blocked with 2% BSA. The cells grown in T-75 flasks to 80-90% confluence were isolated by 2 mM EDTA treatment, washed with RPMI medium and resuspended in serum-free medium ($2\times10^4$ cells/ml). Aliquots (200 ml) of the cell suspension were added to Fn-or BSA-coated wells in quadruplicate and incubated at 37° C. for 48 h. At the end of incubation period, the number of viable cells remaining in the well was determined by measuring their ability to reduce 3-(4,5-dimethylthiazol-2-yl)-5-(3-carboxymethoxyphenyl)-2H-tetrazolium (MTS) into soluble formazan.

In some experiments, cells were transfected with TG2-specific (siRNA1 and siRNA2) or control (scrambled) siRNA as described earlier (Herman et al., 2006). After 48 h transfection, cells were harvested with 2 mM EDTA, washed and assayed for TG2 activity and levels or were plated in quadruplicate in each well of 96-well plates that had been precoated with Fn or BSA. After 48 h of incubation, cells were examined under the light microscope and tested for cell viability by using the MTS assay.

For the cell attachment assay, the control and siRNA-transfected cells ($2\times10^4$ cells/well/0.2 ml serum-free RPMI medium) were incubated in Fn- or BSA-coated 96-well plates. After a 1-h incubation at 37° C., cells were viewed under a microscope for morphologic analysis. Non-adherent cells were removed by washing with PBS, and adherent cells were fixed with 3.7% paraformaldehyde for 1 h, washed twice with PBS and stained with 0.1% crystal violet for 40 min. The stained cells were washed with water and lysed in 0.5% Triton X-100, after which the optical density was read at 540 nm.

TG2wt and TG2m Adenovirus Generation

Adenovirus containing full-length TG2 (TG2wt) or C277S mutant (TG2m) cDNA constructs was kindly provided by Dr Ugra Singh (The University of Texas, Temple, Tex., USA). Briefly, TG2 cDNA cloned in pcDNA3.1 vector was first subcloned in a pshuttle 2 vector and then in BD adenoX adenoviral vector. Human embryonic kidney-293 cells were transfected with recombinant adenoviral plasmid for packaging of adenovirus particles. Adenovirus was purified on CsCl gradient and used at 25 MOI. Cells infected with lacZ adenovirus served as control.

Cell Migration and Invasion

Relative cell motility on Fn-coated plates was assayed by determining the extent of outward cell migration from an agarose droplet as described earlier (Balklava et al., 2002). Briefly, cells were harvested, resuspended at a concentration of $1\times10^6$/ml in RPMI medium and mixed with low-melting point, agarose (0.2% final concentration) maintained at 38° C. The cell suspension in the agarose was then seeded into the center of the Fn-coated Petri dishes. The agarose was allowed to set for 7 min at 4° C., after which growth medium was added and left for 48 h at 37° C. Cells were then fixed with 3% glutaraldehyde for 30 min, stained with crystal violet (0.5% in 70% ethanol) and air-dried. The number of cells migrating out and away from the agarose was determined by taking a picture under the light microscope.

The invasive behavior of cells was determined in vitro by using Matrigel-transwell inserts, as described earlier (Mehta et al., 2004). Briefly, transwell inserts with a 12-mm pore size were coated with 0.78 mg/ml Matrigel in cold serum-free medium. Cells were then trypsinized and washed with serum-free medium. The cell pellets were subsequently resuspended in serum-free medium, and 0.5 ml of the cell suspension ($1\times10^6$ cells) was added to duplicate wells. After a 48-h of incubation, the cells that passed through the filter on the underside of the membrane were stained and counted under a light microscope. Ten fields of cells were counted for each well, and the mean number of cells per field was calculated. Each experiment was performed in triplicate and repeated at least two times.

RT-PCR

Total RNA was isolated from the parental MDA-MB231 cell line and its two sublines (cl. 9 and cl. 16) with Trizol reagent (Invitrogen, San Diego, Calif., USA). cDNA was synthesized from 5 μg of total RNA by using SuperScript reverse transcriptase (Life Technologies Inc.) as per the manufacturers instructions. cDNA was subjected to PCR by using gene-specific primers (Table 1). PCR was performed with 5-25 μg of reverse-transcribed RNA, 1 U of Taq polymerase and 100 ng/ml of sense and antisense primers in a total volume of 50 μl. Each cycle consisted of 30 s of denaturation at 94° C. at the different annealing and elongation temperatures shown in Table 1. Amplified PCR products were analysed by electrophoresis on 1% agarose gel and visualized under the ultraviolet light after staining with ethidium bromide. A mock-RT-PCR reaction, in which the RT was omitted, was always run in parallel as a control.

TABLE 1

Primers used in the RT-PCR assay

| Primer | Product size (bp) | Annealing temp. (° C.) | Sequence (sense/antisense) |
|---|---|---|---|
| TG2 | 786 | 65 | 5'-TATGGCCAGTGCTGGGTCTTCGCC-3' (SEQ ID NO: 1)/<br>5'-GGCTCCAGGGTTAGGTTGAGCAGG-3' (SEQ ID NO: 2) |

TABLE 1-continued

| Primers used in the RT-PCR assay | | | |
|---|---|---|---|
| Primer | Product size (bp) | Annealing temp. (° C.) | Sequence (sense/antisense) |
| MMP-1 | 786 | 58 | 5'-CGACTCTAGAAACACAAGAGCAAGA-3' (SEQ ID NO: 3)/<br>5'-AAGGTTAGCTTACTGTCACACGCTT-3' (SEQ ID NO: 4) |
| Osteopontin | 375 | 60 | 5'-TGAGAGCAATGAGCATTCGGATG-3' (SEQ ID NO: 5)/<br>5'-CAGGGAGTTTCCATGAAGCCAC-3' (SEQ ID NO: 6) |
| E-cadherin | 500 | 55 | 5'-TCCCATCAGCTGCCCAGAAA-3' (SEQ ID NO: 7)/<br>5'-TGACTCCTGTGTTCCTGTTA-3' (SEQ ID NO: 8) |
| CXCR4 | 454 | 55 | 5'-AGTATATACACTTCAGATAAC-3' (SEQ ID NO: 9)/<br>5'-CCACCTTTTCAGCCAACAG-3' (SEQ ID NO: 10) |
| CTGF | 471 | 62 | 5'-CAACTGCCTGGTCCAGACC-3' (SEQ ID NO: 11)/<br>5'-CACTCTCTGGCTTCATGCC-3' (SEQ ID NO: 12) |
| IL-11 | 351 | 55 | 5'-AGCCACCACCGTCCTTCCAAA-3' (SEQ ID NO: 13)/<br>5'-CCTCCGTCCCCACCCCAACAT-3' (SEQ ID NO: 14) |
| GAPDH | 574 | 55 | 5'-GAACTGTGTTTGCCGCCTGGTC-3' (SEQ ID NO: 15)/<br>5'-GTCAGCTGGGAATTTGTCCCTC-3' (SEQ ID NO: 16) |

Effect of Paclitaxel on Apoptosis

The percentage of early and late apoptotic cells was determined by using the ApoAlert Annexin Kit (BD Biosciences, Franklin Lakes, N.J., USA). Briefly, control and paclitaxel-treated cells were trypsinized and washed twice with PBS. Cells ($1\times10^6$/ml) were then resuspended in binding buffer, and 150 ml of the cell suspension was incubated with 5 ml of annexin cy5 and 10 ml of propidium iodide for 15 min in the dark at room temperature. The mixtures of cell solution were analysed by a flow cytometer (FACScan; BD Biosciences).

Surface Expression of Integrins and TG2

Viable cells (WT and two subclones) were detached with 2 mM EDTA and resuspended ($2\times10_5$ cells/100 ml) in 1% BSA in PBS, followed by incubation with 1 mg/100 ml of a primary antibody for 30 min on ice. After washing with PBS, cells were incubated with a fluorescein isothiocyanate-conjugated anti-mouse IgG secondary antibody (0.2 mg/100 ml) and analysed with the FACScan flow cytometer (Becton Dickinson). Isotypic control IgG and an appropriate fluorochrome conjugated secondary antibody was used in parallel as a control.

Immunoprecipitation

Four hundred micrograms of total cell lysate protein was used for the immunoprecipitation of integrins β1, β4 and β5 as described (Herman et al., 2006). Briefly, after preclearing and incubation with an appropriate antibody overnight, antigen-antibody complexes were removed by incubation with anti-mouse IgG or anti-rabbit IgG for 1 h at 4° C., followed by incubation with a G-protein sepharose beads (1-3 h at 4° C.). Beads were washed with the extraction buffer and eluted with a 2× sample buffer. Bound proteins were analysed by Western blotting. To detect TG2 in the immunoprecipitates (IPs), we first probed membranes with an anti-TG2 antibody (M-300, Neomarkers) before stripping and reprobing them with anti-β1-, anti-β4- or anti-β5-integrin antibodies.

Results

To test the hypothesis that TG2 expression plays a role in conferring metastatic phenotype to breast cancer cells, we used two MDA-MB23 1-derived sublines (MDA231/cl. 9 and MDA231/cl. 16) that were established on the basis of their differential expression of constitutive TG2 (Mehta et al., 2004). The MDA231/cl. 9 cells contained low TG2 levels, whereas MDA231/cl. 16 cells showed high constitutive expression of TG2 as determined by analysis of the enzymatic activity, by Western blotting and by immunofluorescent staining (FIG. 1).

Because increased cell motility is an important feature of metastatic breast cancer cells, we first compared MDA231/cl. 16 and MDA231/cl. 9 cells for their ability to migrate on Fn-coated surfaces. As shown in FIGS. 2*a* and *b*, TG2-expressing wild-type (WT) MDA-MB23 1 and MDA23 1/cl. 16 cells migrated far more in number and distance on Fn-coated plates than did the TG2-deficient MDA231/cl. 9 cells. On bovine serum albumin (B SA)-coated plates, however, none of the three cell types showed any significant migration (data not shown). Similarly, in an in vitro invasion assay, WT MDA-MB231 and MDA231/cl. 16 cells expressing high levels of TG2 showed prominent invasion through the Matrigel-transwell-coated membranes compared with the low TG2-expressing MDA231/cl. 9 cells (FIGS. 2*c* and *d*). These results suggest that TG2 expression plays a role in regulating cell migration and invasion functions.

Results of a reverse transcriptase-polymerase chain reaction (RT-PCR) assay to determine if TG2 expression is associated with upregulation of other known metastatic marker genes showed that despite TG2 expression, only the matrix metalloproteinase-1 (MMP-1) transcript was upregulated in invasive MDA231/cl. 16 and MDA-MB231 cells (FIG. 2*e*). Other known markers, such as osteopontin, CXCR4, interleukin-11 and connective tissue growth factor, showed no alteration in their transcript levels in the three MDA-MB231 cell lines. Moreover, RT-PCR analysis of the parental MDA-MB23 1 (WT) and its two sublines (cl. 9 and cl. 16) for the expression of other members of the TG2 family of enzymes (TG1, TG4, TG5, TG7) revealed no detectable expression for any of the known TGs (data not shown).

Because TG2 expression has been shown to promote cell adhesion (Verderio et al., 1998) and to serve as a coreceptor for integrin-mediated binding of cells to Fn (Zemskov et al., 2006), we tested whether TG2 expression in breast cancer cells can promote both the adhesion of cells to Fn and cell survival signaling. Indeed, TG2-expressing MDA23 1/cl. 16 cells showed strong attachment and spreading when cultured on Fn-coated surfaces; low TG2 expressing MDA231/cl. 9 cells under similar conditions were less adherent (FIG. 3*a*). On BSA-coated surfaces, however, both cell types were far less adherent and showed a rounded morphology.

We next determined whether TG2-mediated attachment of cells to Fn could confer protection from drug-induced cytotoxic effects. We found that TG2-rich MDA23 1/cl. 16 cells cultured on Fn-coated surfaces were more resistant to paclitaxel-induced cell death than were cells cultured on BSA-coated surfaces and that these cells were also more resistant than were MDA231/cl. 9 cells with low TG2 expression when cultured on Fn-coated surfaces (FIG. 3*b*). These results suggest that TG2 expression in cancer cells promotes cell surface interaction with Fn and protects cells from apoptosis. Indeed, it has been well documented that the interaction of cancer cells with Fn can induce cell survival signaling pathways and confer chemoresistance (Zhang et al., 1995; Damiano et al., 1999; Cordes et al., 2003).

Because cell surface TG2 is responsible for mediating the interaction of integrins with Fn by acting as a coreceptor for the extracellular matrix (ECM) ligand, when next determined the levels of cell surface TG2 and integrins in the parental and MDA-MB231 sublines. As shown in FIG. 4, cell surface expression of TG2 in MDA23 1/cl. 16 cells was three- to fivefold higher than in MDA23 1/cl. 9 cells and approximately twofold higher than in the parental MDA-MB23 1 cells. A comparison of the expression profiles of integrins in the three MDAMB23 1 cell lines did not show appreciable differences in β1, β5 and α5 expression. However, the expression of integrins β4, β6 and av was appreciably higher in TG2-rich (WT MDA-MB23 1 and MDA23 1/cl. 16 cells) than in TG2-low (MDA-MB231/1.9) cells (FIG. 4).

Results of a co-immunoprecipitation assay conducted to further delineate the link between TG2 and integrins clearly established an association between TG2 and integrins b1 (FIG. 5*a*) and b5 (FIG. 5*b*). Immunoprecipitation with either of the two β-integrin-specific antibodies pulled down TG2 protein and the respective integrin protein, as revealed by immunoblotting. A similar association of TG2 with integrin β4 was observed in MDA231/cl. 16 cells (data not shown). However, irrelevant antibodies, such as those directed against the epidermal growth factor receptor, failed to pull down TG2 (data not shown), suggesting a selective interaction between the integrins and TG2. The association between TG2 and integrins was further supported by confocal microscopy data. TG2 colocalized with integrin β1 (FIG. 5*c*) and integrin β5 (FIG. 5*d*) in WT MDA-MB231 and MDA23 1/cl. 16 cells, as suggested by the yellow fluorescence in the merged images.

We next determined the involvement of TG2 in Fn-mediated cell attachment, survival and invasion by using an siRNA approach (Herman et al., 2006). Transfection of MDA23 1/cl. 16 cells with control siRNA (scrambled) had no appreciable effect on the TG2 levels. However, the two TG2-specific siRNAs (siRNA1 and siRNA2) blocked TG2 expression by 70-80%, as revealed by Western blotting (FIG. 6*a*), and enzymatic activity assay (data not shown). We next analysed the effect of transient knockdown of TG2 on Fn-mediated cell attachment. We found that inhibition of TG2 could effectively block the attachment of MDA23 1/cl. 16 cells to Fn-coated surfaces (FIGS. 6*b* and *c*). However, non-Fn-mediated adherence (e.g., to polylysine-coated surfaces) was not affected by the lack of TG2 expression. BSA-coated surfaces, on the other hand, failed to promote the attachment of either TG2-expressing or TG2-knockdown MDA23 1/cl. 16 cells (data not shown). These results further suggest that TG2 expression selectively promotes the Fn-mediated attachment of cells.

After a 48-h incubation of untreated and siRNA-transfected cells in serum-free medium in Fn-coated plates, the ability of TG2 and Fn to support cell growth and cell survival functions was determined under serum-free culture conditions by the crystal violet-staining assay. TG2-rich MDA231/cl. 16 cells cultured on Fn-coated surfaces survived and grew well under serum-free conditions (FIGS. 7*a* and *b*). However, these cells did not survive on BSA-coated surfaces (FIG. 7*b*). Importantly, knockdown of TG2 with siRNA markedly reduced the survival and growth of these cells, even when they were cultured on Fn-coated surfaces (FIG. 7*a*). These results suggest that the TG2-dependent interaction between breast cancer cells and Fn is critical for inducing cell growth and cell survival signaling.

In a parallel experiment, we also determined the effect of TG2 inhibition on the invasive functions of MDA23 1/cl. 16 by using Matrigel-coated transwell inserts. As observed previously (FIGS. 2*c* and *d*), TG2-rich MDA23 1/cl. 16 cells were highly invasive (FIG. 7*c*). However, the inhibition of TG2 by siRNA dramatically inhibited the cells' ability to invade through the Matrigel-coated transwell inserts (FIGS. 7*c* and *d*). Transfection with control siRNA did not alter this ability, suggesting that TG2 expression promotes invasive functions in breast cancer cells.

To further address the role of TG2 in promoting cell attachment and invasive functions, we overexpressed TG2 by infecting MDA231/cl. 9 cells with adenovirus-containing TG2 construct at 25 multiplicity of infection (MOI). As expected, the overall expression of TG2 in infected MDA231/cl. 9 cells increased by three- to fourfolds over the basal level as determined by Western blotting (FIG. 8*a*) and two- to threefold on the cell surface as determined by flow cytometry (FIG. 8*b*). Interestingly, forced expression of TG2 was associated with a parallel increase in the invasive potential of MDA23 1/cl. 9 cells (FIGS. 8*c* and *d*) and their ability to attach to Fn- and vitronectin-coated surfaces (FIG. 8*e*). Infection of cells with adenovirus vector alone had no effect on TG2 expression or cell adhesion and invasion. However, ectopic expression of a mutant TG2 that lacks transamidation activity owing to point mutation in the active site cysteine residue (C277S) resulted in a similar increase in cell attachment and invasion of MDA23 1/cl. 9 cells (data not shown). These results suggested that TG2 expression plays an important role in promoting the invasive phenotype in breast cancer cells and that the crosslinking activity of TG2 is not essential for conferring these functions.

Discussion

On the basis of the results reported here, we propose that TG2 expression in metastatic breast cancer cells can not only confer apoptosis-resistance phenotype by promoting integrin-mediated cell attachment and cell survival signaling pathways, but also promote the cell migration and invasion functions. In an independent study, Jiang et al. (2003a, b) observed that TG2 was one of the 11 metastasis-associated proteins that were selectively amplified in metastatic human lung and breast carcinomas, as revealed by proteomic analysis. Furthermore, these authors reported that tumor cells expressed significantly increased levels of transcripts of TG4 and TG7 compared with the normal mammary tissue. Our current study showed no detectable expression of TG1, TG4, TG5, or TG7 transcripts in meta static or non-metastatic MDA-MB23 1 cells. However, TG2 expression was selectively elevated in a metastatic MDA-MB231 subline (cl. 16). Moreover, TG2 is closely associated with β1-, β4-, and β5-integrins in metastatic MDA231/cl. 16 breast cancer cells and promotes their attachment and motility on Fn-coated surfaces. It is possible that this association of TG2 with cell-surface integrins can promote integrin-mediated cell signaling that could affect not only the adhesion, migration and invasive functions of these cells but also their survival and growth. Indeed, the selective knockdown of TG2 protein using siRNA strongly attenuated their adherence, survival and invasion through Matrigel-coated transwell filters (FIGS. 6 and 7). The siRNA-induced inhibition of endogenous TG2 did not alter the expression of cell-surface integrins or MMP-1, suggesting that integrins and MMP-1 requires the presence of TG2 to promote the cell attachment and invasive functions in MDA-23 1/cl. 16 cells. Moreover, ectopic expression of TG2 in MDA-23 1/cl. 9 cells rendered these cells invasive and adherent on Fn-coated surfaces (FIG. 8), thus further supporting a role for TG2 in these functions.

We earlier reported a similar increase in TG2 expression in drug-resistant breast cancer cells (Chen et al., 2002, 2004) and the association of TG2 with b integrins in these cells (Herman et al., 2006). On the basis of these observations and in view of the high-binding affinity of TG2 for Fn (Jeong et al., 1995; Hang et al., 2005), we anticipated that TG2 expression would promote the stable interaction of integrins with Fn, the major matrix ligand in the ECM. Indeed, the cell surface interaction with Fn mediated by the α5β1-integrin is an important mediator of cell survival signaling (Longtin, 2004). For example, the culture of α5β1-integrin expressing cells on Fn is associated with increased expression of the antiapoptotic protein Bcl2 and thus protects these cells from apoptosis (Zhang et al., 1995). Similarly, several cancer cell lines have been shown to better survive chemotherapy or radiation-induced cell death when cultured on Fn-coated surfaces (Damiano et al., 1999, 2001; Aoudjit and Vuori, 2001; Cordes et al., 2003; Korah et al., 2004). The crosstalk between the cell surface α5β1-integrin and Fn leads to the activation of signaling pathways that can induce cell growth and contribute to the development of the metastatic phenotype (Parise et al., 2000; Mehlen and Puisieux, 2006).

It has been shown that the activation of Shc in response to the interaction of α5β1 and Fn modulates the adhesion and motility of breast cancer MCF-7 cells (Mauro et al., 1999) and that this interaction also results in the activation of Cdc42 and Rac-like GTPases known to contribute to the cell attachment, motility and invasion of cancer cells (Price et al., 1998). A more recent study demonstrated the direct involvement of cell surface TG2 in integrin-mediated signaling to RhoA/ROCK via integrin clustering and downregulation of the src-p 1 90 RhoGAP regulatory pathway (Janiak et al., 2006). These observations may explain the role of cell surface TG2 in promoting cellular adhesion, cytoskeletal organization, migration, and matrix assembly. Similarly, the association of TG2 with a b4 partner in metastatic breast cancer cells may activate α6β4-mediated signaling and affect their migration, invasion, and survival functions (Lipscomb and Mercurio, 2005).

On the other hand, the high expression of TG2 in metastatic breast cancer cells may explain their higher apoptotic threshold, an important characteristic of metastatic cancer cells that enables them to withstand not only the microenvironmental stresses such as hypoxia, nutritional depletion, and low pH but also any chemotherapy-induced cytotoxic effects (Mehlen and Puisieux, 2006). Indeed, the results reported here supported such a contention by demonstrating the increased resistance of TG2-rich MDA23 1/cl. 16 cells to paclitaxel compared with low TG2-expressing MDA231/cl. 9 cells (FIG. 3*b*). A similar resistance to paclitaxel-induced cytotoxicity has been reported by Aoudjit and Vuori (2001) in MDA-MB23 1 cells cultured on Fn-coated surfaces. Notably, the inhibition of TG2 protein by siRNA rendered the cells sensitive to apoptosis under serum-free conditions (FIG. 7*b*). Similarly, inhibition of TG2 expression by siRNA or an antisense approach has been shown to reverse the sensitivity of drug-resistant breast cancer MCF-7 (Herman et al., 2006) and of lung cancer PC-14 cells (Han and Park, 1999) to chemotherapeutic drugs. Moreover, the culture of TG2-positive cells on Fn-coated surfaces has been shown to induce strong activation of the focal adhesion kinase (Belkin et al., 2005; Herman et al., 2006), an upstream event that leads to the activation of various downstream antiapoptotic and cell survival signaling pathways (Sonoda et al., 2000; McLean et al., 2005).

In addition to their increased resistance to apoptosis, metastatic cells also acquire an increased ability to migrate and invade. This study further revealed that TG2 expression contributed to the increased ability of TG2-rich MDA231/cl. 16 cells to migrate and invade through the Matrigel-coated transwells compared with low TG2-expressing MDA-23 1/cl. 9 cells (FIG. 2). Notably, the downregulation of TG2 by siRNA significantly inhibited the ability of MDA-23 1/cl. 16 cells to attach to Fn-coated surfaces (FIG. 6*b*) and invade through the Matrigel transwells (FIGS. 7*c* and *d*). A similar role for TG2 in promoting migration in normal cells has been documented by several recent reports. The first suggested that inhibition of TG2 could block the transmigration of T-lymphocytes across interferon-treated and tumor necrosis factor-a-treated endothelial cells (Mohan et al., 2003). In the second study, the authors observed that the transforming growth factor b-induced increase in the cell surface expression of TG2 was responsible for augmenting the attachment and migration of retinal pigment epithelial cells on Fn-coated surfaces (Priglinger et al., 2004). Moreover, retinoic acid-induced TG2 expression in neuroblastoma SH-SY5 cells strongly augmented their migration and invasion functions (Joshi et al., 2006). The authors concluded that in addition to TG2 some other factor(s) was needed to promote retinoic acid-induced migration and invasion because inhibition of TG2 by antisense blocked these functions, but overexpression of TG2 in untreated cells failed to induce any change. Further-more, Hox A 7-mediated downregulation of TG2 was recently shown to inhibit the interaction and migration of differentiated HL-60 cells on Fn-coated surfaces (Leroy et al., 2004). These observations and our current findings clearly suggest that TG2 expression promotes the cell migration and invasion functions in breast cancer cells. It is possible that alterations such as the constitutive activation of small GTPase RhoA caused by the transamidation reaction catalysed by cytoplasmic TG2 (Singh et al., 2001) or the integrin aggregation induced by cell surface TG2 (Janiak et al., 2006) alter cytoskeletal organization and contribute to the increased ability of TG2-expressing metastatic cells to adhere and migrate. A further understanding of TG2-mediated cellular interactions with the ECM and signaling pathways induced in response to such an interaction may offer new targets for intervention and treatment of metastatic cancer.

Example 2

Protein Kinase C-Delta (PKCδ) Protects Pancreatic Cancer Cells from Autophagy by Upregulating Tissue Transglutaminase (TG2) Expression Materials and Methods Cell Lines, Culture Conditions and Reagents Pancreatic cell lines MDA-Panc28, Capan-2, Bx-PC3, Panc1 and MIAPaCa were provided by Dr. Shrikant Reddy (M. D. Anderson Cancer Center). MDA-Panc28 and Bx-PC3 cell lines were maintained in RPMI-1640 medium supplemented with 10% fetal calf serum. Panc1 and MIAPaCa cell lines and Capan-2 cells were maintained in DMEM and McCoy's 5A, respectively. All media were supplemented with 10% fetal calf serum. For the cell proliferation experiments, cells were seeded at a density of 1-2×$10^5$ cells in T-25 tissue culture flasks. Twenty-four hours after the seeding, cells were treated with various concentrations of rottlerin for the indicated periods of time. Adherent cells were collected by trypsinization, and cell numbers were determined using a Neubauer cell counting chamber. All experiments were replicated at least two times.

Western Blot Analysis

After treatment, the cells were collected and centrifuged, and whole-cell lysates were obtained using a lysis buffer. Total protein concentration was determined using a DC protein assay kit (Bio-Rad, Hercules, Calif., USA). Rottlerin and mTOR inhibitor (rapamycin) were purchased from Calbiochem (La Jolla, Calif., USA). Aliquots containing 30 μg of total protein from each sample were subjected to sodium dodecyl sulfate-polyacrylamide gel electrophoresis (SDS-PAGE) with a 4-20% gradient and electrotransferred to nitrocellulose membranes. The membranes were blocked with 5% dry milk in tris-buffered saline-tween 20 (TBST), probed with primary antibodies diluted in TBST containing 2.5% dry milk and incubated at 4° C. overnight. We used primary antibodies against PKCδ and p-mTOR (Ser-2448) from Cell Signaling Technology (Beverly, Mass., USA), TG2 antibody from Neomarker (Fremont, Calif., USA). Anti-LC3 antibody against a synthetic peptide corresponding to the N-terminal 14 amino acids of the isoform B of human LC3 and an additional cysteine (PSEKTFKQRRTFEQC) was prepared by immunization of a rabbit and affinity purified on an immobilized peptide-Sepharose column (Covance, Denver, Pa.). After being washed, the membranes were incubated with horseradish peroxidase-conjugated anti-rabbit or anti-mouse secondary antibody (Amersham Life Science, Cleveland, Ohio, USA). Mouse anti-β-actin and donkey anti-mouse secondary antibody were purchased from Sigma Chemical (St. Louis, Mo., USA) so that β-actin expression could be monitored to ensure equal loading of proteins. Chemiluminescent detection was performed with Chemi-glow (Alpha Innotech, San Leandro, Calif., USA) detection reagents. The blots were visualized with a Fluor Chem 8900 imager and quantified by a densitometer using the Alpha Imager application program (Alpha Innotech). All experiments were independently repeated at least twice.

RNA Isolation and RT-PCR Analysis

Cells were collected for isolation of total RNA. Total cellular RNA was isolated with Trizol reagent (Invitrogen/Life Technologies, Carlsbad, Calif., USA), and cDNA was obtained from 5 μg of total RNA using a Superscript II RT kit (Invitrogen/Life Technologies). Briefly, 5 μl of the total 20 μl of reverse-transcribed product was used for PCR in 1×PCR buffer containing 1.5 mM $MgCl_2$, 250 μM dNTPs, 0.5 units of Taq polymerase (Invitrogen/Life Technologies), and 100 ng of TG2 primer (primer 1,5'-TATGGCCAGTGCTGGGTCT-TCGCC-3'; primer II, 5'-GGCTCCAGGGTTAGGTT GAG-CAGG-3') or β-actin-specific primer (Sigma-Genosys, Houston, Tex., USA). Thirty cycles were used for PCR analysis. The reaction products were analyzed on a 2% agarose gel containing ethidium bromide, and cDNA synthesis was verified by detection of the β-actin transcript, which was used as an internal control.

Evaluation of Acidic Vesicular Organelles

To detect and quantify acidic vesicular organelles, cells were stained with acridine orange as described previously. The number of acridine orange-positive cells was determined by fluorescence-activated cell sorting (FACS) analysis. Cell morphology was examined using phase-contrast and fluorescence microscopy (Nikon, Melville, N.Y., USA) with the cells remaining in their culture flasks.

Transfections with siRNA and GFP-LC3 Plasmid

Exponentially growing untreated MDA-Panc28 cells were plated 24 h before transfection. Plated cells were transfected with double-stranded siRNA targeting TG2 mRNA and control (non-silencing) siRNA (all from Qiagen, Venlo, Netherlands) and/or the green fluorescent protein (GFP) and microtubule-associated protein 1 light chain 3 (LC3) fusion vector (GFP-LC3) using the Qiagen transfection reagent according to the manufacturer's protocol. Two siRNA sequences targeting TG2 were designed using siRNA-designing software (Qiagen). PKCδ siRNA was obtained from Santa Cruz Biotechnology (Santa Cruz, Calif., USA). Untransfected cells and non-silencing control siRNA-transfected cells were used as negative controls. After treatment, the cells were harvested for western blot analysis or FACS analysis to determine whether autophagy had occurred.

Results

Inhibition of PKCδ Results in Downregulation of TG2

As a first step to elucidate the relationship between PKCδ and TG2 expression in pancreatic cancer cells, we determined the effect of a PKCδ-specific inhibitor, rottlerin, on constitutive expression of TG2 in MDA-Panc28 pancreatic ductal carcinoma cells (FIG. 9*a*). Treatment of MDA-Panc28 cells with 2 μM rottlerin inhibited PKCδ protein expression by 72% and treatment with 4 μM rottlerin inhibited expression by 94%. Notably, rottlerin also caused a dose-dependent inhibition in the cells' TG2 protein expression. As little as 1 μM rottlerin inhibited TG2 expression by 44%, with maximum inhibition (94%) seen at the 4 μM dose after 48 h of treatment. Reverse transcriptase polymerase chain reaction (RT-PCR) analysis of treated and untreated cells confirmed the inhibitory effect of rottlerin on TG2 expression at the level of transcription (FIG. 9*b*). Rottlerin has been shown to block PKCδ specifically at concentrations between 3 and 6 μM. However, at higher concentrations it can also inhibit other isoforms of PKC. On the basis of these observations, we conclude that the effects of rottlerin on cell growth and TG2 expression are mediated by the selective inhibition of PKCδ.

Rottlerin Induces Inhibition of Cell Growth in Pancreatic Cancer Cells

We next determined the growth inhibitory effect of rottlerin in several pancreatic cancer cell lines, including Bx-PC3, MIAPaCa, MDA-Panc28, Panc1, and Capan-2 (FIG. 10*a*). Treatment of cells with rottlerin (4 μM for 48 h) induced growth inhibition in all five cell lines tested. We also determined the time course of rottlerin-induced growth inhibition in MDA-Panc28, Bx-PC3, and MIAPaCa cell lines and found a time-dependent inhibition in cell growth of all three (FIG. 10*b*).

Rottlerin-Induced Growth Inhibition is Independent of Apoptosis

To determine the mechanism of rottlerin-induced cell growth inhibition, we determined the extent of apoptosis induced in response to rottlerin in MDA-Panc28 cells. Under optimal conditions (4 μM rottlerin treatment for 48 h), even though rottlerin induced a 49% inhibition in cell growth, it failed to promote any apoptosis in MDA-Panc28 cells, as revealed by the failure of cells to accumulate in the sub-G, phase (FIG. 11*a*). Moreover, rottlerin-treated cells failed to show any poly ADP-ribose polymerase (PARP) cleavage (FIG. 11*b*) further supporting the contention that rottlerin-induced inhibition in cell growth in pancreatic cancer cells was independent of apoptosis. Morphologic changes induced by rottlerin in MDA-Panc28 cells are shown in FIG. 11*b*. After 48 h of treatment, cells appeared to lose cell-to-cell contact and became rounded and the cytoplasmic vacuoles started to become apparent (FIG. 11*c*, middle panel) when compared with untreated controls (FIG. 11*c*, left panel). After 96 h of treatment, extensive vacuolization with some cell damage started to become evident (FIG. 11*c*, right panel).

Downregulation of TG2 Induces Autophagy

We next determined the effect of rottlerin-induced downregulation of TG2 on accumulation of microtubule-associated protein 1 light chain 3-II (LC3-II) protein, a hallmark of autophagy. LC3, the homologue of the yeast Apg 8/Aut7p gene, localizes on the autophagosomal membrane during autophagy. Results shown in FIG. 12*a* demonstrated a significant increase in endogenous LC3-II accumulation in MDA-Panc28, Capan-2, Bx-PC3, Panc1, and MIAPaCa cells treated with rottlerin at a concentration of 4 μM for 48 h. In all pancreatic cancer cell lines tested, the rottlerin-induced increase in LC3-II protein was associated with a parallel decrease in TG2 expression (FIG. 12*a*). Therefore, we next elucidated the possible involvement of TG2 in rottlerin-induced autophagy. First, we determined whether rottlerin treatment induce autophagy in a TG2-negative tumor cell line, MCF-7. Treatment of MCF-7 cells with rottlerin under optimal conditions failed to produce any increase in LC3-II accumulation (FIG. 12*b*), indicating that the induction of autophagy by Rottlerin involved TG2.

One important finding was that knock-down PKCδ expression by a specific siRNA in MDA-Panc28 cells led to the downregulation of TG2 protein (FIG. 12*c*), further demonstrating that PKCδ regulates TG2 expression. We next determined whether TG2 mediates PKCδ-induced inhibition of autophagy. To determine whether TG2 is directly involved in the regulation of autophagy in MDA-Panc28 cells we knocked-down TG2 expression with siRNA specifically targeting TG2 mRNA. FIG. 12*c* shows that TG2 siRNA specifically down-regulates TG2 protein expression. We found that the inhibition of TG2 expression by rottlerin or by TG2 siRNA in MDA-Panc28 cells resulted in formation autophagic vacuoles by phase contrast microscopy (FIG. 12*d* left column), marked increase in number of acidic vesicular organelles detected by acridine orange staining in MDA-Panc28 cells (FIG. 12*d* center column) and accumulation of GFP-LC-II protein in autophagoseomes in GFP-LC3 plasmid transfected MDA-Panc28 cells (FIG. 12*d* right column). When autophagy is induced, LC3-II, a cleaved product of LC3, specifically localizes to the membrane of autophagosomes. Therefore accumulation of GFP-LC3 in the vacuoles following rottlerin and TG2 siRNA treatments indicates formation of autophagosomes and induction of autophagy in the cells. In control siRNA treated cells none of the changes were observed by any of the assays. Fluorescence microscopy (FIG. 12*d*, middle column) and flow cytometry (FIG. 12*e,f*) of rottlerin-treated or TG2-siRNA-transfected MDA-Panc28 cells stained with acridine orange revealed massive accumulation of acidic vesicular organelles representing formation of autophagosomes. Quantification of acidic vesicular organelles by flow cytometry revealed that the percentage of red fluorescein-positive cells in rottlerin-treated cells (64%) and TG2 knockdown cells (39%) was significantly higher than in the control cells (8%) (FIG. 12*e,f*).

These results further supported the observations that inhibition of TG2, either directly by siRNA transfection or indirectly by inhibition of PKCδ with rottlerin, induces the autophagic death in pancreatic cancer cells. Overall, these results suggest that the PKCδ regulates autophagy through expression of TG2 and PKCδ-induced increase in TG2 expression confers protection to the pancreatic cancer cells against autophagy.

PKCδ/TG2-Mediated Autophagy is Independent of the mTOR Pathway

Because mTOR (mammalian target of rapamycin) has been shown to regulate autophagy, we sought to determine whether rottlerin induces authophagy by inhibiting mTOR, as well as TG2. We found that rottlerin treatment downregulated phosphorylated mTOR (p-mTOR) (FIG. 13*a*) and p-p70S6K, a downstream target of mTOR, in MDA-Panc28 cells (data not shown). To further determine whether rottlerin-induced downregulation of mTOR was a cause of autophagy, we investigated the effect of rapamycin, a specific inhibitor of mTOR, in MDA-Panc28 cells. Rapamycin failed to induce autophagy in these cells (FIG. 13*b*) but downregulation of TG2 by a TG2 specific siRNA induced autophagy as observed in the previous experiments, indicating that rottlerin-induced autophagy is not mediated by mTOR. We also observed downregulation of p-p70S6K following exposure to rapamycin indicating that rapamycin was able to inhibit mTOR and its down stream target (data not shown).

Discussion

The present study provides first evidence that TG2 expression can regulate autophagy in pancreatic cancer cells. Our data demonstrate that PKCδ plays a critical role in the expression of TG2 and that increased expression of TG2 plays an important role in preventing pancreatic cancer cells from undergoing autophagy (FIG. 12).

The phosphatidylinositol 3-kinase (PI3K)-Akt-mTOR pathway, which is activated in many cancer types, has been shown to suppress autophagy in cancer cells. Rapamycin, an inhibitor of mTOR, induces autophagy. In the present study, we also found that inhibition of PKCδ by rottlerin was associated with downregulation of mTOR protein in MDA-Panc28 cells during the induction of autophagy. However, downregulation of mTOR by rapamycin did not result in autophagy, suggesting that the mTOR pathway, at least in the cells studied here, is not involved in autophagy. For instance, Beclin 1 protein functions as a stimulator of autophagy in breast cancer cells, and its inactivation in mice (Becn 1+/−) was found to markedly increase the incidence of tumors, including lung cancer, hepatocellular carcinoma and lymphoma. To eliminate the possibility that Beclin 1 plays a role in autophagy that is induced by downregulation of PKCδ and TG2, we examined Beclin 1 expression in response to rottlerin. Expression levels did not change, indicating that Beclin 1 does not mediate the autophagy observed in MDA-Panc28 cancer cells (data not shown).

Results from previous studies suggest that TG2 can exert both pro- and anti-apoptotic effects, depending on the cell type. TG2 expression is upregulated in various types of cancer cells, and it has been implicated in resistance to stress-induced apoptosis. However, in some cell lines among them leukemia, cervical adenocarcinoma and neuroblastoma cell lines, TG2 expression has been shown to facilitate the induction of apoptosis. Inhibition of TG2 by stable transfection with antisense or transient transfection with siRNA has been shown to restore sensitivity of cancer cells to chemotherapeutic drugs. These observations suggest that TG2 expression contributes to cellular resistance to chemotherapy. Furthermore, lymph node metastases from breast cancers were found to express significantly higher levels of TG2 than the primary tumors, suggesting that TG2 is involved in increasing the metastatic potential of breast cancer cells.

Example 3

Increased Expression of Tissue Transglutaminase in Pancreatic Ductal Adenocarcinoma and its Implications in Drug Resistance and Metastasis Materials and Methods Materials The rabbit polyclonal antibodies to pAKT (Ser473), AKT, pERK1/2, and ERK1/2 were from Cell Signaling Technology (Beverly, Mass.). Mouse monoclonal antibodies to pY397 FAK and FAK were purchased from BD Biosciences Pharmigen (San Diego, Calif.). Anti-TG2 mAb CUB7401 was purchased from Neomaker (Fremont, Calif.). Anti-β-actin antibody was from Sigma Chemical Co. (St. Louis, Mo.), and the goat anti-rabbit and sheep anti-mouse horseradish peroxidase were purchased from Amersham Biosciences (Piscataway, N.J.). Trublot anti-mouse Ig IP beads were from eBiosciences (San Diego, Calif.). The cell fractionation kit was from Biovision, Inc. (Mountain View, Calif.). DMEM/F12, RPMI 1640, keratinocyte serum-free medium, bovine pituitary extract, recombinant human epidermal growth factor, fetal bovine serum, and Normocin antibiotic were all purchased from Invivogen (San Diego, Calif.).

The PDAC cell lines AsPC-1, MiaPaCa-2, Panc-1, HPAF-II, Hs766T, Capan-1, Capan-2, and BxPC-3 were provided by Dr. Shrikanth A. Reddy (The University of Texas M. D. Anderson Cancer Center, Houston, Tex.). Panc-28, Panc-02-3, Panc-48, and Su8686 cell lines were provided by Dr. Paul J. Chiao (M. D. Anderson Cancer Center). All cell lines were maintained in the log phase of cell growth by being cultured in RPMI 1640 or DMEM/F12 medium supplemented with fetal calf serum (10%, v/v), Normocin (0.1 mg/mL), L-glutamine (2 mM), and HEPES (10 mM; USB, Cleveland, Ohio) at 37° C. in a $CO_2$ incubator. The immortalized pancreatic ductal epithelium cell line (E6E7) was provided by Dr. Ming Tsao (Ontario Cancer Institute, Toronto, Ontario, Canada) and cultured in keratinocyte serum-free medium supplemented with bovine pituitary extracts, human epidermal growth factor, and FCS.

TG2 Enzymatic Activity

Cells at 70% to 80% confluence were washed in PBS and collected in a minimal volume of the lysis buffer (20 mM Tris-HCl [pH 7.4] containing 1 mM EDTA, 150 mM NaCl, 14 mM 2-mercaptoethanol, and 1 mM phenylmethylsulphonyl fluoride). Cells were then lysed in the same buffer by probe sonication and assayed for TG2 activity by determining the $Ca^{2+}$-dependent incorporation of [$^3$H]putrescine (specific activity, 14.3 Ci/mmol; Amersham-Pharmacia, San Francisco, Calif.) into dimethylcasein, as previously described. The enzyme activity was expressed as nanomoles of putrescine incorporated per milligram of total cell protein.

Western Blotting

Cells were serum-starved for 12-16 hours prior to the experiment. The whole-cell lysate (60 μg) or fractions thereof (prepared using the Biovision cell fractionation kit according to the manufacturer's protocol) were fractionated by 4-15% gradient SDS-PAGE. After SDS-PAGE, the proteins were electrotransferred onto nitrocellulose membranes, blotted with each antibody, and detected with enhanced chemiluminescence reagent (Amersham). Some of the membranes were stripped using Restore stripping buffer (Pierce, Rockford, Ill.) for reprobing with another antibody. The protein bands obtained were quantified using AlphaEase FC (Fluor Chem 8900) software from Alpha Innotech (San Leandro, Calif.).

Immunoprecipitation

Cells were lysed in a minimum volume of Tris-HCl buffer (50 mM, pH 8) containing 150 mM NaCl and 1% NP40 and precleared by incubation with 50 μL of Trublot anti-mouse Ig IP beads for 1 hour at 4° C. The pellet was discarded, and the supernatant was subjected to immunoprecipitation: 200 μg of cell lysate was incubated with 2 μg of specific antibody for 1 hour at 4° C. Twenty microliters of Trublot anti-mouse Ig IP beads was added, and the pellet was further incubated on a rotating device overnight at 4° C. The pellet was then washed four times in ice-cold lysis buffer. The supernatant was discarded, and the pellet was resuspended in 50 μL of the sample buffer. The samples were fractionated by SDS-PAGE and analyzed by immunoblotting and autoradiography.

Cytotoxicity

The number of viable cells remaining after the appropriate treatment was determined by measuring their ability to reduce 3-(4,5-dimethylthiazol-2-yl)-5-(3-carboxymethoxyphenyl)-2H-tetrazolium (MTS) into a soluble formazan in accordance with the manufacturer's instructions. Logarithmically growing cells were plated at $2\times10^3$ cells per well in 96-well plates and allowed to adhere overnight. They were then cultured alone or with 0.1 nM to 100 μM of gemcitabine for 24, 24, or 72 hours. Each experiment was repeated three times in triplicate. The concentration of gemcitabine required to inhibit proliferation by 50% ($IC_{50}$) was calculated. Under identical conditions, the cells were trypsinized, and the cell viability was determined with a trypan blue exclusion test to confirm the MTS results.

In Vitro Invasion

The invasive potential of PDAC cell lines was studied in vitro by determining the number of cells that invaded through Matrigel-coated Transwell polycarbonate membrane inserts, as described previously. In brief, Transwell inserts with a pore size of 12 μm were coated with 0.78 mg/mL Matrigel in serum-free medium. Cells were recovered by trypsinization, washed and resuspended in serum-free medium, and 0.5 mL of the cell suspension ($0.5\times10^6$ cells) was added to duplicate wells. After incubation for 48 hours, the cells that passed through the filter were stained using a Hema-3 stain kit (Fisher Scientific, Houston, Tex.). The cells in 10 random fields were counted under a microscope.

Wild-Type and $C_{277}S$ Mutant TG2 Adenovirus

An adenovirus containing wild-type (TG2wt) or $C_{277}S$ mutant TG2 (TG2m) cDNA was kindly provided by Dr. Ugra Singh (The University of Texas at temple, TX). In brief, TG2 cDNA cloned in pcDNA3.1 vector was first subcloned in a pshuttle 2 vector and then in a BD adenoX adenoviral vector. HEK293 cells were transfected with recombinant adenoviral plasmid for packaging of adenovirus particles. The adenovirus was purified on a CsCl2 gradient and used at 25 MOI. Cells infected with lacZ adenovirus served as the control.

TG2 Downregulation by siRNA

Two TG2 siRNA sequences were designed and purchased from Qiagen (Germantown, Md.). A sequence that did not have homology to any human mRNA (as determined by a BLAST search) served as a control, whereas two sequences were designed to target TG2 mRNA, siRNA1 (target sequence, 5'-AAGGCCCGTTTTCCACTAAGA-3' (SEQ ID NO:19)) and siRNA2 (target sequence, 5'-AAGGGCGAACCACCTGAACAA-3' (SEQ ID NO:20)). For transfection, $2\times10^5$ cells were plated in each well of six-well plates and allowed to adhere for 24 hours. On the day of transfection, 30 μL of RNAiFect transfection reagent (Qiagen, Germantown, Md.) was added to 5 μL of siRNA (1 μg/μL) in a 65-μL culture medium to give a final volume of 100 μL. The siRNA/transfection reagent mixture was incubated at ambient temperature for 15 minutes and added uniformly to plates in serum-containing media. After 48 hours of transfection, cells were recovered and used for appropriate determinations. The transfection efficiency was determined by transfecting cells in a parallel well with fluorescent siRNA and determining fluorescence uptake under the microscope.

Confocal Microscopy

To determine the co-localization of pFAK and TG2, cells were grown on glass coverslips and fixed in 4% paraformaldehyde for 20 minutes at ambient temperature. Fixed cells were then incubated with the primary antibodies overnight, washed with PBS, and incubated again with secondary antibodies conjugated with either Alexa 546 (red) or 488 (green) (Molecular Probes, Eugene, Oreg.). The DNA dye Topro-3 (Molecular Probes) was used to co-stain the nuclei (blue). Cells treated with secondary antibodies alone were used as controls. A confocal scanning analysis of the cells was performed with a Zeiss laser scanning confocal microscope (Carl Zeiss MicroImaging, Inc., Thornwood, N.Y.) or an Olympus FluoView 300 confocal microscope (Center Valley, Pa.) in accordance with established methods, using sequential laser excitation to minimize the fluorescent emission bleed through. Each section was examined for the presence of each stain at two excitations (546 nm and 488 nm), and the data were compared pixel by pixel. Each image represented z sections at the same cellular level and magnification; a three-dimensional reconstructed image was used to visualize the whole sample. Merging red and green showed co-localization of two proteins, giving a yellow color.

Immunohistochemistry

Samples used in this study were from patients with primary pancreatic ductal adenocarcinoma who underwent initial pancreaticoduodenectomy at our institution between 1990 and 2004. None of these patients received pre-operative chemotherapy or radiation before surgery. A total of 75 such patients were identified for whom tissue samples and follow-up information were available. Patients' clinicopathologic data were collected and follow-up data was updated through Dec. 31, 2005 by reviewing medical records and the U.S. Social Security Index. The use of archival paraffin-embedded tissue blocks and chart reviews were approved by the Institutional Review Board Committee of M. D. Anderson Cancer Center. Tissue microarrays were constructed using formalin-fixed, paraffin-embedded archival tissue blocks from these 75 pancreatic ductal adenocarcinomas using the method as described previously. The H & E stained slides were reviewed and screened for most representative areas of the tumor and their matched paraffin blocks were retrieved. Each tumor and adjacent benign pancreatic tissue were sampled in duplicate with 1.0 mm tissue cores to include two tissue cores from the tumor and two tissue cores from the paired benign pancreatic tissue. In addition, nine different human pancreatic adenocarcinoma cell lines were also included to serve as controls.

TG2 expression levels in tumor samples were evaluated by an indirect immunoperoxidase procedure (ABC-Elite; Vector Laboratories, Burlingame, Calif.). In brief, antigen retrieval was performed by treating the tissue samples in a steamer for 30 minutes. 0.5 μg/ml antibody against TG2 (CUB7401, Neomarkers, Fremont, Calif.) overlaying the tissue section was incubated at 4° C. for 16 hours. The secondary antibody incubation was performed at ambient temperature for 1 hour. Mayer's hematoxylin nuclear stain was used as a counterstain. Immunostaining results were evaluated and scored independently by a pathologist and laboratory personnel. TG2 expression in tumor cells was categorized as negative (low or weak cytoplasmic staining) or positive (diffuse moderate to strong cytoplasmic staining).

Statistical Analysis

The clinicopathologic and follow-up data were correlated with TG2 expression. The statistical analysis was performed using Fisher's exact test and student t-test with SPSS software (version 12 for Windows; SPSS, Chicago, Ill.) and a P value of <0.05 was considered significant.

Results

TG2 Expression is Associated with Gemcitabine Resistance and Increased Invasive Potential Western blot analysis revealed elevated expression of the TG2 protein in all 12 PDAC cell lines tested. However, no TG2 was detected in immortalized pancreatic ductal epithelial cells (E6E7) (FIGS. 1 A and B). Interestingly, BxPC-3 and HPAF-II cell lines, which represent the well-differentiated and relatively less aggressive PDAC cell lines, expressed lower TG2 levels than did the aggressive and undifferentiated Panc-28, Capan-2, and AsPc-1 cell lines.

On the basis of our earlier observations that elevated TG2 expression in cancer cells contributes to the development of the drug-resistant phenotype, we next determined whether TG2 expression in PDAC cells is related to gemcitabine resistance. We used three cell lines, Panc-28, MiaPaCa-2, and BxPC-3, which expressed different basal levels of TG2 protein (FIG. 16A). Panc-28 cells expressed highest basal level of TG2 protein and activity, followed by MiaPaCa-2 and BxPC-3 cells (P<0.05) (FIG. 16A). The ability of gemcitabine to inhibit cell growth of these cell lines was inversely related to the level of TG2 expression (FIG. 16B). The high TG2-expressing Panc-28 cells showed minimal sensitivity to the gemcitabine-induced growth inhibition, as determined by the MTS cell viability assay. The $IC_{50}$ of gemcitabine for Panc-28 cells was one log higher (1 μM) than that for MiaPaCa-2 cells ($IC_{50}$=0.1 μM; P=0.02) and approximately two logs higher than that for TG2-deficient BxPC-3 cells ($IC_{50}$=0.01 μM; P=0.001).

We next determined whether the level of TG2 expression in PDAC cells affected their invasive potential. The three cell lines that constitutively expressed different levels of TG2 (FIG. 16A) were compared for their ability to invade through Matrigel-Transwell membranes. Results shown in FIG. 16C suggested that high TG2-expressing Panc-28 cells are 3 to 4-fold more invasive than the low-TG2 expressing MiaPaCa-2 and BxPC-3 cells (P=0.0002).

To further confirm the observation that TG2 overexpression increased the invasive potential and confer resistance to gemcitabine in PDAC cells, we overexpressed the wild-type (TG2wt) and catalytically inactive (TG2m) mutant of TG2 in BxPC-3 cells. TG2m lacks transamidation activity because of a point mutation in the active-site cysteine residue ($C_{277}S$). The results shown in FIGS. 3A and 3B suggested that overexpression of either TG2wt and TG2m strongly promotes the invasive potential of BxPC-3 cells. Moreover, BxPC-3 cells infected with TG2wt adenoviral construct became significantly more resistant to gemcitabine-induced cytotoxicity when compared with the adenovirus alone-infected cells (IC50=0.1 μM, P=0.03) (data not shown). Together, these results suggested that overexpression of TG2 contributes not only to gemcitabine resistance, but also to the invasive potential of PDAC cells, which was independent of its transamidation activity.

TG2 Induces Activation of FAK and PI3K/AKT Pathways

FAK is a nonreceptor tyrosine kinase that is activated by integrin clustering and transmits adhesion-dependent signals to promote growth, survival, and invasive functions in cells. Our previous studies using breast cancer and melanoma cancer cells demonstrated an association between TG2 and β integrins. Therefore, in this study, we determined the significance of TG2 expression in regulation of FAK functions. First, we compared the FAK basal activity in serum-starved Panc-28, MiaPaCa-2, and BxPC-3 cells, which expressed different levels of TG2. The results, shown in FIG. 17C, demonstrate a direct association between levels of TG2 expression and constitutive FAK activation (phospho [$pY^{397}$]). Panc-28 cells with high basal expression of TG2 had high levels of activated FAK, whereas FAK activation was lower in MiaPaCa-2 and BxPC-3 cells which had low TG2 expression (FIGS. 3C and 3D). Confocal microscopic analysis further supported these observations and revealed active form of FAK at focal adhesion points in TG2-rich Panc-28 cells than in low TG2-expressing MiaPaCa-2 and BxPC-3 cells (FIG. 17E). The Western blot and confocal microscopic analyses showed no significant difference in total FAK expression in Panc-28, MiaPaCa-2, and BxPC-3 cells (FIGS. 3C and 3E). These results suggest that TG2 is associated with activation of FAK in PDAC cells.

To further delineate the relationship between TG2 and FAK, we overexpressed TG2 by infecting BxPC-3 cells with 25 MOI of an adenovirus-containing TG2 wild type (TG2wt) construct. As expected, TG2 expression in infected BxPC-3 cells increased by 10-12-fold over the basal level, as determined by Western blotting and confocal microscopy (FIGS. 18A and C). Overexpression of TG2 was associated with a parallel increase in the enzyme activity (FIG. 18B) and constitutive activation of FAK in BxPC-3 cells. The infection of cells with adenovirus vector alone had no effect on TG2 expression or FAK activation. Interestingly, overexpression of TG2m, which lacks the enzyme activity, also resulted in an increase in FAK activation similar to that induced by TG2wt (FIGS. 18A and B). These results suggested that TG2-mediated activation of FAK occurs independent of its transamidation activity. This was further supported by confocal microscopy data (FIG. 18C). Interestingly, the TG2-mediated activation of FAK was associated with an increase in the co-localization of TG2 with pFAK at the focal adhesion points (FIG. 18C).

Because FAK activation results in the activation of the downstream PI3K/AKT and RAS/MEK/ERK pathways, we next determined the effect of TG2 expression on these pathways. Western blot analysis of untreated BxPC-3 cells or BxPC-3 cells infected with either TG2wt or TG2m showed marked increase in pAKT (Ser473) in infected cells (FIG. 18A). However, no change in the levels of phosphorylated ERK 1/2 was observed in TG2-infected or untreated cells (data not shown). These results suggest that TG2 expression, independent of its transamidation activity, can result in constitutive activation of FAK/PI3K/AKT pathway and promote the invasive function of PDAC cells.

Downregulation of TG2 Inhibits FAK Activation

To further determine the role of TG2 in FAK activation, we used siRNA approach to downregulate the endogenous expression in Panc-28 cells. As reported previously, siRNA1 and siRNA2 caused 80-90% inhibition of endogenous TG2 protein expression in Panc-28 cells (FIG. 19A). The downregulation of TG2 expression by siRNA resulted in inactivation of FAK (FIG. 19A). However, transfection of Panc-28 cells under similar conditions with control siRNA did not alter either TG2 expression or FAK activation (FIG. 19A). Downregulation of TG2 in Panc-28 cells also resulted in marked morphologic changes by light microscopy (FIG. 19B): the cells appeared more cylindrical in shape and segregated than were untreated controls. More importantly, the inhibition of endogenous TG2 by siRNA induced massive cytoplasmic vacuolization after 48 hours of transfection (FIG. 19B), and the cells eventually died. Also, the downregulation of endogenous TG2 was associated with a profound inhibition of Panc-28 cells to invade through Matrigel-Transwell membranes (data not shown). These results clearly demonstrated that TG2 expression plays a critical role in the constitutive activation of FAK and its downstream functions and that TG2 expression is critical for the survival of Panc-28 cells.

Association of TG2 with FAK

We further investigated the co-localization of TG2 with pFAK in PDAC cells. In a pull-down experiment, the immunoprecipitates of cell extracts from Panc-28, MiaPaCa-2, and BxPC-3 PDAC cells with an anti-FAK antibody revealed the presence of TG2 when the membranes were probed with anti-TG2 antibody (FIG. 20A). The association of TG2 with FAK in PDAC cells was further confirmed by reverse coimmunoprecipitation using an anti-TG2 antibody and probing with a FAK antibody (data not shown). We found no appreciable difference in total FAK expression in Panc-28, MiaPaCa-2, and BxPC-3 cells. However, Panc-28 cells which expressed high pFAK and TG2 also showed higher degree of association between TG2 and pFAK than did the MiaPaCa-2 and BxPC-3 cells (FIG. 20A). These results suggested that a direct association between TG2 and FAK may play a role in constitutive activation of FAK.

To further delineate the role of TG2 FAK activation, we determined the localization of TG2 with FAK in soluble and membranous cellular compartments. Membranous and cytosolic fractions from Panc-28 cells were immunoprecipitated with either anti-TG2 or anti-FAK antibody and probed with both antibodies. The results, shown FIG. 20B, demonstrate that approximately 80% of the total TG2 protein was present in the cytosolic fraction and 15% was in the membrane. Notably, the fraction of TG2 bound with FAK was higher in the membrane fraction (77%) than in the cytosolic fraction (33%) (FIG. 20B). Because activated FAK is mainly localized in the cytoplasmic membrane, we speculated that TG2 in the membrane was associated with the phosphorylated form of FAK. This contention was supported by the results of immunoprecipitation of Panc-28 cell extracts with an anti-pFAK ($pY^{397}$) antibody. As shown in FIG. 20C, TG2 is indeed associated with pFAK. The results of a confocal microscopy analysis (FIG. 20D) further supported the co-localization of TG2 with pFAK, particularly at the focal adhesion points. The co-localization of TG2 and pFAK at focal points was quantified in 40 cells, showing a mean number of 6.2 overlaps at focal points per cell. These results demonstrate, for the first time, that there is a direct association between TG2 and the signaling molecule FAK and that this association plays an important role in FAK activation.

TG2 Expression in PDAC Tumor Samples

To further evaluate the significance of our in vitro observations that TG2 expression results in gemcitabine resistance and invasive potential, we examined the expression levels of TG2 in a human tissue microarray containing 75 PDAC tissue samples. We found high basal levels of TG2 expression in 42 of the 75 (56%) tumor samples studied (FIG. 7A). However, only 24 of 70 cases (34%) showed cytoplasmic staining in benign pancreatic ducts. TG2 expression was significantly higher in PDACs compared with normal ducts (P=0.012). No staining was observed in sections treated with the isotypic control IgG instead of the primary anti-TG2 antibody (data not shown). High TG2 expression in tumor samples was significantly associated with nodal metastasis (32 out of 48 node positive tumor samples were TG2 positive versus 10 out of 27 node negative tumor sample, P=0.017, OR=3.400), lymphovascular invasion (33 of 51 lymphovascular invasive tumors were TG2 positive versus 9 of 24 non invasive tumors, P=0.045, OR=3.055), and clinical stage (30 of 45 stage IIb PDACs were TG2 positive versus 10 of 26 stage IIa tumors, P=0.027, OR=3.200). This data further supported our observations that TG2 overexpression increases the invasive potential of PDAC cell lines. A Kaplan-Meier estimate of survival in relation to TG2 expression showed no significant difference in TG2-positive (n=42) and TG2-negative patients (n=33) (P=0.159; FIG. 21B.

Discussion

Our data demonstrate that a significant majority of PDACs and PDAC cell lines express elevated levels of the multifunctional protein TG2. We provide the first evidence that TG2 is closely associated with FAK and results in its activation (pFAK) and activation of the downstream PI3K/AKT cell survival-signaling pathway. TG2 expression in PDAC cell lines was associated with increased resistance to gemcitabine and an invasive phenotype. Furthermore, we found significant association between TG2 expression and nodal metastasis, lymphovascular invasion and late clinical stage in PDAC tumor samples.

Previously, we found that constitutive expression of TG2 in drug-resistant and metastatic breast cancer and late-stage melanoma was upregulated. Importantly, downregulation of TG2 expression was associated with the increased sensitivity of cancer cells to apoptotic stimuli and reversal of the drug-resistant phenotype. Han and Park reported similar results in the drug-resistant lung cancer cell line PC-14/ADR. These authors showed that the acquisition of multidrug resistance in PC-14 cells was associated with a 10-15-fold increase in TG2 expression and that inhibition of TG2 expression by TG2-specific antisense or ribozyme rendered the cells sensitive not only to multidrug-resistance-related drugs but also to other anticancer drugs.

In this study, we determined the constitutive TG2 expression status of PDAC tumors and tumor cell lines. Of the 12 PDAC cell lines tested, 10 expressed high levels of TG2 protein, and two expressed moderate levels (FIG. 15). Importantly, 56% of the PDAC tumor samples showed elevated levels of TG2, which was associated with nodal metastasis, lymphovascular invasion, and late clinical stage. In cell lines, TG2 expression was associated with resistance to gemcitabine (FIG. 16B), a commonly used drug for the treatment of pancreatic cancer. Similarly, high TG2 expression was associated with invasive behavior (FIG. 16C). Thus, ectopic expression of TG2 in BxPC-3 cells rendered the cells highly invasive (FIG. 18D) and resistant to gemcitabine and conversely, the inhibition of TG2 by siRNA significantly attenuated the invasive potential of Panc-28 cells.

To delineate the possible mechanism by which TG2 could promote chemoresistance and invasive potential in PDAC cells, we studied the relationship between TG2 and FAK. TG2 has been shown to promote FAK activation via its ability to promote the integrin-mediated attachment of cells to fibronectin, a major component of the extracellular matrix in tumor microenvironments. FAK is a non-receptor cytoplasmic protein tyrosine kinase that provides signaling and scaffolding functions at sites of integrin adhesion. Ample evidence supports the role of FAK in cell adhesion, cell migration, and cell cycle progression. Increased FAK expression is frequently associated with malignant or metastatic disease and poor patient prognosis. FAK expression is increased in various tumors, such as those of the breast, colon, thyroid, head and neck, ovaries, liver, esophagus, and pancreas. The activated form of FAK constitutes tyrosine phosphorylation at the carboxyl-terminal ($Y^{397}$). This results in the phosphorylation of other tyrosine residues ($Y^{397}$, $Y^{407}$, $Y^{576}$, $Y^{577}$, $Y^{861}$, and $Y^{925}$), leading to the activation of several downstream signaling pathways, such as RAS/ERK, PI3K/AKT, and Crk/Dock180/Rac.

The data presented here suggest a novel pathway that could lead to the constitutive activation of FAK in pancreatic and possibly other aggressive cancer cells. TG2 was closely associated with FAK protein. The interaction of TG2 with FAK was associated with FAK autophosphorylation ($pY^{397}$) (FIG. 18). Indeed, ectopic expression of TG2 in BxPC-3 cells resulted in enhanced FAK activation (FIG. 18C) and FAK co-localization with TG2 in the focal points (FIG. 20D). Conversely, the inhibition of TG2 by siRNA inhibited FAK activation in Panc-28 cells (FIG. 19A). The major fraction of activated FAK was localized in the membrane in complex with TG2 (FIG. 20B). The ability of TG2 to associate with FAK, and FAK's subsequent phosphorylation, were independent of TG2 transamidation activity, as suggested by the observation that the expression of catalytically inactive point-mutated ($C_{277}S$) TG2 could result in a similar association and activation of FAK (FIG. 18A). Together, our results suggest a role for TG2 in FAK autophosphorylation that is mediated by a direct association between the two proteins. How the association of TG2 with FAK affects FAK's autophosphorylation remains a matter of speculation. Indeed, it is well known that the recruitment of FAK and its association with the cytoplasmic tails of integrins results in its autophosphorylation. Similarly, it is likely that the conformational changes induced in FAK in response to its interaction with TG2 can result in its autophosphorylation. Alternatively, the association of TG2 with pFAK might protect it from the action of endogenous phosphatases, such as PTEN.

Furthermore, TG2-mediated FAK activation was associated with the activation of PI3K/AKT pathway but had no effect on the RAS/MEK/ERK pathway (FIG. 18A). These observations are supported by an earlier report by Kang et al who showed that overexpression of TG2 in human chronic myelogenous leukemia (K562) cells was associated with activation of the PI3K/AKT signaling pathway. The significance of the PI3K/AKT pathway in conferring an aggressive phenotype to cancer cells has been well established (34-36). Indeed, our earlier studies with drug-resistant and metastatic breast cancer cells revealed that downregulation of TG2 expression renders the cells sensitive not only to anticancer drugs but also to stress-induced apoptosis. In the present study, the inhibition of endogenous TG2 by siRNA induced a massive accumulation of cytoplasmic vacuoles (FIG. 19B) that eventually led to the death of Panc-28 cells via autophagy (Ugur A et al., submitted).

Overall, the results of our study demonstrate that elevated expression of TG2 in PDAC tumor cells and cell lines contributes to increased cell survival and invasive functions. One mechanism that likely contributes to these effects is the ability of TG2 to associate with and activate FAK, resulting in the activation of its downstream pro-survival PI3K/AKT signaling pathway. In conclusion, our results suggest that TG2 could be an attractive target for anticancer therapeutics, and they provide a strong rationale for developing TG2 inhibitors to target the disruption of TG2-FAK protein-protein interactions.

Example 4

Overexpression of Tissue Transglutaminase Leads to Constitutive Activation of Nuclear Factor-κB in Cancer Cells: Delineation of a Novel Pathway Materials and Methods Cell Lines and Patient Samples.

High TG2-expressing (MDA-MB231/cl. 16) and low TG2-expressing (MDA-MB231/cl. 9) breast cancer sublines were established from the parental MDA-MB231 cell line as described previously. Drug-sensitive (MCF-7/WT) and drug-resistant (MCF-7/DOX) breast cancer cell lines were also established as described previously. Primary (WM35; radial growth phase) and metastatic (A375; vertical growth phase) melanoma cell lines were provided by Dr. Suhendan Ekmekcioglu (The University of Texas M. D. Anderson Cancer Center) and well-differentiated (BxPC3) and metastatic (Panc28) pancreatic adenocarcinoma cell lines were provided by Dr. Shrikanth A. Reddy (M. D. Anderson Cancer Center). All of the cell lines were maintained in the log phase of cell growth by culturing in RPMI 1640 or Dulbecco's modified Eagle's medium/F12 medium supplemented with fetal calf serum (10%, v/v), Normocin (0.1 mg/ml; Invivogen, San Diego, Calif.), L-glutamine (2 mM), and HEPES (10 mM; USB, Cleveland, Ohio) at 37° C. in a $CO_2$ incubator.

A tissue microarray consisting of 61 pancreatic ductal adenocarcinoma samples was constructed using formalin-fixed, paraffin-embedded archival tissue blocks as described previously. One-millimeter duplicate tissue cores were collected from the most representative areas of each tumor. The use of archival paraffin-embedded tissue blocks was approved by the institutional review board of the University of Texas M. D. Anderson Cancer Center.

Immunohistochemistry

The levels of TG2 and NF-κB expression in patient tumor samples were evaluated using an indirect immunoperoxidase procedure (ABC-Elite; Vector Laboratories, Burlingame, Calif.). In brief, antigen retrieval was performed by treatment of tissue sections in a steamer for 30 minutes. Antibodies against TG2 (CUB7401; Neomarkers, Fremont, Calif.) and the p65 subunit of NF-κB (Santa Cruz Biotechnology, Santa Cruz, Calif.) were used at 0.5 μg/ml and 10 μg/ml, respectively, at 4° C. for 16 hours. Secondary antibody incubation was performed at room temperature for 1 hour. Nuclear staining was performed using Mayer's hematoxylin as a counterstain. Immunohistochemical staining results were evaluated independently by laboratory personnel and a pathologist. TG2 expression was categorized as low (negative or weak cytoplasmic staining in tumor cells) or High (diffuse moderate to strong cytoplasmic staining in tumor cells). The staining results for the p65 subunit of NF-κB were categorized as negative (negative or strong cytoplasmic staining in <10% of the tumor cells) or positive (strong cytoplasmic staining in >10% of the tumor cells). Statistical analysis was performed using the Fisher exact test.

TG2 Enzymatic Activity

The level of TG2 enzymatic activity was determined using $Ca^{2+}$-dependent incorporation of [$^3$H] putrescine into dimethylcasein as described previously. The activity was expressed as nanomoles of putrescine incorporated per hour per milligram of total cell protein.

TG2 activity in intact cells was examined by preincubating cells (at 80% confluence) with 1 mM 5-(biotinamido) pentylamine (BPA; Pierce Biotechnology, Rockford, Ill.) overnight at 37° C. in RPMI 1640 medium containing 2% fetal calf serum. To induce activation of endogenous TG2, cells were treated with calcium ionophore A23187 (2 μM for 4 hours). After the incubation, cells were washed and lysed using sonication in 500 μl of Tris-HCl buffer (20 mM, pH 7.4 containing 1 mM EDTA, 150 mM NaCl, 14 mM 2-mercaptoethanol, and 1 mM phenylmethylsulfonyl fluoride). Equal amounts of cell lysates (30 μg protein) were fractionated using sodium dodecylsulfate (SDS)-polyacrylamide gel electrophoresis (PAGE) on an 8% gel and electrophoretically transferred onto a nitrocellulose membrane. The membrane was probed with horseradish peroxidase-conjugated streptavidin (Amersham, Piscataway, N.J.) and with an electrochemiluminescence reagent (Amersham).

Immunoblotting and Immunoprecipitation

Thirty micrograms of cell lysate protein were separated using SDS-PAGE on a 7.5% gel and electrophoretically transferred onto a nitrocellulose membrane. The membrane was probed with either an anti-TG2 (Neomarkers), anti-p65 (Santa Cruz Biotechnology), anti-IκBα (Santa Cruz Biotechnology), or anti-Bcl-XL (Santa Cruz Biotechnology) antibody. Antigen-antibody reactions were detected using an electrochemiluminescence detection system. All of the membranes were stripped and reprobed with an anti-β-actin antibody (Sigma-Aldrich) at a dilution of 1:4, 000 to ensure even loading of proteins in different lanes.

To immunoprecipitate the protein of interest, 500 μg of the cell lysate (in 50 mM Tris HCl, pH 8.0, 150 mM NaCl and 1% NP-40) was precleared by incubation with 50 μl of Trublot antimouse or antirabbit IgG-coated beads (eBiosciences, San Diego, Calif.). Five micrograms of the primary antibody was then added to the precleared cell lysate and incubated for 1 hour at 4° C. Immune complexes were recovered by incubation with the Trublot antimouse or antirabbit IgG-coated beads overnight at 4° C. At the end of the incubation period, the pellets were washed four times in ice-cold Tris-buffered saline (50 mM, pH 8.0) and resuspended in 50 μl of 1× loading buffer. The immunoprecipitates were analyzed using SDS-PAGE followed by immunoblotting and autoradiography.

NF-κB Activation

To assess NF-κB activation, electrophoretic mobility shift assay (EMSA) was performed as described previously. Briefly, nuclear extracts prepared from cells ($1\times10^6$/ml) were incubated with a $^{32}$P end-labeled 45-mer double-stranded NF-κB oligonucleotide (15 μg of protein with 16 fmol of DNA) from the human immunodeficiency virus long terminal repeat, 5'-TTGTTACAA GGGACTTTC CGCTG GGGACTTTC CAGGGAGGCGTGG-3' (boldface indicates NF-κB binding sites) (SEQ ID NO:17), for 30 minutes at 37° C., and the DNA-protein complex formed was separated from free oligonucleotide on 6.6% native polyacrylamide gels. A double-stranded mutated oligonucleotide, 5'-TTGTTACAA CTCACTTTC CGCTG CTCACTTTC CAGGGAGGCGTGG-3' (SEQ ID NO:18), was used to examine the specificity of binding of NF-κB to the DNA. The specificity of binding was also examined using competition with the unlabeled and mutated oligonucleotides. For supershift assays, nuclear extracts were incubated with antibodies against either the p50 or the p65 subunit of NF-κB for 30 minutes at 37° C. before the complex was analyzed using EMSA.

NF-κB-Dependent Reporter Gene Expression Assay

NF-κB dependent reporter gene transcription was analyzed using secretory alkaline phosphatase (SEAP) assay as described previously. Briefly, Panc28 and MCF-7 cells ($5\times10^5$ cells/well in a six-well plate) were transiently transfected by the calcium phosphate method in a 1 ml medium containing 0.5 μg of NF-κB promoter DNA, linked to the heat-stable SEAP gene or with the control plasmid pCMV-FLAG1 DNA. Transfected cells were either left untreated or treated with 1 μM A23187 (Sigma-Aldrich), 1 mM BPA, or 1 nM tumor necrosis factor (TNF)-α (Genentech, South San Francisco, Calif.). Twenty-four hours after treatment, the conditioned medium was removed and assayed for SEAP activity according to the manufacturer's instructions (Clontech Laboratories, Mountain View, Calif.) using an automated microplate reader (PerkinElmer, Wellesley, Mass.). In some experiments cells were co-transfected with dominant-negative construct of IκBα along with NF-κB reporter gene.

To inhibit endogenous TG2 expression we designed two siRNA duplexes to target the coding sequence of human TG2 mRNA and were synthesized by Qiagen Sciences (Germantown, Md.). The target sequence of TG2 siRNA1 is 5'-AAGGCCCGTTTTCCACTAAGA-3' (SEQ ID NO:19) and for siRNA2 is 5'-AAGGGCGAACCACCTGAACAA-3' (SEQ ID NO:20). Scrambled siRNA in which the sequence was scrambled but the nucleotide composition was the same as that in the siRNA1, was used in parallel as a control. For transfections, cells at 70% confluence in six-well plates were incubated with 5 μL volume of TG2-specific or scrambled (control) siRNA containing 30 μL RNAiFect reagent (Qiagen Sciences) in 2 ml of total volume made with serum-containing RPMI 1640 medium. After 48 hours of transfection, cells were washed and collected to measure NF-κB activation using EMSA or TG2 expression using immunoblotting and enzymatic activity.

Confocal Microscopy

To determine co-localization of TG2 and p65, Panc28 cells were grown on glass coverslips and fixed in 4% paraformaldehyde for 20 minutes at room temperature. Fixed cells were then incubated with the primary antibodies overnight, washed with PBS and incubated again with the secondary antibodies conjugated with either Alexa 546 (red) or Alexa 488 (green) (Molecular Probes, Eugene, Oreg.). The DNA dye Topro-3 (Molecular Probes) was used to co-stain the nuclei (blue). Cells treated with the secondary antibodies alone were used as controls. Confocal scanning analysis of the cells was performed with a Zeiss laser scanning confocal microscope or with an Olympus FluoView 300 confocal microscope in accordance with established method using sequential laser excitation to minimize the fluorescent emission bleed-through. Each section was examined for the presence of each stain at two excitations (546 nm and 488 or 633 nm as indicated in the text), and the data were compared pixel by pixel. Each image represented z-sections at the same cellular level and magnification; a three-dimensional reconstructed image was used to visualize the whole sample. Merging red and green showed co-localization of two proteins giving yellow color.

TG2 Adenovirus generation. An adenovirus containing a TG2 cDNA construct was provided by Dr. Ugra Singh (The Texas A&M University System Health Science Center College of Medicine, Temple, Tex.). Briefly, TG2 cDNA cloned into a pcDNA3.1 vector was first subcloned in a pshuttle 2 vector and then in a BD adenoX adenoviral vector (BD Biosciences, Palo Alto, Calif.). HEK293 cells were transfected with a recombinant adenoviral plasmid for packaging of adenoviral particles. The adenovirus was purified on a CsCl gradient and used at 25 multiplicity of infection (MOI). Cells infected with the lacZ adenovirus were used controls.

Statistical analysis. Unless otherwise stated, all experiments were conducted independently three times and the data reported are as a mean±SD or from a representative experiment. The paired t test was used for comparing samples of unequal variance and statistical significance was based on two-sided $P<0.05$.

Results

TG2 Expression Correlates with Constitutive NF-κB Activation

As the first step to determining the significance of increased TG2 expression in constitutive activation of NF-κB, we compared the TG2 expression and constitutive NF-κB activation in the cell lines MDA-MB231/cl. 9, MDA-MB231/cl. 16, MCF-7/WT, MCF-7/DOX, WM35, A375, BxPC3, and Panc28. Using EMSA, we observed high constitutive NF-κB activation in MDA-MB231/cl. 16, MCF-7/DOX, A375, and Panc28 cells (FIG. 1A). Western blot analysis revealed that the cell lines with high constitutive activation of NF-κB also had high basal levels of TG2 protein expression (FIG. 1B). The increased expression of TG2 in various cancer cell lines correlated well with a parallel increase in the enzymatic activity and activation of NF-κB (FIG. 1C). We observed a similar correlation between TG2 expression and constitutive NF-κB activation in several MiaPaca-2 pancreatic cancer cell line-derived sublines (data not shown). These results clearly suggested that there is a direct correlation between TG2 expression and NF-κB activation in various cancer cell lines.

FIG. 1D shows the specificity of an NF-κB band visualized using EMSA. Incubation of the nuclear extracts from Panc28 cells with antibodies against the p50 and p65 subunits of NF-κB prior to EMSA caused a shift in the band to a higher molecular weight. Similarly, the addition of an excess cold-unlabeled NF-κB oligonucleotide (100-fold) resulted in a complete disappearance of the band, whereas the addition of mutated NF-κB oligonucleotide did not affect the binding.

Activation and Over Expression of TG2 Results in Activation of NF-κB

Next we sought to determine the effect of the catalytic function of TG2 (protein cross-linking activity) on activation of NF-κB. For this purpose, we used calcium ionophore A23 187 to induce an increase in the level of free cytosolic $Ca^{2+}$, which is needed to activate the TG2 cross-linking functions. We treated low-TG2-expressing BxPc3 cells, high-TG2-expressing Panc28 cells, and TG2-negative MCF-7 cells with A23 187 (FIG. 2A) and monitored in situ activation of TG2 by determining the level of covalent conjugation of the substrate inhibitor BPA into cellular proteins. The results shown in FIG. 2B indicated a complete lack of BPA labeling in MCF-7 cells in the presence or absence of A23187. In BxPC3 cells, BPA labeling of cellular proteins became evident but only after treatment with A23 187. Panc28 cells, on the other hand, showed some basal TG2 activity (as evidenced by BPA labeling of the cellular proteins) that became more prominent in response to treatment with A23 187 (FIG. 2B).

We then examined the effect of A23187-induced TG2 activation on NF-κB activation. The results shown in FIG. 2C clearly demonstrated a strong correlation between in situ TG2 activity and NF-κB activation. Treatment of BxPc3 cells with A23187 resulted in strong activation of NF-κB that reached the level of untreated Panc28 cells (FIG. 2C). In Panc28 cells that showed some basal TG2 activity (FIG. 2B) and high constitutive NF-κB activation (FIG. 2C) both could be further induced by treatment with A23187. On the other hand, MCF-7 cells that lacked basal TG2 expression and activation in response to treatment with A23187 failed to show an increase in NF-κB activation even after treatment with A23187. Time-course and dose-response studies using BxPC3 cells revealed that treatment with 1 μM A23187 for 24 hours is optimal for NF-κB activation (data not shown). Next, we sought to determine the effect of increased TG2 expression on NF-κB activation by reconstituting TG2 levels in low-TG2-expressing BxPC3 cells. We tested cells infected with an adenoviral construct containing a full-length TG2 cDNA or empty vector alone for TG2 levels and NF-κB activation (FIG. 2D). Indeed, increased TG2 protein expression in BxPC3 cells was associated with increased constitutive NF-κB activation. Vector-alone-infected cells showed no increase in TG2 protein expression or NF-κB activation. These results suggested that increased expression of TG2 and its transamidation activity were essential for NF-κB activation.

Inhibition of TG2 Activity Inhibits Activation of NF-κB

Because the activation of TG2 by treatment with A23187 induced activation of NF-κB, in another experiment, we sought to determine the effect of two TG2-specific inhibitors, monodansylcadaverine (MDC) and BPA, on NF-κB activation. Panc28 cells treated with BPA showed about 70% inhibition of constitutive activation of NF-κB (FIG. 3A). Moreover, preincubation of Panc28 cells with BPA failed to further augment A23187-induced activation of NF-κB. Similarly, treatment of Panc28 cells with MDC (50 μM, 24 hours) resulted in about 60% inhibition of NF-κB activation and blocked A23187-induced activation (FIG. 3A, lanes 5 and 6).

Using EMSA, we demonstrated that BPA and MDC could effectively block DNA binding of NF-κB protein to its consensus sequence. However, DNA binding alone does not always co-relate with NF-κB—dependent gene transcription, suggesting a role for an additional regulatory step. To determine the effect of BPA on NF-κB-dependent target gene expression, we transiently transfected Panc28 and MCF-7 cells with the NF-κB SEAP reporter construct. The results shown in FIG. 3B demonstrated that transient transfection of the SEAP reporter in MCF-7/WT cells resulted in its expression (14-fold) only in response to treatment with TNF-α that could be effectively inhibited by dominant-negative (DN) IκBα but not by BPA. No basal or A23187-induced activity of SEAP in the NF-κB SEAP reporter was seen in MCF-7/WT cells. In contrast, untreated Panc28 cells showed a substantial increase (13-fold) in SEAP expression that was significantly inhibited ($P<0.002$) by BPA. SEAP expression did not increase further in response to treatment with A23187 (1 mM for 24 hours) and was not inhibited by dominant-negative IκBα. These results suggested that TG2-mediated activation of NF-κB is mediated via some novel pathway that is independent of IKK.

For a more specific approach to determine the significance of TG2 expression in constitutive activation NF-κB, we investigated the effect of TG2 siRNA on the expression of NF-κB target gene, Bcl-XL. Using Western blot analysis, we found that siRNA transfection (siRNA1 and siRNA2) of Panc28 cells resulted in 70-80% inhibition of TG2 activity (data not shown) and protein expression (FIG. 3C). Reprobing of membrane with an anti-Bcl-XL antibody revealed that siRNA blocked Bcl-XL protein expression. Mobility shift assay showed that constitutive activation of NF-κB could be effectively blocked by knocking down TG2 expression. The siRNA-mediated downregulation of NF-κB could not be reversed by treatment with A23187. These results demonstrated that NF-κB activation in Panc28 cells is dependent on TG2 expression.

TG2 is associated with NF-κB in Panc28 cells. Immunoprecipitation of Panc28 cytoplasmic extracts with anti-IκBα antibody effectively pulled down the TG2 protein in addition to the IκBα and p65 proteins, suggesting that TG2 forms a part of the complex between p65/p50 and IκBα (FIG. 4A). We confirmed this association by immunoprecipitating TG2 and demonstrating the presence of p65 and IκBα in the immune complex (data not shown). Furthermore, confocal microscopy data supported the co-localization of TG2 with p65 in the cytoplasm (FIG. 4B). The association between TG2 and p65 further increased in response to treatment with A23187, which led to increased translocation of the p65/TG2 complex in the nucleus (FIG. 4B, inset). These results clearly suggested that TG2 is closely associated with the IκBα/p65: p50 complex in the cytoplasm and translocates to the nucleus in a complex with p65/p50.

Mechanism of TG2-Mediated NF-κB Activation

To delineate the possible mechanism by which TG2 mediates NF-κB activation, we studied the effect of TG2 on IκBα. Immunoprecipitation of a cytoplasmic extract from TG2-rich Panc28 cells with an anti-IκBα antibody revealed the presence of a 66-dimeric IκBα band (FIG. 4C, left panel) in addition to the 33-kDa monomeric IκBα band. Treatment of cells with A23187 further augmented the formation of dimeric bands and resulted in the appearance of another polymeric IκBα band. We also observed these polymeric forms of IκBα in in vitro labeling of IκBα with BPA. We labeled the IκBα immunoprecipitates from Panc28 cytoplasmic extracts with BPA in vitro in the presence of $Ca^{2+}$ (3 mM) and probed them with horseradish peroxidase-conjugated streptavidin in a Western-blot-type assay. The results shown in FIG. 4C (right panel) demonstrated the presence of high-molecular-weight forms (dimeric and polymeric) of IκBα, confirming that TG2 is closely associated with IκBα and that IκBα (can serve as a substrate for TG2-catalyzed cross-linking reactions.

TG2 Expression Correlates with NF-κB Activation in Pancreatic Tumors

To further confirm the significance of our in vitro observations that expression of TG2 results in constitutive activation of NF-κB, we constructed a human tissue microarray containing 61 pancreatic ductal carcinoma samples using formalin-fixed, paraffin-embedded archival tissue blocks. We evaluated the expression of TG2 and NF-κB using immunohistochemistry under identical standardized conditions for all of the samples with consecutive tissue sections cut from the array block. Examples of both positive and negative staining are shown in FIG. 5A. Quantification of the staining showed that in the 34 pancreatic carcinoma samples with high levels of TG2 expression, 29 (85%) also showed activation/overexpression of NF-κB. In contrast, of the 27 pancreatic carcinoma samples with low levels of TG2 expression, 13 (48%) did not show activation/overexpression of NF-κB (FIG. 5B). Strong TG2 immunopositivity was associated with activation/overexpression of NF-κB ($P=0.0098$; Fisher exact test). These data further supported the notion that expression of TG2 contributes to constitutive activation of NF-κB in pancreatic cancer.

Discussion

Our results demonstrate that a great majority of pancreatic cancer cells and cell lines have high levels of expression of the multifunctional protein TG2. Our data provide the first evidence that TG2 forms a ternary complex with NF-κB/IκBα. By catalyzing posttranslational modification (cross-linking) of IκBα, TG2 results in constitutive activation of NF-κB. The activation of TG2 by calcium ionophore A23187 and overexpression of TG2 in the low-TG2-expressing BxPc3 cells strongly induced activation of NF-κB. Moreover, treatment with the TG2-specific inhibitors BPA and MDC caused strong inhibition of NF-κB activation, an observation that was further supported by the use of TG2-specific siRNA. Overall, these results suggest a strong rationale for inhibiting endogenous TG2 activity to inhibit constitutive NF-κB activation, which can improve the sensitivity of cancer cells to anticancer therapies.

We and others previously showed that, irrespective of their source or type, cancer cells selected for resistance to chemotherapeutic drugs exhibit high levels of TG2 expression. Notably, downregulation of TG2 by stable transfection with TG2-specific antisense-RNA or with siRNA rendered the cells sensitive to chemotherapeutic drugs, suggesting that TG2 plays a role in acquisition of drug resistance. Similarly, metastatic cancer cells and cell lines have high levels of TG2 expression. Indeed, TG2 was one of the 11 proteins whose expression was selectively increased in metastatic lung cancer cells as determined using proteomic analysis. Similarly, several metastatic breast cancer cell lines have exhibited increased levels of TG2 protein expression. Importantly, lymph node metastases obtained from patients with breast cancer showed significantly higher TG2 expression than did primary tumors obtained from the same patients. These observations suggest that the development of drug resistance and metastatic phenotypes in cancer cells is associated with increased expression of TG2. However, a direct link between TG2 expression, drug resistance, and metastasis has not been established.

The data presented here suggest that TG2 expression contributes to the development of drug resistance and metastatic phenotypes by inducing constitutive activation of NF-κB. Many cancer cells and cell lines have constitutive NF-κB activation, which enables malignant cells to escape apoptosis. In contrast, activation of NF-κB in normal cells is transient, which prevents abnormal cell growth and survival. Therefore, constitutively activated NF-κB in cancer cells may play a role in the development of drug resistance by attenuating the cells' apoptotic response to genotoxic anticancer drugs and ionizing radiation. Indeed, the expression of several genes that encode antiapoptotic proteins that either act at the mitochondrial level, such as Bcl-XL and BFL1, or directly block caspase activation, such as inhibitor of apoptosis protein 1, inhibitor of apoptosis protein 2, and X-linked inhibitor of apoptosis protein, can be directly regulated by NF-κB. In particular, the failure of a human lung carcinoma cell line to respond to chemotherapeutic drugs has been attributed to NF-κB-induced expression of Bcl-XL and BFL1.

Similarly, increased expression of TG2 may also contribute to the development of metastatic phenotypes by constitutively activating NF-κB. The metastatic process requires the migration of cancer cells into and out of the walls of blood vessels. Several adhesion molecules, such as ICAM-1, VCAM-1, and ELAM-1, whose expression is under the direct control of NF-κB, play a critical role in this process. Moreover, inducible nitric oxide synthase, the expression of which is linked to the metastatic ability of cancer cells, can also be regulated by NF-κB. In breast cancer cells, NF-κB has been shown to facilitate the cell motility by upregulating the expression of the chemokine receptor CXCR. Conversely, another study found that inhibition of NF-κB activity by expression of a mutant IκBα inhibited liver metastasis. All of these observations support the involvement of NF-κB in the development of metastatic phenotypes in cancer cells. In view of these observations, researchers have developed or are developing numerous NF-κB inhibitors that target the upstream kinase IKK, but none of these molecules have proven to be specific for IKK or effective in inhibiting constitutively activated NF-κB.

Based on our earlier observations that chemoresistant and metastatic cancer cells have high levels of TG2 expression and our present observation that TG2 overexpression results in constitutive NF-κB activation, we infer that TG2 expression plays a role in conferring drug-resistant and metastatic phenotypes to cancer cells. FIG. 27 summarizes the possible pathways that lead to constitutive activation of NF-κB by TG2. We speculate that TG2 catalyzes cross-linking of IκBα and destabilizes the IκBα/NF-κB complex, resulting in the release and activation of NF-κB. Indeed, previous observations by Lee et al. demonstrated that TG2 could effectively cross-link IκBα and induce its polymerization in vitro. Importantly, the polymerized form of IκBα was unable to bind to p65:p50 in their study. Alternatively, association of TG2 with p50/p65 may interfere with the binding of IκBα to NF-κB complex resulting in its constitutive activation.

The data reported here also demonstrate for the first time that TG2 is closely associated with the IκBα/p65:p50 complex in the cytoplasm. The significance of this association is not clear at this time, but we are currently investigating it in our laboratory. We speculate that TG2 plays a role in destabilizing the IκBα/p65:p50 complex and thus in regulating NF-κB activation. We also observed nuclear localization of TG2 in association with p65 (unpublished data). The nuclear association of TG2 with p65 is also evident according to confocal microscopy data in A23187 treated cells (FIG. 25B). Recent reports suggest that under certain conditions, TG2 can serve as a kinase, and its serine-threonine kinase activity can phosphorylate histones and p53. Because p65 undergoes phosphorylation by various kinases at serine536, we are also investigating the possibility that p65 serves as substrate for TG2 kinase activity.

In summary, our study provides the first evidence that expression of TG2 results in constitutive activation of NF-κB in an IKK-independent manner. We expect that inhibitors designed to target TG2 can inhibit NF-κB activity and may improve the response of cancer cells to anticancer treatment.

Example 5

Inhibition of Tissue Transglutaminase Promotes Gemcitabine Efficacy and Blocks Pancreatic Cancer Growth and Metastasis in Mice Materials and Methods Materials Rabbit polyclonal antibodies against phosphorylated Akt (pAkt; Ser[473]) were obtained from Cell Signaling Technology (Beverly, Mass.). The anti-TG2 monoclonal antibody CUB7401 was purchased from Neomarkers (Fremont, Calif.). A monoclonal antibody against VEGF was obtained from Santa Cruz Biotechnology (Santa Cruz, Calif.). An anti-□-actin antibody was purchased from Sigma Chemical Co. (St. Louis, Mo.), and horseradish peroxidase-conjugated goat anti-rabbit and sheep anti-mouse antibodies were purchased from Amersham Biosciences (Piscataway, N.J.). DMEM/F12, fetal bovine serum, and the antibiotic (Normocin) were purchased from Invivogen (San Diego, Calif.). The liquid DAB+ Substrate Chromogen System-horseradish peroxidase used for immunohistochemistry was obtained from DakoCytomation (Carpinteria, Calif.). Gemzar, which was supplied by Eli Lilly and Company (Indianapolis, Ind.), was stored at 4° C. and dissolved in sterile phosphate-buffered saline (PBS) on the day of use. D-luciferin potassium salt (Xenogen Corp., Hopkinton, Mass.) was dissolved in sterile PBS at a concentration of 40 mg/ml.

Cell Lines.

The Panc-28 cell line was kindly provided by Dr. Shrikanth Reddy (The University of Texas M. D. Anderson Cancer Center, Houston, Tex.). The cells were cultured in DMEM/F12 medium supplemented with fetal calf serum (10%, v/v), Normocin (0.1 mg/mL), L-glutamine (2 mM), and HEPES (10 mM; USB, Cleveland, Ohio) at 37° C. in a $CO_2$ incubator.

TG2 siRNA.

TG2 siRNA sequences were designed and purchased from Qiagen (Germantown, Md.). The control sequence that was not homologous to any human mRNA (as determined by using BLAST search [National Center for Biotechnology Information, Bethesda, Md.]) was used as a control, and the sequence designed to target TG2 mRNA (target sequence, 5'-AAGGGCGAACCACCTGAACAA-3' (SEQ ID NO:20))

was used for downregulation of endogenous TG2 expression by transfection of Panc-28 cells, as described previously (21).

Liposomal-TG2 siRNA.

siRNA used for in vivo delivery was incorporated into neutral liposomes composed of 1,2-dioleoyl-sn-glycero-3-phosphatidylcholine (DOPC). siRNA and DOPC were mixed in the presence of excess t-butanol at a ratio of 1:10 (w/w) as described previously (22). Tween 20 was added to the mixture, which was then vortexed, frozen in an acetone/dry ice bath, and lyophilized. Before administration into mice, the preliposomal formulation powder (lyophilizate) containing the lipid and siRNA was hydrated with normal saline at a concentration of 15 μg/mL. Once reconstituted, the DOPC-siRNA preparation was used within 12 hours.

PDAC orthotopic tumor model.

Male athymic nu/nu mice (4 weeks old) were obtained from the breeding colony of the Department of Experimental Radiation Oncology at M. D. Anderson Cancer Center. The animals were housed four per cage in standard acrylic glass cages in a room maintained at constant temperature and humidity with a 12-h light and darkness cycle and fed a regular autoclaved chow diet with water ad lithium. Before initiating the experiment, animals were acclimatized to a pulverized diet for 3 days. All studies were conducted according to an experimental protocol reviewed and approved by the M. D. Anderson Institutional Animal Care and Use Committee.

Panc-28 cells were stably transduced with the firefly luciferase gene as described previously (23). Luciferase-infected Panc-28 cells were harvested from subconfluent cultures after brief exposure to 0.25% trypsin and 0.2% EDTA. Trypsinization was stopped with the medium containing 10% fetal bovine serum. The cells were washed once in serum-free medium and resuspended in PBS. Single cell suspensions with >90% cell viability were used for implantation into the mice. Animals were anesthetized using intraperitoneal injection of 200 μl ketamine (100 mg/kg) and xylazine (5-10 mg/kg). For orthotopic implantation of tumor cells into the mice, a small incision (2 cm long) was made on the left flank, the pancreas was gently pulled out using blunt forceps, and a 100 μl suspension of luciferase-infected Panc-28 cells ($1\times10^6$) was injected directly into the pancreas using a 27-gauge needle (1-ml disposable tuberculin syringe). The incision was closed in a single layer using sterile surgical Autoclips (Braintree Scientific, Braintree, Mass.), antibacterial mycotic cream was applied to the wound and the animal was placed on a heating pad to maintain body temperature and closely monitored until conscious.

Luminescence Imaging.

Tumor growth in the mice after tumor-cell implantation was monitored weekly using a noninvasive bioimaging technique. Prior to imaging, animals were anesthetized using 1.5% isoflurane/air inhalation and injected intraperitoneally with D-luciferin potassium salt (Xenogen Corp.) in PBS (150 mg/kg). Ten minutes after injection, each mouse was placed in the right lateral decubitus position, and bioluminescence was measured using a cryogenically cooled IVIS imaging system coupled with a data acquisition computer running LivingImage software (Xenogen Corp., Alameda, Calif.). A digital grayscale image of each animal was acquired followed by acquisition and overlay of a pseudocolor image of the spatial distribution of photons emerging from active luciferase within the tumor. The signal intensity was quantified as the sum of all detected photons within the region of interest per second per $cm^2$ per steridian.

Prior to evaluation of the therapeutic efficacy of TG2 siRNA, the ability of liposomal-encapsulated siRNA (Alexa [fluor]-546-labeled) to downregulate TG2 expression in Panc-28 tumors was examined by administering the liposomal formulation in the tail vein or intraperitoneally in five mice each (150 μg/kg/dose/route, three doses total, each 3 days apart). Based on the extent of downregulation of TG2 expression in the two groups, the tail vein route was apparently superior to the intraperitoneal route for the delivery of TG2 siRNA.

Therapeutic Efficacy of Liposomal TG2 siRNA.

Panc-28 cells ($1\times10^6$) were implanted orthotopically in the pancreases of nude (nu/nu) mice. The resulting tumor growth was monitored weekly for 3 weeks using the bioluminescence IVIS Imaging System 200 (Xenogen Corp.). After the 3-week monitoring period, mice were randomly distributed into four treatment groups (five mice/group): group I received control liposomal siRNA (scrambled; 150 μg/kg), three times weekly by intravenous injection; group II received gemcitabine alone (25 mg/kg) twice weekly by intraperitoneal injection, group III received liposomal TG2 siRNA alone (150 μg/kg) three times weekly by intravenous injection, and group IV received both gemcitabine (25 mg/kg) twice weekly by intraperitoneal injection and liposomal TG2 siRNA (150 μg/kg) three times weekly by intravenous injection.

Mice were imaged for tumor growth on days 0, 2, 9, 16, and 23 during the treatment. After delivery of a total of 10 doses and 3 days after delivery of the last dose, all of the animals were killed. Their primary pancreatic tumors were excised, and the final tumor volumes were measured using a digital clipper and calculated using the formula $V=\frac{2}{3}\pi r^3 r$ in which r is the mean radius in three different dimensions (length, width, and depth). One third of the tumor tissue was formalin-fixed and paraffin-embedded for immunohistochemistry and routine hematoxylin and eosin staining. The other one third of the tumor tissue was fixed in OCT for fluorescence and tunnel assay and the remaining tumor tissue was snap-frozen and stored at −80° C. until use.

Western Blot Analysis.

Pancreatic tumor tissue samples obtained from control and experimental mice were minced and incubated on ice for 30 min in 0.5 ml of ice-cold lysate buffer (20 mmol/L Tris-HCl, pH 7.4, containing 10% NP-40, 5 mol/L NaCl, 1 mol/L HEPES, 0.5 mol/L EDTA, 0.1 mol/L phenylmethylsulfonyl fluoride, 0.2 mol/L sodium orthovanadate, 1 mol/L NaF, 2 μg/ml aprotinin, and 2 μg/ml leupeptin). The minced tissue was homogenized using a Dounce homogenizer and centrifuged at 16,000×g at 4° C. for 10 min. Fifty micrograms of total protein from each sample was then fractionated using sodium dodecyl sulfate-polyacrylamide gel, electrotransferred onto nitrocellulose membranes, blotted with appropriate antibodies, and antigen antibody reaction detected using enhanced chemiluminescence (Amersham Pharmacia Biotech, Piscataway, N.J.). Some of the membranes were stripped using Restore stripping buffer (Pierce, Rockford, Ill.) and reprobed with another antibody. The protein bands obtained were quantified using the AlphaEase FC (Fluor Chem 8900) software program (Alpha Innotech, San Leandro, Calif.).

Immunohistochemistry.

Tissue microarray slides constructed using 65 formalin-fixed patient tumor samples and 9 normal pancreatic tissue samples were used for this study. Samples were obtained from patients with primary PDAC who underwent initial pancreaticoduodenectomy without prior chemotherapy or radiation therapy. TG2 protein expression in these tumor samples and xenograft tumors from siRNA treated mice was evaluated immunohistochemically using the Vectastatin Elite ABC immunostaining kit (Vector Laboratories, Burlingame, Calif.) as described previously (12). In brief, antigen retrieval was performed by treating tissue samples in a steamer for 30 min. Mouse anti-TG2, rabbit anti-pAKT$^{ser473}$ (Cell Signaling Technology), rabbit anti-Ki-67 (clone SP6; NeoMarkers) or mouse anti-CD31 (Pharmingen, San Diego, Calif.) antibodies overlaying the tissue sections were incubated at 4° C. for 16 h. Secondary antibody incubation was performed at ambient temperature for 1 h. Mayer's hematoxylin nuclear stain was used as a counter stain. Immunostaining results were evaluated and scored independently by a pathologist and the laboratory personnel in a double-blinded manner. TG2 expression in tumor cells was categorized as negative (weak or negative cytoplasmic staining) or positive (diffuse moderate to strong cytoplasmic staining). pAKT$^{ser473}$ expression in tumor cells was categorized as negative (no or very weak cytoplasmic staining) or positive (diffuse moderate or strong cytoplasmic staining).

Proliferation.

Ki-67 staining was used to evaluate the proliferation index of in vivo growing xenografts and expressed as the number of Ki-67$^+$ cells±standard error (SE) as determined by counting 10 random microscopic fields for three different tumor samples per treatment group.

Microvessel Density.

A rat anti-mouse CD31 monoclonal antibody was used to determine the microvessel density in xenografts. The CD31 stained slides were observed under a Leica DM4000B fluorescence microscope (Leica Microsystems Inc, Bannockburn, Ill.) equipped with SPOT-RTKE digital camera (Diagnostic instruments, Sterling Heights, Mich.) and the images were acquired and stored using SPOT advanced software (Diagnostic instruments, Sterling Heights, Mich.). The stored images were processed using NIH ImageJ software. The vessel density in each image was estimated by setting a minimum threshold of 4 pixel$^2$. Setting a minimum threshold enables to avoid the background non-specific staining and to eliminate the fluorescence signal from single endothelial cell. Results were expressed as the mean number of vessels±SE per high power field (HPF, 100× magnification). A total of 20 random HPFs were examined and counted in four different tumor samples from each treatment group.

TUNNEL Assay.

Terminal deoxynucleotidyl transferase mediated αUTP-biotin nick end labeling (TUNNEL) assay (Roche Molecular Biochemicals, Mannhein, Germany) of frozen sections to detect apoptotic cells was performed according to the manufacturer's protocol. The apoptotic fluorescence-positive cells were counted under a microscope and expressed as the percentage of total cells±SE. Ten fields in three tumors per treatment group were examined.

Electrophoretic Mobility Shift Assay.

To determine the level of NF-□B activation in xenografts, electrophoretic mobility shift assay was used as described previously (21). Briefly, nuclear extracts from tumor homogenates were incubated with a $^{32}$P-end-labeled 45-mer double-stranded NF-κB oligonucleotide (15 μg protein with 16 fmol DNA) for 30 min at 37° C., and the DNA-protein complex that formed was separated from free-oligonucleotide on 6.6% native polyacrylamide gels. The dried gels were autoradiographed, and radioactive bands were quantitated using a STORM 220 PhosphorImager (Amersham Biosciences) with the ImageQuant software program (Molecular Dynamics, Sunnyvale, Calif.) software.

Statistical Analysis.

We used standard deviation of 100 and mean difference between control and modified/treated groups as 200 for tumor volume to do the power calculation for in vivo studies based on the two-sided two-sample Student's t-test (nQuery 5.0). Using $p<0.05$, we observed that n=5 mice per group is adequate to achieve a power (1-β) of 80%. For tumor volume calculation, values were initially subjected to one-way ANOVA and then compared amongst groups using unpaired Student's t-test. For TG2 expression in patient samples, values were calculated using Fisher's exact test with $p<0.001$ set as statistically significant. For Ki-67 staining, microvessel density, and in situ TUNNEL assay, values were initially subjected to one-way ANOVA and then compared amongst groups using unpaired Student's t-test.

Results

TG2 Expression in PDAC Tumors.

We previously observed that TG2 protein is aberrantly expressed in a large number of PDAC tumors and cell lines (19). In the present study, we examined the expression of TG2 in a human tissue microarray containing 65 PDAC tumor samples and 9 normal pancreatic tissue samples. We found high basal levels of TG2 expression in 51 of the 65 (78%) tumor samples studied (FIG. 28). However, only one of the nine (11%) normal pancreatic tissue samples showed cytoplasmic staining for TG2. Also, few endothelial cells in the normal pancreatic tissue samples stained positive for TG2. TG2 expression was significantly higher in PDAC tumor samples than in normal ducts ($P<0.0001$). We observed no staining in sections treated with control isotypic IgG instead of an anti-TG2 antibody. Although, the sample size was too small to comment on the correlation between TG2 expression and histological grades (I-III), node status (N stage), and metastasis (M stage), we observed a trend toward an increasing TG2 expression as the tumor stage increased (T1, 3/5 [60%]; T2, 32/44 [73%]; T3, 13/16 [81%]).

We also previously reported that TG2 expression confers resistance to gemcitabine and promotes invasiveness in PDAC cells. Therefore, in the present study, we chose to evaluate the potential of TG2 as a therapeutic target for chemoresistant and metastatic PDAC. For this purpose, we used highly TG2-expressing, invasive, gemcitabine-resistant Panc-28 cells. We stably infected cells with luciferase as described previously and injected them into the pancreases of nude mice to establish orthotopic pancreatic tumors as described in Materials and Methods. Resulting Panc-28 tumors in the mice were highly aggressive and advanced rapidly to locally disseminated disease over about 6 weeks after tumor-cell implantation.

Downregulation of TG2 Expression by siRNA.

Ample evidence supports that downregulation of TG2 expression by siRNA, antisense or ribozyme results in inhibition of FAK/AKT and NF-κB pathway activation, reversal of drug-resistance, and inhibition of the invasive phenotype in a wide variety of cell types. Notably, inhibition of TG2 expression in pancreatic cancer cells has resulted in arrest of cell growth and onset of autophagic cell death. To further validate these in vitro findings, we studied the impact of downregulation of TG2 expression on PDAC growth, metastasis, and gemcitabine sensitivity. We employed orthotopically implanted PDAC tumors in nude mice as a model for treatment of pancreatic cancer using DOPC liposomes as the mode of delivery of TG2 siRNA. In a preliminary experiment, we first determined the optimal route for delivery of DOPC-encapsulated TG2 siRNA to downregulate TG2 expression in tumors. Five weeks after tumor-cell implantation, we gave groups of mice fluorescent-tagged TG2 siRNA in DOPC liposomes (150 μg/kg) either intraperitoneally or intravenously via the tail vein. All of the animals received a total of three doses each every other day for 6 days. Three days after the last TG2 siRNA injection, we killed the mice and harvested their tumors for further analysis.

Immunohistochemical and Western blot analysis consistently revealed >80% reduction in TG2 expression in the tumors obtained from mice that received TG2 siRNA intravenously. The reduction in TG2 expression was also evident in tumors obtained from mice that received TG2 siRNA intraperitoneally, but the degree of inhibition from mouse to mouse was less consistent than that in intravenous group. Furthermore, fluorescence microscopy revealed a significant uptake of fluorescent-labeled TG2 siRNA in tumors treated intravenously. Based on these results, we used the intravenous route for administration of siRNA-DOPC three times a week in subsequent therapeutic experiments.

TG2 siRNA-DOPC as Therapy for PDAC.

We implanted luciferase-transduced Panc-28 cells in the pancreases of mice as described in Materials and Methods. Starting on the day of implantation, we imaged mice weekly to measure tumor growth and randomly distributed the mice into four groups (n=5 mice per group) at the end of the third week. We administered treatment with TG2 siRNA to the mice as described in Materials and Methods to determine its therapeutic potential. We gave a total of 10 siRNA-DOPC doses (intravenously) and 7 gemcitabine doses (intraperitoneally). Three days after the last treatment, we killed the mice and examined them carefully for tumor size, metastasis, and other gross pathological changes. Luciferase bioluminescence data derived from IVIS images obtained weekly revealed that the tumor growth in mice given TG2 siRNA-DOPC in combination with gemcitabine was significantly retarded (p=0.019) when compared with that in the mice given control siRNA-DOPC (FIG. 29). Treatment with either TG2 siRNA-DOPC or gemcitabine alone resulted in about 50% reduction in the final tumor volumes (FIG. 29). The mice tolerated the treatments well and there were no visible signs of toxicity including change in the body weight or feeding habits. Thus, the combination of TG2 siRNA-DOPC and gemcitabine had a much superior response than did TG2 siRNA-DOPC or gemcitabine alone.

The Panc-28-induced tumors rapidly progressed into locally advanced disease in nude mice. Therefore, we also examined the effect of various treatments on the number of metastatic foci in organs adjacent to pancreas, such as the spleen, mesentery/momentum and liver in these mice. We scored metastasis as described in Materials and Methods. The results shown in FIG. 30 clearly demonstrate that treatment with TG2 siRNA-DOPC alone was highly effective in inhibiting the progression of PDAC tumors to metastatic disease. Interestingly, treatment with gemcitabine alone, which caused noticeable reduction in tumor growth was completely ineffective in inhibiting metastasis. Mice given TG2 siRNA-DOPC in combination with gemcitabine also had significant decreases in their metastasis scores similar to those in mice given TG2 siRNA-DOPC (FIG. 30). These results suggested that treatment with gemcitabine alone, although capable of inhibiting the growth of or inducing cell death in some Panc-28 clones, does not affect the survival or growth of metastatic clones.

Effect of Targeting TG2 on Survival Pathways.

Based on our previous observations that TG2 expression results in constitutive activation of the FAK/Akt and NF-κB survival pathways, we examined the in vivo effect of treatment with TG2 siRNA-DOPC on these pathways. As shown in FIG. 4, TG2 siRNA-DOPC induced downregulation of TG2 expression in xenograft tumors was associated with inhibition of NF-κB activity and expression of its downstream target gene, VEGF. Moreover, tumors obtained from TG2 siRNA-DOPC-treated mice showed inhibition of pAkt (serine 473) (FIG. 32). Tumors obtained from mice that received gemcitabine or control siRNA-DOPC alone showed no significant changes in NF-κB activity or pAkt levels.

Effect of TG2 Inhibition on Cell Proliferation, Angiogenesis and Apoptosis.

To further delineate the mechanisms that underlie the antitumor effect of TG2 siRNA-DOPC, we examined several biological end-points, including cell proliferation, angiogenesis, and apoptosis, in tumors from all treatment groups. We used Ki-67 staining to analyze cell proliferation. More than 90% reduction in Ki-67 expression was evident ($p<0.001$) in tumors obtained from mice given TG2 siRNA-DOPC alone or in combination with gemcitabine (FIG. 32). Tumors obtained from mice given gemcitabine alone or control (scrambled) siRNA-DOPC consistently showed high levels of Ki-67 staining (FIG. 32).

Next, we evaluated the blood vessel density in tumors obtained from mice in the different treatment groups. The representative images shown in FIG. 32 reveal a significant decrease in the mean blood vessel density in tumors obtained from mice that received TG2 siRNA-DOPC or gemcitabine alone. Densitometric analysis showed a significant difference in the mean microvascular density ($P<0.0013$) in the mice that received TG2 siRNA-DOPC plus gemcitabine as compared to the mice that received control siRNA-DOPC. Taken together, these results suggested that downregulation of TG2 expression in combination with gemcitabine can result in decreased VEGF expression and decreased mean blood vessel density. Thus, treatment with TG2 siRNA-DOPC plus gemcitabine can affect the neovascularization process in a paracrine manner by affecting VEGF levels rather than due to downregulation of TG2 in endothelial cells.

Finally, we evaluated apoptosis in orthotopic tumors using TUNNEL assay. PDAC tumors treated with gemcitabine either alone or in combination with TG2 siRNA-DOPC treated tumors showed significant increases in the numbers of apoptotic cells. No differences in the apoptotic index in TG2 siRNA-DOPC-treated tumors were evident, and the extent of apoptosis in this group was similar to that in the control siRNA-DOPC group. These results agree with our previous in vitro data suggesting that aberrant expression of TG2 in PDAC cells contributes to their aggressive behavior by constitutively activating cell survival signaling pathways and that downregulation of TG2 expression results in autophagic rather than apoptotic cell death in PDAC cells.

Discussion

In the present study, we examined the potential of TG2 as a therapeutic target for treating PDAC in an orthotopic nude mouse model. Using DOPC liposomes as the mode of delivery, we showed that TG2 siRNA could effectively downregulate TG2 expression in tumors and inhibit their growth and metastatic spread. Previous studies convincingly documented the association of increased TG2 expression, drug resistance, and metastatic phenotypes in various cancer types. In addition, the majority of PDAC tumors and cell lines have increased basal levels of TG2 expression (FIG. 28). As a matter of fact, a comprehensive analysis of 33,000 genes using three different methods identified TG2 as one of the most differentially expressed genes in PDAC tumors. Similarly, in an attempt to identify metastasis-associated proteins using proteomic analysis, Jiang et al. identified TG2 as one of 11 proteins selectively amplified in metastatic human lung carcinoma. Based on these observations, we reasoned that elevated expression of TG2 in pancreatic cancer cells could serve as a novel target in treating PDAC tumors, which are intrinsically resistant to chemotherapeutic drugs and highly metastatic. The data presented here clearly demonstrate the usefulness of downregulating TG2 expression in inhibiting PDAC tumor growth and mitigating metastatic spread of the disease. Notably, downregulation of TG2 expression by siRNA-DOPC rendered PDAC cells sensitive to gemcitabine, the drug most commonly used to treat this tumor, both alone and in combination with other therapeutic modalities, although it did not have much of an impact on survival.

Several recent reports have documented a role for TG2 in promoting the migration and invasion of normal and cancerous cells. For example, researchers have implicated that TG2 has a role in transmigration of T lymphocytes, migration of retinal pigment epithelial, monocytic, and neuroblastoma cells, and invasion of breast and pancreatic cancer cells. Under physiological conditions, induction of TG2 expression in normal cells is transient and tightly regulated by certain hormones and growth factors. In contrast, many types of cancer cells, especially when rendered resistant to drugs or isolated from metastatic sites, have high basal levels of TG2 expression. Indeed, inhibition of TG2 expression using the siRNA, antisense, or ribozyme approach has resulted in reversal of drug resistance in breast and lung cancer cells. Similarly, studies using breast and pancreatic cancer cells showed that downregulation of TG2 expression by siRNA inhibited their invasiveness whereas ectopic expression of TG2 promoted their invasiveness.

Despite all of these findings, the mechanism by which TG2 contributes to the development of chemoresistance and metastatic phenotypes remains unknown. In monocytic cells, TG2 could interact and form stable complexes with $\beta$1 and $\beta$3 integrins. This finding paved the way for delineation of the significance of increased TG2 expression in cancer cells. We previously demonstrated that in addition to $\beta$1-integrin, TG2 could bind to and form complexes with $\beta$4- and $\beta$5-integrin in breast cancer, malignant melanoma, and pancreatic cancer cells. TG2 is known to associate with integrins primarily in the extra-cellular domains of integrins and to promote their interaction with the extracellular matrix (ECM) ligands, such as fibronectin, collagen, and vitronectin. Therefore, it is possible that aberrant expression of TG2 may contribute to the aggressive behavior of PDAC as a result of constitutive activation of integrin-mediated cell survival signaling pathways.

Indeed, our efforts to understand the significance of increased TG2 expression in PDAC cells led us to the discovery that TG2 expression results in constitutive activation of FAK, Akt, and NF-$\kappa$B. Thus, TG2 expression activated and auto phosphorylated FAK (pY397), and downregulation of TG2 expression inhibited this activation. Moreover, TG2-induced activation of FAK results in activation of the PI3K/Akt cell survival signaling pathway (19). Our more recent studies have provided some interesting leads and suggest that expression of TG2 in PDAC cells is inversely correlated with PTEN expression. TG2 inhibited the phosphorylation of PTEN at serine-380 and promoted its degradation via the ubiquitin/proteasome pathway. Thus, TG2 plays a dual role in the FAK/PI3K/Akt signaling pathway by 1) promoting direct phosphorylation of FAK and 2) inhibiting its upstream phosphatase, PTEN, resulting in constitutive activation of the PI3K/Akt pathway.

Moreover, TG2 expression results in constitutive activation of NF-$\kappa$B in an inhibitor of KB kinase-independent manner. Under normal conditions, the inflammation-induced NF-$\kappa$B activation is transient, which is critical for the controlled growth and survival of normal cells. Thus, TG2-mediated constitutive activation of NF-$\kappa$B in cancer cells may be critical to conferring chemoresistance and metastatic phenotypes. Indeed, our recent data supported this contention and suggested that downregulation of TG2 expression by siRNA in drug-resistant breast cancer and PDAC cells results in inhibition of NF-$\kappa$B and increases their sensitivity to chemotherapeutic drugs. These results suggest that TG2 plays an important role in promoting cell survival signaling and thus protects PDAC cells against drug-induced cell death.

Importantly, the present study provided the proof of concept that therapeutic delivery of gene-specific siRNA to PDAC tumors can be achieved using DOPC liposomes. Two recent reports documented a similar effect of DOPC liposomal delivery of siRNA to silence the expression of the oncoprotein EphA2 and FAK. Using this approach, both studies documented encouraging responses to the treatment of ovarian tumors in mice. Thus, the significance of the results of this study can be rapidly transferred to the clinical setting for treatment of aggressive forms of PDA.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. An isolated siRNA that inhibits the expression of TG2 wherein the siRNA is targeted to at least one of the sequences defined by SEQ ID NO: 19 one having 90 percent homology thereto.

2. An expression vector useful in inhibiting TG2 expression and constitutive activation of NF-κB comprising isolate siRNA targeted to at least one of the sequences defined by SEQ ID NO: 19 or one having 90 percent homology thereto.

3. A method of modulating drug resistance in a cancer patient in need thereof comprising the step of administering to the patient a therapeutically effective amount of TG2-specific siRNA, wherein the expression of TG2 and the constitutive activation of NF-κB are inhibited by isolated siRNA targeted to at least one of the sequences defined by SEQ ID NO: 19 or SEQ ID NO: 20, or one having 90 percent homology thereto.

4. A method of treating metastasis in a cancer patient in need thereof comprising the step of administering to the patient a therapeutically effective amount of TG2-specific siRNA, wherein the expression of TG2 and the constitutive activation of NF-κB are inhibited by isolated siRNA targeted to at least one of the sequences defined by SEQ ID NO: 19 or SEQ ID NO: 20, or one having 90 percent homology thereto.

5. A method of treating cancer in a patient in need thereof comprising the step of administering to the patient a therapeutically effective amount of TG2-specific siRNA, wherein the expression of TG2 and the constitutive activation of NF-κB are inhibited by isolated siRNA targeted to at least one ofthe sequences defined by SEQ ID NO: 19 or SEQ ID NO: 20, or one having 90 percent homology thereto.

6. The method of claim 5 wherein the cancer is breast cancer, melanoma, pancreatic cancer or ovarian cancer.

* * * * *